United States Patent [19]
Chader et al.

[11] Patent Number: 5,840,686
[45] Date of Patent: Nov. 24, 1998

[54] PIGMENT EPITHELIUM-DERIVED FACTOR: CHARACTERIZATION OF ITS NOVEL BIOLOGICAL ACTIVITY AND SEQUENCES ENCODING AND EXPRESSING THE PROTEIN AND METHODS OF USE

[75] Inventors: Gerald J. Chader; Sofia Patricia Becerra; Joan P. Schwartz, all of Bethesda, Md.; Takayuki Taniwaki, Koga-Machi, Japan; Yukihiro Sugita, Rockville, Md.

[73] Assignee: The United States of America as represented by the Department of Health and Human Services, Washington, D.C.

[21] Appl. No.: 257,963

[22] Filed: Jun. 7, 1994

Related U.S. Application Data

[63] Continuation-in-part of Ser. No. 952,796, Sep. 24, 1992, abandoned.

[51] Int. Cl.$^6$ ........................................... A61K 38/17
[52] U.S. Cl. ........................ 514/12; 514/2; 514/8
[58] Field of Search ................ 514/2, 12; 435/240.1, 435/240.2, 240.21, 325

[56] References Cited

U.S. PATENT DOCUMENTS

| | | | |
|---|---|---|---|
| 1,700,691 | 1/1929 | Stuart | 424/95 |
| 4,477,435 | 10/1984 | Courtois et al. | 424/95 |
| 4,534,967 | 8/1985 | Jacobson et al. | 424/95 |
| 4,670,257 | 6/1987 | Guedon born Saglier et al. | 424/95 |
| 4,770,877 | 9/1988 | Jacobson | 424/95 |
| 4,996,159 | 2/1991 | Glaser | 435/70.3 |

FOREIGN PATENT DOCUMENTS 9324529  12/1993  WIPO.

OTHER PUBLICATIONS

Seigel et al., *Growth Factors,* vol. 10, pp. 289–297, 1994.
Genbank Data Bank, Accession No. M76979 (1991).
Becerra et al., "Recombinant Human Fetal Retinal Pigment Epithelium–Derived Factor (PEDF)," Abstract 658–50, presented at Investigative Ophthalmology & Visual Science Annual Meeting (May 3–May 8, 1992).
Becerra et al., "A Novel Retinal Neurotrophic Factor (PEDF): A Serine Protease Inhibitor?" presented at NIH Research Festival 1992 (Sep. 21–25, 1992).
Tombran–Tink et al., "RPE–54—A Unique RPE Product with Neuronal Differentiating Activity," *Investigative Ophthalmology & Visual Science,* 29, 414 (1989).
Tombran–Tink et al., "Neuronal Differentiation of Retinoblastoma Cells Induced by Medium Conditioned by Human RPE Cells," *Investigative Ophthalmology & Visual Science,* 30(8), 1700–1707 (1989).
Tombran–Tink et al., "PEDF: A Pigment Epithelium–derived Factor with Potent Neuronal Differentiative Activity," *Experimental Eye Research,* 53, 411–414 (1991).
Tombran–Tink et al., "Molecular Cloning and Chromoscomal Localization of the Gene for Human Pigment Epithelium–Derived Factor (PEDF)," *Investigative Ophthalmology & Visual Science,* 33(4), 828 (1992).
Zhiqiang Zou, et al., "Maspin, A Serpin With Tumor–Suppressing Activity In Human Mammary Epithelial Cells," *Science,* vol. 263, pp. 526–530, Jan. 28, 1994.
S.P. Becerra, et al., "Structure–Function Studies of Pigment Epithelium Derived Factor (PEDF)," *The FASEB Journal* (Abstract No. 192), vol. 7, No. 7, Apr. 20, 1993.
R. J. Pignolo, et al., "Senescent WI–38 Cells Fail To Express EPC–1, A Gene Induced In Young Cells Upon Entry Into The $G_0$ State," *The Journal of Biological Chemistry,* vol. 268, No. 12, Apr. 25, 1993, pp. 8949–8957.
J. Tombran–Tink, et al., "Neurotrophic Activity of Interphotoreceptor Matrix on Human Y79 Retinoblastoma Cells," *The Journal of Comparative Neurology,* 1992.

*Primary Examiner*—Paula K. Hutzell
*Assistant Examiner*—Stephen Gucker
*Attorney, Agent, or Firm*—Morgan & Finnegan, L.L.P.

[57] ABSTRACT

Nucleic acids encoding the neurotrophic protein known as pigment epithelium-derived factor (PEDF), a truncated version of PEDF referred to as rPEDF, and equivalent proteins, vectors comprising such nucleic acids, host cells into which such vectors have been introduced, recombinant methods for producing PEDF, rPEDF, and equivalent proteins, the rPEDF protein and equivalent proteins of rPEDF and PEDF -BP, -BX and BA, and the PEDF protein produced by recombinant methods Effects and uses of these variants on 1) neuronal differentiation (neurotrophic effect) 2) neuron survival (neuronotrophic effect) and 3) glial inhibition (gliastatic effect) are described.

6 Claims, 20 Drawing Sheets

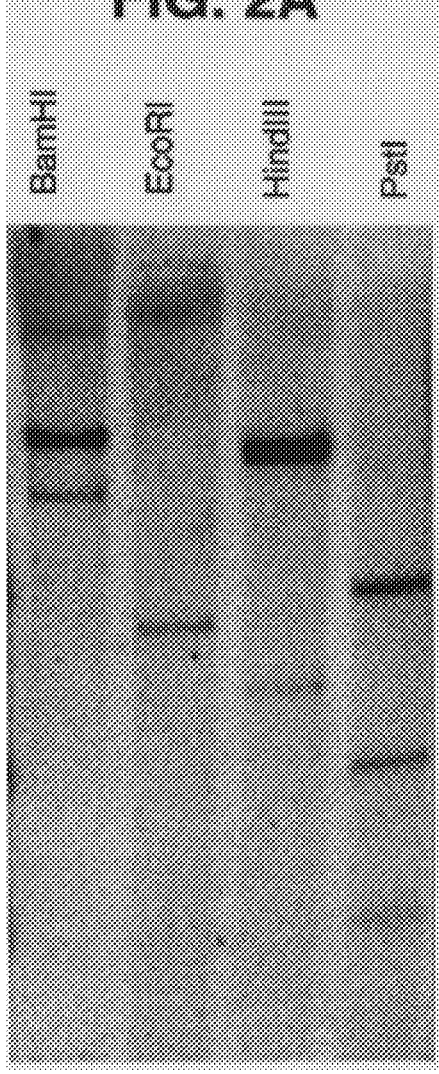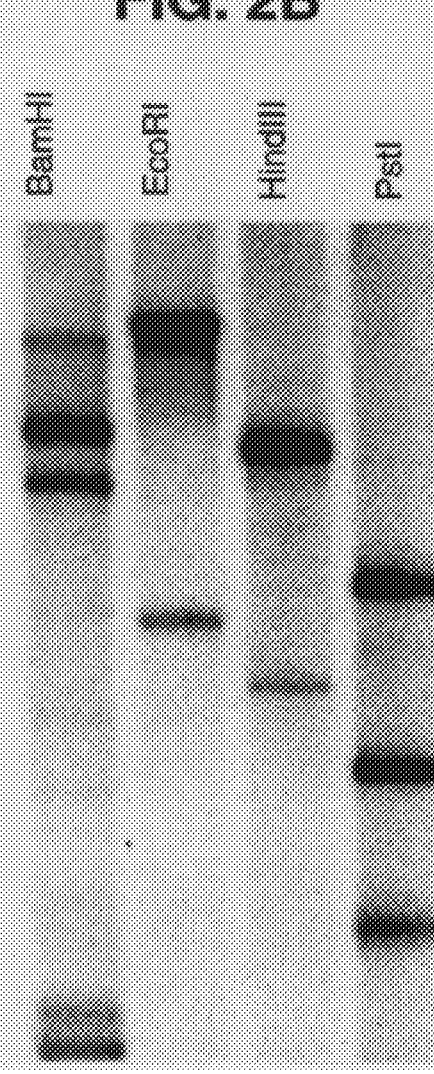

FIG. 3

```
                                                              ttcttttttgagacggggtctcgctctgctcgcccaggatggagtgcagtggtgtgatc    -650
tcagctcactgcaacctccgcctcccaggtttaagtgattctcctgcctcagactcccaagtagctggacta   -577
caggtgcgcgccaacacctgggtaattttgtttgtattttagtagagatggggtttcaccgtgttgacta    -505
ggctggtctcgaacctcctgacctcaggtgatccccggcctcggtctcccaaagtgctggggataacaagcg   -433
tgagccactgcgcccagctttgtttgcatttttaggtgagatggggtttcaccacgttggccaggctggtctt   -361
gaactcctgacctcaggtgatgacctgcctcagtctcccaaagtgctgattacaggcgttagcccctgcgc   -289
ccggcccctgaaggaaaatctaaaggaagagaggtgtgcaaatgtgtgccttaggcgtaatggatggtg    -217
gtgcagcagtgggttaaagttaacacgagacagtgatgcaatcacagaatccaaattgagtgcaggtcgcttt   -145
aagaaaggagtagctgtaatctgaagcctgctGGACGCTGGATTAGAAGGCAGCAAAAAAGCTCTGTGCTGG    -73
CTGGAGCCCCCTCAGTGCAGGCTTAGAGGGACTAGGCTGTGTGGAGCTGCAGCCGTATCCACAGGCCCCAGG    -1
gtaaagtag......................................................ttcttgcag    72
ATGCAGGCCCTGGTGCTACTCCTCTGCATTGGAGCCCTCCTCGGGCACAGCAGCCTGCCAGAACCCTGCCAGCC   145
CCCCGG                                                                      151
```

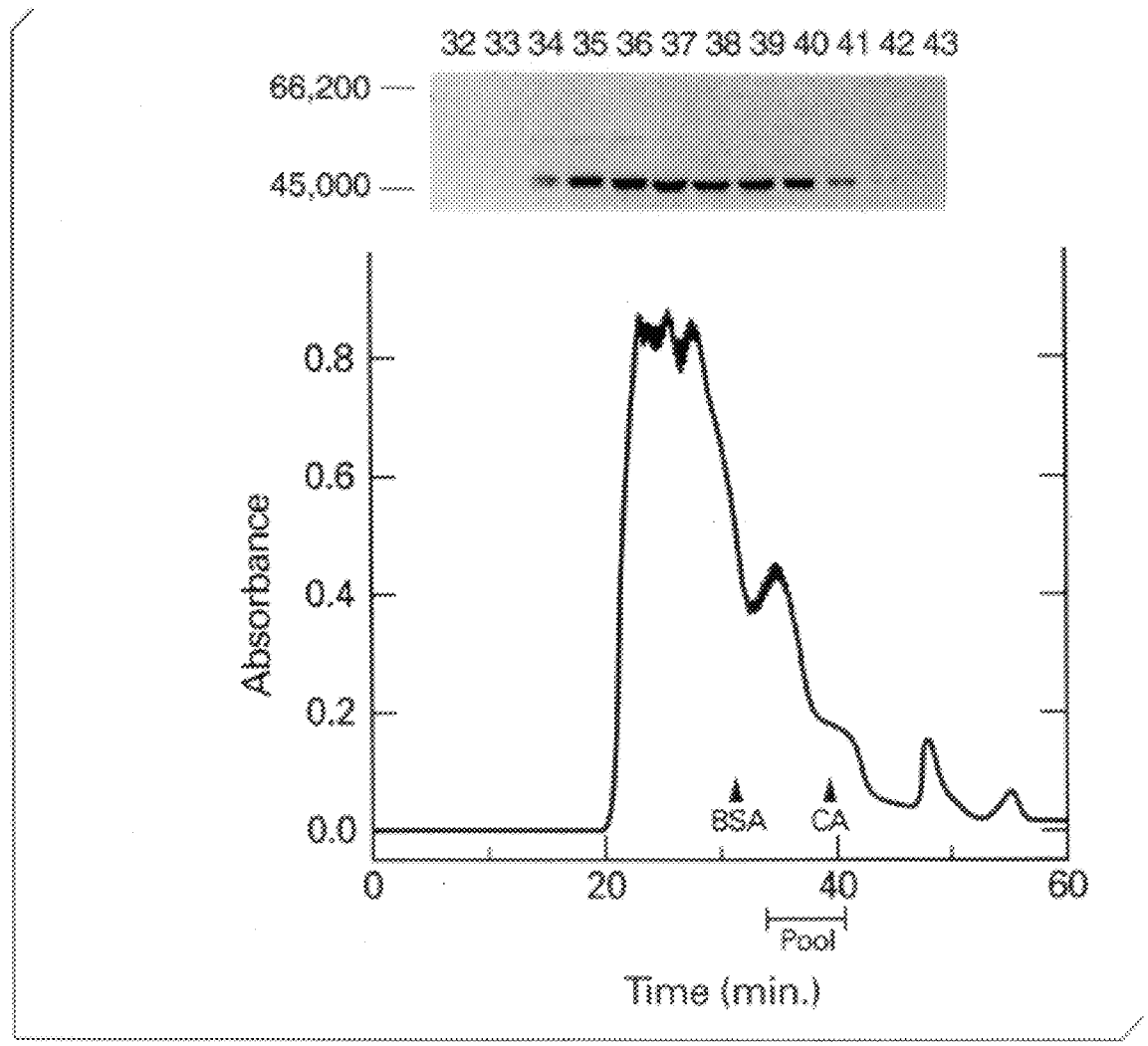

PIGMENT EPITHELIUM-DERIVED FACTOR: CHARACTERIZATION OF ITS NOVEL BIOLOGICAL ACTIVITY AND SEQUENCES ENCODING AND EXPRESSING THE PROTEIN AND METHODS OF USE

This application is a continuation-in-part of application Ser. No. 07/952,796 filed on Sep. 24, 1992, abandoned.

TECHNICAL FIELD OF THE INVENTION

This invention relates to a neurotrophic, neuronotrophic and gliastatic protein. More specifically, this invention relates to the biological properties of a protein known as pigment epithelium-derived factor (PEDF) and recombinant forms of the protein. This invention also relates to a truncated version of PEDF that is referred to as rPEDF. In addition to PEDF and rPEDF and functionally equivalent proteins, this invention relates to nucleic acids that encode rPEDF, and fragments thereof, to vectors comprising such nucleic acids, to host cells into which such vectors have been introduced, and to the use of these host cells to produce such proteins.

BACKGROUND OF THE INVENTION

Pigment epithelium-derived factor, otherwise known as pigment epithelium differentiation-factor, was identified in the conditioned medium of cultured fetal human retinal pigment epithelial cells as an extracellular neurotrophic agent capable of inducing neurite outgrowth in cultured human retinoblastoma cells (Tombran-Tink et al., *Invest. Ophthalmol. Vis. Sci.*, 30 (8), 1700–1707 (1989)). The source of PEDF, namely the retinal pigment epithelium (RPE), may be crucial to the normal development and function of the neural retina. A variety of molecules, including growth factors, are synthesized and secreted by RPE cells. Given that the RPE develops prior to and lies adjacent to the neural retina, and that it functions as part of the blood-retina barrier (Fine et al., *The Retina, Ocular Histology: A Text and Atlas,* New York, Harper & Row, 61–70 (1979)), the RPE has been implicated in vascular, inflammatory, degenerative, and dystrophic diseases of the eye (Elner et al., *Am. J. Pathol.*, 136, 745–750 (1990)). In addition to growth factors, nutrients and metabolites are also exchanged between the RPE and the retina. For example, the RPE supplies to the retina the well-known growth factors PDGF, FGF, TGF-α, and TGF-β (Campochiaro et al., *Invest. Ophthalmol. Vis. Sci.*, 29, 305–311 (1988); Plouet, *Invest. Ophthalmol. Vis. Sci.*, 29, 106–114 (1988); Fassio et al., *Invest. Ophthalmol. Vis. Sci.*, 29, 242–250 (1988); Connor et al., *Invest. Ophthalmol. Vis. Sci.*, 29, 307–313 (1988)). It is very likely that these and other unknown factors supplied by the RPE influence the organization, differentiation, and normal functioning of the retina.

In order to study and determine the effects of putative differentiation factors secreted by the RPE, cultured cells have been subjected to retinal extracts and conditioned medium obtained from cultures of human fetal RPE cells. For example, U.S. Pat. No. 4,996,159 (Glaser) discloses a neovascularization inhibitor recovered from RPE cells that is of a molecular weight of about 57,000±3,000. Similarly, U.S. Pat. Nos. 1,700,691 (Stuart), 4,477,435 (Courtois et al.), and 4,670,257 (Guedon born Saglier et al.) disclose retinal extracts and the use of these extracts for cellular regeneration and treatment of ocular disease. Furthermore, U.S. Pat. Nos. 4,770,877 (Jacobson) and 4,534,967 (Jacobson et al.) describe cell proliferation inhibitors purified from the posterior portion of bovine vitreous humor.

PEDF only recently has been isolated from human RPE as a 50-kDa protein (Tombran-Tink et al., *Invest. Ophthalmol. Vis. Sci.*, 29, 414 (1989); Tombran-Tink et al., *Invest. Ohthalmol. Vis. Sci.*, 30, 1700–1707 (1989); Tombran-Tink et al., *Exp. Eye Res.*, 53, 411–414 (1991)). Specifically, PEDF has been demonstrated to induce the differentiation of human Y79 retinoblastoma cells, which are a neoplastic counterpart of normal retinoblasts (Chader, *Cell Different.*, 20, 209–216 (1987)). The differentiative changes induced by PEDF include the extension of a complex meshwork of neurites, and expression of neuronal markers such as neuron-specific enolase and neurofilament proteins. This is why the synthesis and secretion of PEDF protein by the RPE is believed to influence the development and differentiation of the neural retina. Furthermore, PEDF is only highly expressed in undifferentiated human retinal cells, like Y79 retinoblastoma cells, but is either absent or downregulated in their differentiated counterparts. Recently, it was reported that PEDF MRNA is expressed in abundance in quiescent human fetal W1 fibroblast cells and not expressed in their senescent counterparts (Pignolo et al., 1993).

Further study of PEDF and examination of its potential therapeutic use in the treatment of inflammatory, vascular, degenerative, and dystrophic diseases of the retina and central nervous system (CNS) necessitates the obtention of large quantities of PEDF. Unfortunately, the low abundance of PEDF in fetal human eye and, furthermore, the rare availability of its source tissue, especially in light of restrictions on the use of fetal tissue in research and therapeutic applications, make further study of PEDF difficult at best. Therefore, there remains a need for large quantities of PEDF and equivalent proteins. Accordingly, the obtention of nucleic acids that encode PEDF and equivalent proteins, and the capacity to produce PEDF and equivalent proteins in large quantities would significantly impact upon the further study of PEDF, its structure, biochemical activity and cellular function, as well as the discovery and design of therapeutic uses for PEDF.

SUMMARY OF THE INVENTION

It is an object of the present invention to provide nucleic acids encoding for PEDF and functional fragments thereof, vectors comprising such nucleic acids, host cells into which such vectors have been introduced, and a recombinant method of producing PEDF and equivalent proteins. It is another object of the present invention to obtain the genomic DNA sequences encoding for PEDF, identify the intron-exon junctions, the chromosome location in the human genome, and to provide the regulatory regions of the gene which flank the genomic sequence.

It is a further object of the present invention to provide structural characteristics of PEDF and its similarities to the serpin family of serine protease inhibitors, both structural and functional.

It is yet another object of the present invention to provide PEDF and equivalent proteins produced in accordance with such a recombinant method, wherein the PEDF and equivalent proteins so produced are free from the risks associated with the isolation of PEDF from naturally-occurring source organisms.

Another object of the present invention is to provide nucleic acids for a truncated version of PEDF, referred to as rPEDF, and equivalent proteins, vectors comprising such nucleic acids, host cells into which such vectors have been introduced, and a recombinant method of producing rPEDF and equivalent proteins. It is also an object of the present invention to provide rPEDF and equivalent proteins produced in accordance with such a recombinant method.

It is a further object of the invention to provide a PEDF protein having neuronotrophic and gliastatic activity. The neuronotrophic activity is seen in the prolonged survival of neuronal cells. The gliastatic activity is observed in the inhibition of growth of glial cells in the presence of PEDF or active fragment thereof. It is another object of the invention to provide methods for treating neuronal cells so as to promote/enhance neuron survival and prevent growth of glial cells, comprising treating such cell populations with an effective amount of PEDF or an active fragment thereof.

It is yet another object of the present invention to provide antibodies which specifically recognize PEDF, either monoclonal or polyclonal antibodies, raised against native protein, the recombinant protein or an immunoreactive fragment thereof. It is an object of the invention to provide methods for detecting PEDF by immunoassay using such antibody preparation in determining aging and/or other degenerative diseases. Another object of the invention relates to a method of using PEDF antibodies to specifically inhibit PEDF activity.

These and other objects and advantages of the present invention, as well as additional inventive features, will be apparent from the description of the invention provided herein.

DESCRIPTIONS OF THE FIGURES

FIG. 1: Human PEDF Gene Structure: Restriction map and organization of the human PEDF gene. Exons 1–8 are indicated by black boxes and numbered E1–E8. Introns and flanking DNA are represented by horizontal line. Positions of several genomic clones are shown below the diagrammed gene. The organization of this gene was established from sequence analysis of jt101, 106, 108, 109, 116, and Ir117 genomic clones. Recognition sites for the restriction endonuclease, NotI, BamHI and EcoRI are delineated by vertical bars.

FIG. 2A and B: Southern analysis of human genomic DNA (A) and P147 (B) restricted with Bam HI, EcoRI, HindIII and PstI endonuclease. Southern membranes from Pulsed-field electrophoretic gel profiles were probed with radioactively labelled PEDF cDNA. The pattern of hybridization of P147 DNA is consistent with total human genomic DNA. Size markers are indicated.

FIG. 3: Structure of the PEDF Promoter: Exon 1 (uppercase) and 5' flanking region of the human PEDF gene (lowercase) The first nucleotide of the methionine initiation codon has been designated as position #1. The 3' intron is in lowercase letters. Genbank accession no. M76979.

FIG. 4A, B, and C: Northern Blot analysis of PEDF mRNA: Gene expression analysis of the human PEDF transcript in a number of human adult and fetal tissues. Tissues from which RNA was obtained are shown above corresponding lanes. Membranes contain 2 ug poly (A) RNA for each sample and were probed with radioactively labelled cDNA for human PEDF. A single 1.5 kb transcript is seen in both adult and fetal tissues with the greatest intensity of hybridization in liver, testis, skeletal muscle and ovary while the signal for brain, pancreas and thymus was significantly weaker than that for other tissues. No significant signal was detected for adult kidney and spleen. A significant difference in PEDF MRNA levels seen between adult and fetal kidney.

FIG. 5A, B, and C: Evolutionary relatedness of the Human PEDF gene: Each lane represents a total of 8 ug of genomic DNA for each species digested with Eco RI. Southern blot analysis is shown with a PEDF probe. Hybridization signals for chicken (A), mammals (B) and primates (C) is shown. A large fragment of approximately 23 kb is seen in all primates and many mammalian species. In addition several polymorphisms are seen in the different mammalian species examined.

FIG. 6A & 6B: Relationship between cell density plated and optical density measured by MTS assay. Different concentrations of postnatal-day 8 cerebellar granule cells were added to 96 well plate and cultured in serum-containing medium (6A), or chemically defined medium (6B). Optical density was measured on days in vitro (DIV) 1, 4, or 7. Square, DIV 1; Solid circle, DIV 4; Open circle, DIV7. The data are plotted as function of cell density (n=6).

FIG. 7: Time course for PEDF stimulation of cell survival in chemically-defined medium. Postnatal-day 8 cerebellar granule cells were cultured in 96 well plate. PEDF was added at DIV 0 and the optical density was then measured on DIV 1, 4, 7, or 10. Solid bar, control; cross-hatched bar, PEDF treated (50 ng/ml); striped bar, PEDF treated (500 ng/ml). The data are expressed as optical density/well (means±SEM, n=6). Statistical analysis was done by two way ANOVA post-hoc Scheefe test. **$P<0.0001$ versus control.

FIG. 8: Dose-response curve for PEDF in chemically defined medium. Different concentrations of PEDF were added on DIV 0 and MTS assay was carried out on DIV 7. The data are expressed as ratio to control (mean±SEM, n=6). Statistical analysis was done by one way ANOVA post-hoc Scheffe F test. **$P<0.0001$ vesus control.

FIG. 9: MTS assay of postnatal day 5 cerebellar granule cells at DIV 1 and DIV 2. Postnatal-day 5 cerebellar granule cells were cultured in 96 well plate using serum-containing medium without Ara-C (A), or chemically defined medium without F12(B). The MTS assay was carried out on DIV 1 and 2. Solid bar, control; Striped bar, PEDF treated (500 ng/ml). The data are expressed as optical density/well (means±SEM, n=6). Statistical analysis was done by two way ANOVA post-hoc Scheffe F test. **$P <0.0005$ vesus control.

FIG. 10: BrdU incorporation into postnatal day 5 cerebellar granule cells. Postnatal-day 5 cerebellar granule cells were cultured in a 96 well plate using serum-containing medium (SCM) without Ara-C, or chemically defined medium (CDM) without F12. PEDF was added on DIV 0, BrdU was added on DIV 1 and the cells were fixed on DIV 2. Solid bar, control; Striped bar, PEDF treated (500 ng/ml). The number of labeled nucleic acids are expressed as a percentage of total cell population (mean±SEM). For each value, 3000 cells was counted at least.

FIG. 11: Relationship between cell density and neurofilament content measured by ELISA. Different concentrations of postnatal-day 8 cerebellar granule cells are added to 96 wells and cultured. Optical density was measured on DIV 7. The data are plotted as a function of cell density.

FIG. 12: Neurofilament ELISA assay in postnatal-day 8 cerebellar granule cells. Cells were cultured in a 96 well plate with or without PEDF using serum-containing medium (SCM) or chemically defined medium (CDM). After fixing cells on DIV 7, the neurofilament ELISA was carried out and the data are expressed as ratio to control (mean±SEM, n=6 to 10). Solid bar, control; Striped bar, PEDF treated (500 ng/ml). Statistical analysis was done by two way ANOVA post-hoc Scheffe F test. *$P<0.05$ vesus control.

FIG. 13: Summary of PEDF neuronotrophic effects through 10 days in culture.

FIG. 14: Effects of truncated peptides BP and BX on CGC viability.

FIG. 15: Effect of PEDF on astroglia from cerebellum.

FIG. 16: Effect of PEDF on cerebellar microglia.

FIG. 17A and B: Purification of PEDF-immunoreactive protein from bovine IPM. Washes of bovine IPM were subjected to A) TSK-3000 size-exclusion chromatography followed by B) Mono-S chromatography. Western blot inserts demonstrate the fractions containing PEDF.

FIG. 18: Enzymatic deglycosylation of PEDF as demonstrated by Western blotting. PEDF treatment is given at the top of each lane. Numbers indicate positions of mol. wt. standards.

FIG. 19A and B: Antibody to rPEDF specifically recognizes native PEDF at a high titer. A) Western blot demonstrating effectiveness of the antibody to at least 1:50,000 dilution and that addition of excess rPEDF completely blocks band visualization. B) Slot-blot analysis shows the ability to detect <1 ng of native bovine PEDF protein.

FIG. 20: Negative effect of PEDF antibody on neurite extension in Y-79 cells. Top row: bovine serum albumin (BSA) control cultures. Middle row: antibody effect on neurite-induction by native bovine PEDF protein. Bottom row: antibody effect on neurite induction by interphotoreceptor matrix (IPM).

FIG. 21A and B: Phase microscopy analysis of neurite outgrowth in the presence (B) or absence (A) of PEDF.

FIG. 22A and B: Phase microscopy analysis of neurite outgrowth in the presence of recombinant PEDF (A) and native, isolated PEDF (B).

FIG. 23: Schematic Diagram of C-terminal deletions of rPEDF.

DETAILED DESCRIPTION OF THE INVENTION

Figure 1:
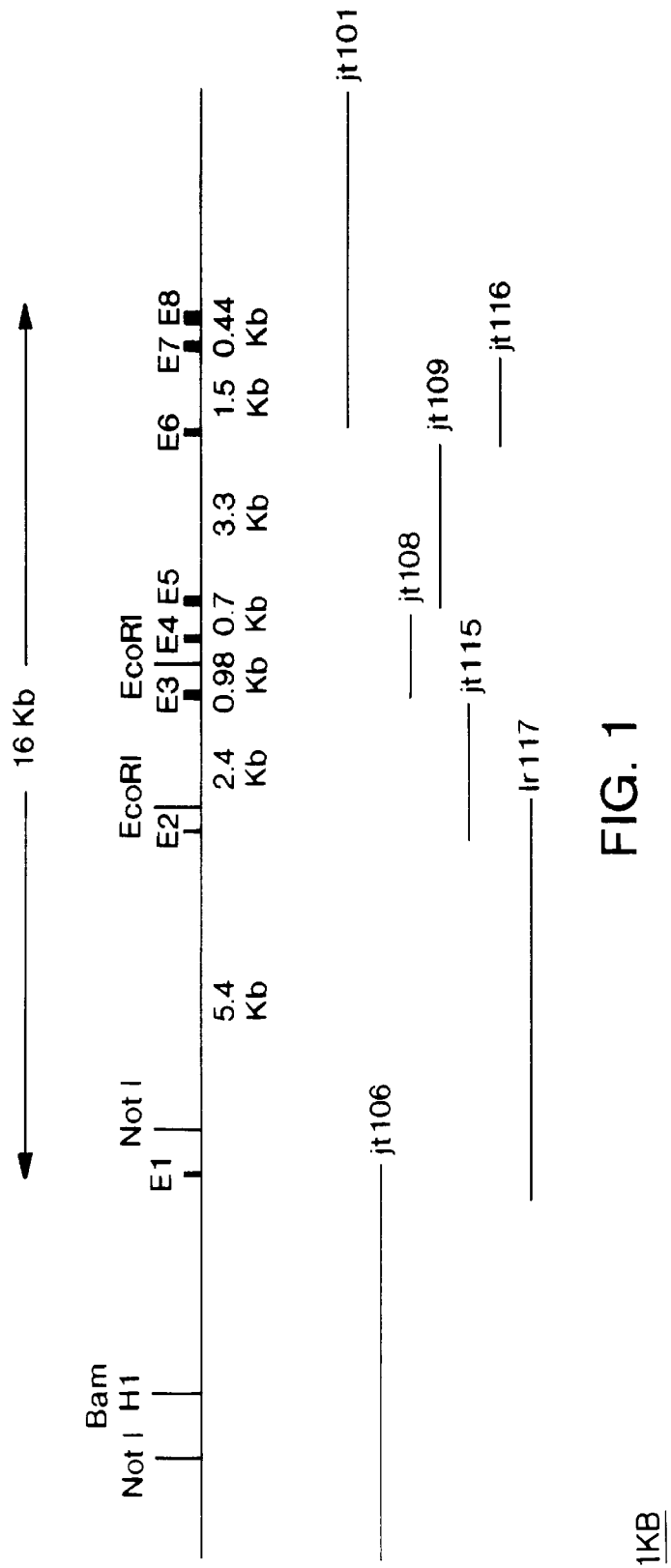

The present invention relates to a protein having novel, important and unobvious properties. Pigment epithelium-derived factor (PEDF) is a protein having neurotrophic, neuronotrophic and gliastatic characteristics. The present invention further relates to the DNA sequences coding for the PEDF gene, the genomic region of DNA containing the PEDF gene and fragments of the PEDF gene encoding for protein fragments of PEDF having biological activity.

"Neurotrophic" activity is defined herein as the ability to induce differentiation of a neuronal cell population. For example, PEDF's ability to induce differentiation in cultured retinoblastoma cells is considered neurotrophic activity. "Neuronotrophic" activity is defined herein as the ability to enhance survival of neuronal cell populations. For example, PEDF's ability to act as a neuron survival factor on neuronal cells is neuronotrophic activity. "Gliastatic" activity is defined herein as the ability to inhibit glial cell growth and proliferation. For example, PEDF's ability to prevent growth and/or proliferation of glial cells is gliastatic activity.

Based upon the protein amino acid sequence elucidated in the present invention, PEDF has been found to have extensive sequence homology with the serpin gene family, members of which are serine protease inhibitors. Many members of this family have a strictly conserved domain at the carboxyl terminus which serves as the reactive site of the protein. These proteins are thus thought to be derived from a common ancestral gene. However the developmental regulation differs greatly among members of the serpin gene family and many have deviated from the classical protease inhibitory activity (Bock 1990, Patson et al., 1990, Stein et al., 1989). Although PEDF shares sequence homology with serpins, analysis of the cDNA sequence indicates that it lacks the conserved domain and thus may not function as a classical protease inhibitor.

Genomic sequencing and analysis of PEDF has provided sequences of introns and exons as well as approx. 4 kb of 5'-upstream sequence. The present invention demonstrates the localization of the gene for PEDF to 17p13.1 using both in situ hybridization and analyses of somatic cell hybrid panels (Tombran-Tink, et al., (1994) Genomics, 19:266–272). This is very close to the p53 tumor suppressor gene as well as to the chromosomal localization of a number of hereditary cancers unrelated to mutations in the p53 gene product PEDF thus becomes a prime candidate gene for these cancers.

Tissue Distribution

Although PEDF is particularly highly expressed by RPE cells, it is detectable in most tissues, cell types, tumors, etc. by Northern and Western blot analyses. It is readily detected, for example in vitreous and aqueous humors. The important question of subcellular localization of PEDF has also been addressed. Although the bulk of the PEDF appears to be secreted, we have used a PEDF antibody to probe cultured monkey RPE cells and found that PEDF is associated with the nucleus as well as with very specific cytoskeletal structures in the cytoplasm. Importantly, this varies as to the age of the cells and the specific cell-cycle state examined. For example, the protein appears to concentrate at the tips of the pseudopods of primate RPE cells that interact with the substratum during the initial stages of attachment. Later though, this staining disappears and there is appearance of the protein in association with specific cytoskeletal structures and the nucleus. Thus it appears that PEDF plays an important intracellular role in both nucleus and cytoplasm.

Involvement in Cell Cycle

The present invention indicates that there is expression in dividing, undifferentiated Y-79 cells and little or no expression in their quiescent., differentiated counterparts (Tombran-Tink, et al., 1994 Genomics, 19:266–272). Pignolo et al. (1993, J. Biol. Chem., 268:2949–295) have demonstrated that the synthesis of PEDF in WI-38 fibroblast cells is restricted to the $G_0$ stage of the cell cycle in young cells. Moreover, in old senescent cells, PEDF messenger RNA is absent.

Production of Recombinant PEDF.

Segmentation of the PEDF polypeptide is basic to studies on structure-function. For this purpose, expression vectors containing fragments of PEDF coding sequences provide an excellent source for synthesizing and isolating different regions of the PEDF polypeptide. Expression of human fetal PEDF sequences was achieved with E. coli expression vectors and the human fetal PEDF cDNA. We have shown that the recombinant PEDF product (rPEDF) is a biologically-active neurotrophic factor and is obtained in yields on the order of 1.3 mg/g of wet E. coli cells. Truncated peptides can also be made from appropriate molecular biological constructs and expressed in E. coli. Using these products, we have evidence that two distinct regions on the PEDF primary structure can be distinguished: 1) an "active site" conferring neurotrophic activity on the molecule that is located within amino acid residues 44–121 near the N-terminal of the protein and 2) a region near the C-terminal with homology to a serpin exposed loop i.e., the "classical" serpin active site.

These results suggest 1) that the overall native conformation of PEDF is not required for neurite outgrowth and 2) that inhibition of serine proteases can not account for the biological activity of PEDF. We now have a series of truncated rPEDF constructs that span the protein sequence and can pinpoint the specific neurotrophic "active site" near the N-terminal.

Characterization with a highly specific polyclonal antibody

Purified recombinant human PEDF was used to develop a polyclonal antibody ("Anti-pREDF") that specifically blocks the PEDF-mediate neurotrophic activity. Furthermore, the anti-rPEDF completely blocks the IPM-induced neurotrophic activity.

Neuronotrophic properties of PEDF

Figure 4A:
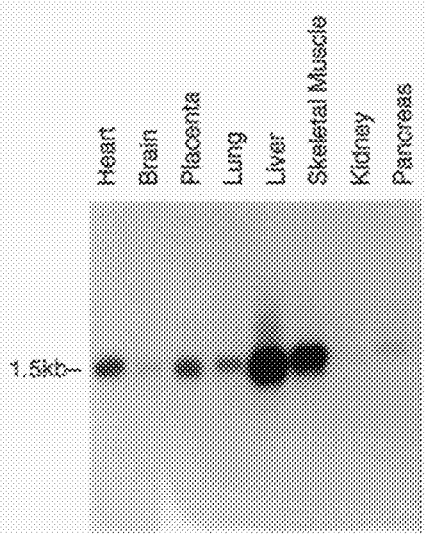
Figure 4B:
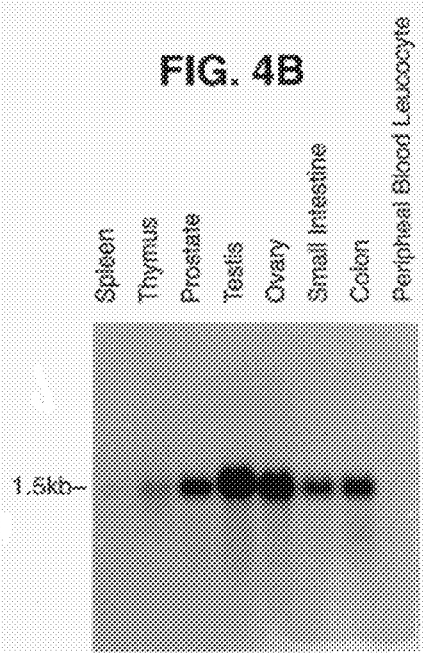
Figure 4C:
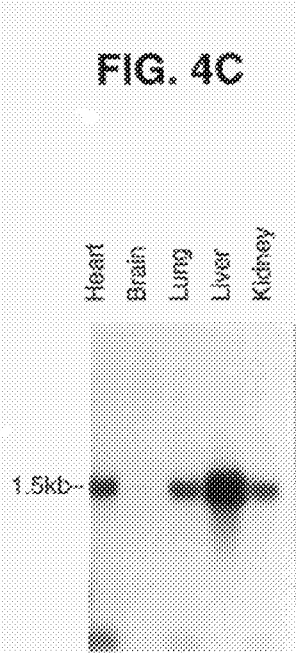

In addition to demonstrating that native PEDF and rPEDF are neurotrophic in the Y-79 and Weri tumor cell systems, the present invention determined whether PEDF had an effect on normal neurons in primary culture. For this purpose, studies were conducted using cultures of normal cerebellar granule cells (CGCs) prepared from the 8-day postnatal rat. Cells treated with rPEDF did not respond to treatment by exhibiting a more neuronal morphological appearance. However, PEDF had a large effect on granule cell survival. Since these cells are not tumorous or transformed cells, they have a finite life in culture, dying in about 21 days depending on the culture medium. PEDF-treated culture, however, contained up to 10-fold more cells after 10 days of culture in serum-free medium compared to non-treated culture (FIG. 4). These results were determined; 1) by direct microscopic observation and cell counting and 2) use of an MTS (tetrazolium/formazan) assay which determines live cell numbers (See example 11). Thus, PEDF has a dramatic effect on CNS neuron survival and should be added to the short list of newly-emerging "neuronotrophic" proteins.

In General Tissue Culture Research:

Two problems that generally plague any tissue culture experiment using neurons and glia is that the neurons tend to die quickly and that glia tend to overrun the culture dish. PEDF or its peptides can help in both regards. Thus, one commercial use of PEDF might be as a general culture medium additive when CNS cells are to be cultured.

In CNS Transplantation Studies:

It is thought that transplantation of neurons may cure certain pathologies. For example, in Parkinson's disease, transplantation of specific fetal brain cells into patients could alleviate or cure the problems associated with the disease. One of the major problems to contend with, though, would be to prolong the life of the transplanted cells and to keep them differentiated, e.g. secreting the proper substances, etc. Pretreatment of the cells with PEDF could aid in both of these areas. Similarly, transfection of either neurons or astroglia with the PEDF gene before implantation can be a long-term source of PEDF at the transplantation site.

There is much activity in attempts at transplantation of neural retina and photoreceptor cells to help cure blindness. Attempts to date have not been fruitful both due to non-differentiation and death of the grafts. Again, PEDF may help in both regards. Specifically, photoreceptor neurons to be transplanted can be pretreated with PEDF or the gene transfected into the cells before surgery. Alternatively, PEDF can be transfected at high levels into adjacent retinal pigment epithelial (RPE) cells where they can serve as a supranormal source of the protein. Several investigators have now shown that cultured RPE cells survive very well after transplantation into the interphotoreceptor space of test animals. Transfection of human RPE cells in vitro with the PEDF gene then use of them in retinal transplantation thus is feasible.

In Neurodegenerative Diseases:

Many neurodegenerative diseases and other insults to the CNS (brain and retina) are typified by death of neurons and overpopulation by glia (gliosis). PEDF can be used effectively in these conditions to prolong the life and functioning of the primary neurons and to stave off the glial advance. PEDF can be effective, for example, in blocking microglial activation in response to CNS injury as well as prolonging/sparing the lives of neurons.

In the retina, it is predictable that PEDF inhibits the Muller glial cells. Since Muller cells are similar to astroglia, PEDF would be similarly effective in blocking gliosis in conditions such as retinal detachment, diabetes, Retinitis Pigmentosa, etc. as well as sparing the lives of the retinal neurons.

In Glial Cancers:

Most of the major forms of cancer that strike the CNS involve glial elements, PEDF is a gliastatic factor that can be used in combination with other forms of therapy. For example, along with surgery, PEDF can effectively inhibit the spread or reoccurrence of the disease.

Genetic Analysis

The present invention relates to the determination of the organization of the human PEDF gene and its promoter and analysis of its evolutionary relatedness and expression in a variety of human fetal and adult tissues.

The present invention provides, among other things, a nucleic acid which encodes PEDF. In particular, a cDNA sequence is provided as set forth in SEQ ID NO:1. This cDNA sequence codes for PEDF, which has the amino acid sequence set forth in SEQ ID NO:2. The cDNA and amino acid sequences are listed in the GenBank® Data Bank under accession number M76979. Further genomic sequences are provided in FIG. 1 and in SEQ ID NO: 9 through SEQ ID NO: 12. The location of intron-exon junctions are identified in table 1 and SEQ ID NO: 25 through SEQ ID NO: 40.

The term "nucleic acid" refers to a polymer of deoxyribonucleic acid (DNA) or ribonucleic acid (RNA), which can be derived from any source, can be single- or double-stranded, and can optionally contain synthetic, non-natural, or altered nucleotide which are capable of being incorporated into DNA or RNA polymers. The nucleic acid of the present invention is preferably a segment of DNA.

The present invention further provides truncated versions of PEDF. The largest of these is referred to as rPEDF, and comprises the amino acid sequence Met-Asn-Arg-Ile fused to $Asp^{44}$ . . . $Pro^{418}$ of PEDF, the amino terminus of which has been deleted. The rPEDF protein comprises the amino acid sequence of SEQ ID NO:3. The present invention also provides a nucleic acid which encodes a protein comprising the amino acid sequence of rPEDF, i.e., the amino acid sequence of SEQ ID NO:3.

One who is skilled in the art will appreciate that more than one nucleic acid may encode any given protein in view of the degeneracy of the genetic code and the allowance of exceptions to classical base pairing in the third position of the codon, as given by the so-called "Wobble rules".

Moreover, nucleic acids that include more or less nucleotide can result in the same or equivalent proteins. Accordingly, it is intended that the present invention encompass all nucleic acids that encode the amino acid sequences of SEQ ID NO:2 and SEQ ID NO:3, as well as equivalent proteins. The phrase "equivalent nucleic acids" is intended to encompass all of these nucleic acids.

It also will be appreciated by one skilled in the art that amino acid sequences may be altered without adversely affecting the function of a particular protein. In fact, some alterations in amino acid sequence may result in a protein with improved characteristics. The determination of which amino acids may be altered without adversely affecting the function of a protein is well within the ordinary skill in the art. Moreover, proteins that include more or less amino acids can result in proteins that are functionally equivalent. Accordingly, it is intended that the present invention encompass all amino acid sequences that result in PEDF protein or functional protein fragments thereof.

Some examples of possible equivalent nucleic acids and equivalent proteins include nucleic acids with substitutions, additions, or deletions which direct the synthesis of the rPEDF protein and equivalent protein fragments thereof; nucleic acids with different regulatory sequences that direct the production of rPEDF proteins; variants of rPEDF which possess different amino acids and/or a number of amino acids other than four fused to the amino terminal end of the protein; and PEDF and rPEDF and functional protein fragments thereof with amino acid substitutions, additions, deletions, modifications, and/or posttranslational modifications, such as glycosylations, that do not adversely affect activity.

The present invention also provides a vector which comprises a nucleic acid of SEQ ID NO:1, a nucleic acid which encodes a protein comprising the amino acid sequence of SEQ ID NO:2 or an equivalent protein, a nucleic acid which encodes a protein comprising the amino acid sequence of SEQ ID NO:3 or an equivalent protein, and equivalent nucleic acids thereof.

In particular, the present invention provides the vector wFS17, which comprises the nucleic acid of SEQ ID NO:1, and the vector PEV-BH, which comprises a nucleic acid which encodes a protein comprising the amino acid sequence of SEQ ID NO:3. It will be appreciated by those skilled in the art that the cDNA inserts described can be present in alternative vectors. For example, inserts can be in vectors of different nature, such as phages, viral capsids, plasmids, cosmids, phagemids, YACs, or even attached to the outside of a phage or viral capsid. The vectors can differ in host range, stability, replication, and maintenance. Moreover, the vectors can differ in the types of control exerted over cloned inserts. For example, vectors can place cloned inserts under the control of a different promoter, enhancer, or ribosome binding site, or even organize it as part of a transposon or mobile genetic element.

The present invention also provides a host cell into which a vector, which comprises a nucleic acid of SEQ ID NO:1, a nucleic acid which encodes a protein comprising the amino acid sequence of SEQ ID NO:2 or an equivalent protein, a nucleic acid which encodes a protein comprising the amino acid of SEQ ID NO:3 or an equivalent protein, or an equivalent nucleic acid thereof, has been introduced. In particular, the host cell may have the vector πFS17, which comprises the nucleic acid of SEQ ID NO:1, or the vector pEV-BH, which comprises a nucleic acid which encodes a protein comprising the amino acid sequence of SEQ ID NO:3.

The vectors of the present invention can be introduced into any suitable host cell, whether eukaryotic or prokaryotic. These host cells may differ in their preferred conditions for growth, their nutritive requirements, and their sensitivity to environmental agents. Any appropriate means of introducing the vectors into the host cells may be employed. In the case of prokaryotic cells, vector introduction may be accomplished, for example, by electroporation, transformation, transduction, conjugation, or mobilization. For eukaryotic cells, vectors may be introduced through the use of, for example, electroporation, transfection, infection, DNA coated microprojectiles, or protoplast fusion.

The form of the introduced nucleic acid may vary with the method used to introduce the vector into a host cell. For example, the nucleic acid may be closed circular, nicked, or linearized, depending upon whether the vector is to be maintained as an autonomously replicating element, integrated as provirus or prophage, transiently transfected, transiently infected as with a replication-disabled virus or phage, or stably introduced through single or double crossover recombination events.

The present invention also provides a method of producing PEDF, rPEDF, and equivalent proteins, which method comprises expressing the protein in a host cell. For example, a host cell into which has been introduced a vector which comprises a nucleic acid of SEQ ID NO:1, a nucleic acid which encodes a protein comprising the amino acid sequence of SEQ ID NO:2 or an equivalent protein, a nucleic acid which encodes a protein comprising the amino acid of SEQ ID NO:3 or an equivalent protein, or an equivalent nucleic acid thereof, may be cultured under suitable conditions to produce the desired protein. In particular, a host cell into which has been introduced the vector πFS17, which comprises the nucleic acid of SEQ ID NO:1, or the vector pEV-BH, which comprises a nucleic acid which encodes a protein comprising the amino acid sequence of SEQ ID NO:3, may be cultured under suitable conditions to produce the proteins comprising the amino acid sequences of SEQ ID NO:2 and SEQ ID NO:3, respectively.

The present invention also provides recombinantly produced PEDF, and functional protein fragments thereof which have been produced in accordance with the aforementioned present inventive method of culturing an appropriate host cell to produce the desired protein. The production of a protein such as PEDF by recombinant means enables the obtention of large quantities of the protein in a highly purified state, free from any disease-causing agents which may accompany the protein isolated or purified from a naturally occurring source organism, and obviates the need to use, for example, fetal tissue as a source for such a protein.

Recombinant PEDF and functional protein fragments thereof may be supplied as active agents to cells by a variety of means, including, for example, the introduction of nucleic acids, such as DNA or RNA, which encode the protein and may be accordingly transcribed and/or translated within the host cell, the addition of exogenous protein, and other suitable means of administration as are known to those skilled in the art. In whatever form in which supplied, the active agent can be used either alone or in combination with other active agents, using pharmaceutical compositions and formulations of the active agent which are appropriate to the method of administration. Pharmaceutically acceptable excipients, i.e., vehicles, adjuvants, carriers or diluents, are well-known to those who are skilled in the art, and are readily available. The choice of excipient will be determined in part by the particular compound, as well as by the particular method used to administer the compound. Accordingly, there is a wide variety of suitable formulations which can be prepared in the context of the present invention. However, pharmaceutically acceptable excipients not altering the neurotrophic, neuronotrophic and gliastatic activities of the recombinant protein are preferred.

The following examples serve to illustrate further the present invention and are not to be construed as limiting its scope in any way.

EXAMPLE 1

This example describes the trypsin digestion of PEDF and the amino acid sequencing of the resulting fragments.

PEDF was purified from the medium of a primary culture of human fetal RPE cells by high performance liquid chromatography (HPLC). The HPLC-purified PEDF was then reduced and alkylated. Afterwards, it was dried and redissolved in 50 μl of CRA buffer (8M urea, 0.4M ammonium carbonate, pH 8.0), and 5 μl of 45 mM dithiothreitol (DTT) (Calbiochem, San Diego, Calif.) were added. After heating at 50° C. for 15 minutes, the solution was cooled, and 5 μl of 100 mM iodoacetic acid (Sigma Chem. Co., St. Louis, Mo.) were added. After 15 minutes, the solution was diluted to a concentration of 2M urea and subjected to trypsin digestion (Boehringer-Mannheim, Indianapolis, Ind.) for 22 hours at 37° C. using an enzyme:substrate ratio of 1:25 (wt/wt). Tryptic peptides were separated by narrowbore, reverse-phase HPLC on a Hewlett-Packard 1090 HPLC, equipped with a 1040 diode array detector, using a Vydac 2.1 mm×150 mm C18 column. A gradient of 5% B at 0 minutes, 33% B at 63 minutes, 60% B at 95 minutes, and 80% B at 105 minutes, with a flow rate of 150 μl/minute, was used. In this gradient, buffer A was 0.06% trifluoroacetic acid/H$_2$O, and buffer B was 0.055% trifluoroacetic acid/acetonitrile. Chromatographic data at 210 and 277 nm, and UV spectra from 209 to 321 nm, of each peak were obtained. Samples for amino-terminal sequence analysis were applied to a polybrene precycled glass fiber filter and subjected to automated Edman degradation (Harvard Microchemical Facility, Boston, Mass.) on an ABI model 477A gas-phase protein sequencer (program NORMAL 1). The resulting phenylthiohydantoin amino acid fractions were manually identified using an on-line ABI Model 120A HPLC and Shimadzu CR4A integrator.

Trypsin digestion of purified PEDF and amino acid analysis of the resulting fragments yielded nonoverlapping peptide sequences, including the sequences JT-3 (SEQ ID NO:6):

Thr Ser Leu Glu Asp Phe Tyr Leu Asp Glu
1              5                   10
Glu Arg Thr Val Arg Val Pro Met Met
                  15 and

JT-8 (SEQ ID NO:7):
Ala Leu Tyr Tyr Asp Leu Ile Ser Ser Pro
1              5                   10
Asp Ile His Gly Thr Tyr Lys Glu Leu Leu
                  15                  20
Asp Thr Val Thr Ala Pro Gln Xaa Asn
                  25

EXAMPLE 2

This example describes the construction of oligonucleotides, based on the peptide sequences of Example 1, the use of the oligonucleotides in the isolation of PEDF cDNA, and the sequencing of PEDF cDNA.

Based on the JT-3 and JT-8 peptide sequences of Example 1 and codon usage data, the oligonucleotides oFS5665 (SEQ ID NO:4): 5'-AGYAAYTTYTAYGAYCTSTA-3' and oFS5667 (SEQ ID NO:5): 5'-CTYTCYTCRTCSAGRTARAA-3' were constructed on an ABI 392 DNA/RNA Synthesizer and used as primers in a polymerase chain reaction (PCR).

A human fetal eye Charon BS cDNA library (obtained from Dr. A. Swaroop of the Kellog Eye Institute) was amplified once (Sambrook et al., *Molecular Cloning: A Laboratory Manual,* 2nd ed., Cold Spring Harbor Press, Cold Spring Harbor, N.Y. (1989)) and screened by PCR (Friedman et al., Screening of λgt11 Libraries, In: *PCR Protocols: A Guide to Methods and Applications,* Innis et al., eds., Academic Press, N.Y. (1990), pp. 253–260) using a Techne thermal cycler and standard reagents (GeneAMP, Perkin-Elmer Cetus), except that MgSO$_4$ was used at 3 mM. A PCR amplification fragment of about 350 bp was isolated on a 3% NuSieve 3:1 gel (FMC Biochemicals, Rockland, Me.) using NA-45 DEAE-cellulose paper (Schleicher and Scheull) (Sambrook et al., supra). The fragment was labeled with α$^{32}$P-dCTP (Amersham Corp., Arlington Heights, Ill.) by random priming (Random Priming kit, Boehringer-Mannheim, Indianapolis, Ind.), and used to screen 200,000 plaque-forming units (PFUs) of the human fetal eye library.

Eight positive clones were isolated (Sambrook et al., supra), and DNA of the positive clones was purified according to Qiagen Maxi preparation protocols (Qiagen, Inc., Chatsworth, Calif.). The inserts of the positive clones were cut out with Not I (BRL, Gaithersburg, Md.), circularized with T4 DNA ligase (New England Biolabs, Beverly, Mass.), transformed into *Escherichia coli* Epicurian Sure competent cells (Stratagene, Inc., La Jolla, Calif.), and plated onto Luria broth (LB) plates containing ampicillin and 5-bromo-4-chloro-3-indolyl-β-D-galactoside (X-gal).

White colonies were selected on the basis that such colonies should possess an insert, and plasmid DNA from single colony cultures were isolated by the Qiagen plasmid miniprep protocol. Purified plasmids were digested with EcoR I and Hind III (BRL). These restriction sites were added during library construction through the ligation of linkers to the 5' and 3' ends of the insert, thus EcoR I-Hind III digestion excises the insert present in isolated plasmids. These fragments were electrophoresed on a 0.7% agarose gel to determine insert size. The plasmid possessing the largest insert, namely πFS17, was selected for mapping and subsequent sequencing using the Sequenase 2.0 sequencing kit (United States Biochemical Corp., Cleveland, Ohio) to confirm the identity of the clone. Sequence analysis was performed using the MacVector software package (International Biotechnologies, Inc.) and the GenBank® Sequence Data Bank (Intelligenetics, Mountain View, Calif.).

Sequence analysis of πFS17 revealed a base sequence comprising SEQ ID NO:1, with a long, open reading frame (ORF) encoding the 418 amino acids of SEQ ID NO:2, a typical ATG start codon, and a polyadenylation signal (not shown in SEQ ID NO:1). The coding sequence of the clone aligns exactly with all previously determined PEDF peptide sequences. The deduced amino acid sequence also contains a stretch of hydrophobic amino acids that could serve as a signal peptide. A comparison of the coding sequence and peptide sequence with the GenBank® Data Bank indicates that PEDF is a unique protein having significant homology to the serpin (serine protease inhibitor) gene family, which includes human [α]-1-antitrypsin. Although some of the members of this gene family exhibit neurotrophic activity (Monard et al., *Prog. Brain Res.*, 58, 359–364 (1983); Monard, *TINS*, 11, 541–544 (1988)), PEDF lacks homology to the proposed consensus sequence for the serpin reactive domain.

EXAMPLE 3

This example describes the construction of an expression vector for the production of recombinant PEDF.

An expression vector was constructed using the plasmid πFS17, which contains the full-length cDNA for human PEDF as described in Example 2. The PEDF coding sequence was placed under the control of a bacteriophage lambda $P_L$ promoter present in the plasmid pEV-vrf2 (Crowl et al., *Gene*, 38, 31–38 (1985)) to obtain the vector pEV-BH. This was accomplished by obtaining a BamH I-Hind III fragment of πFS17 comprising a portion of the PEDF coding region (namely, nucleotide 245 to 1490 of SEQ ID NO:1), digesting plasmid pEV-vrf2 with EcoR I-Hind III, rendering both fragments blunt by means of a fill-in reaction at the BamH I and EcoR I ends with DNA polymerase I (Klenow fragment), and ligating the resultant blunt-ended/compatible-ended fragments to each other. The resultant vector pEV-BH places a distance of 8 nucleotide between the Shine-Dalgarno (SD) sequence and the PEDF coding region. The construct specifies Met-Asn-Arg-Lle-Asp$^{44}$ - - - Pro$^{418}$ such that a protein of 379 amino acids, known as rPEDF, is encoded as indicated in SEQ ID NO:3. The amino acids at the amino terminus of the rPEDF protein do not occur in native PEDF and result from the fusion of nucleic acids during the construction of PEV-BH.

To verify production of the recombinant PEDF protein by pEV-BH, the plasmid was propagated in *E. coli* strain RRI (Maniatis et al., *Molecular Cloning: A Laboratory Manual*, Cold Spring Harbor Laboratory, Cold Spring Harbor, NY (1982)), bearing the low copy-number compatible plasmid pRK248cIts that contains a gene for encoding a temperature-sensitive λcIAt2 repressor (Bernard et al., *Methods in Enzymology*, 68, 482–492 (1979)). Protein induction was performed as described in Becerra et al., *Biochem.*, 30, 11707–11719 (1991), with the following modifications. Bacterial cells containing pEV-BH were grown in LB medium containing 50 μg/ml ampicillin at 32° C. to early logarithmic phase, such that $OD_{600nm}$=0.2. The temperature of the culture was rapidly increased to 42° C. by incubating the flask in a 65° C. water bath, and the bacteria were subsequently grown at 42° C. for 2–3 hours in an air-flow incubator at 340 rpm. Aliquots were taken for absorbance readings at 600 nm.

Nascent proteins, synthesized following protein induction, were radiolabeled. After the temperature of the culture had reached 42° C., 150 μCi of L- [$^{35}$S]methionine (1040 Ci/mmol, Amersham Corp., Arlington Heights, Ill.) were added per ml of culture, and incubation was continued at 42° C. for 10 minutes and 30 minutes. Cells were harvested by centrifugation and washed with TEN buffer (10 mM Tris-HCl, pH 7.5, 1 mM EDTA, and 100 mM NaCl). $^{35}$S-labeled peptides from total bacterial extracts were resolved and analyzed on SDS-12% PAGE followed by fluorography. A band corresponding to a 42,820 $M_r$ polypeptide was detected 10 and 30 minutes post-induction. The size obtained for the recombinant protein expressed by pEV-BH matched the expected size for the coding sequence subcloned in PEV-BH. In a similar manner, smaller fragments (BP=28,000 $M_r$; BX =24,000 $M_r$; BA=9,000 $M_r$) can be synthesized and purified. BP peptide includes PEDF amino acids 44 through 269, BX peptide includes PEF amino acids 44 through 227, and BA peptide includes PEDF amino acids 44 through 121.

EXAMPLE 4

This example describes the construction of expression vectors containing the full-length PEDF cDNA.

In a manner similar to that described in Example 3 for the construction of PEV-BH, the PEDF ORF of plasmid πFS17 was placed under the control of the bacteriophage lambda PL promoter present in the plasmids pRC23 and pEV-vrf1 (Crowl et al. *Gene*, 38, 31–38 (1985)). This was accomplished by obtaining the SfaN I-Hind III fragment of πFS17 comprising a portion of the PEDF cDNA (namely, nucleotide 107 to 1490 of SEQ ID NO:1), digesting the plasmids with EcoR I-Hind III, rendering the fragments blunt by means of a fill-in reaction at the SfaN I and EcoR I ends with DNA polymerase I (Klenow fragment), and ligating the resultant blunt-ended/compatible-ended fragments to each other. The resulting vectors pRC-SH and PEV-SH place a distance of 14 and 8 nucleotide, respectively, between the SD sequence and the PEDF coding region. The construct pRC-SH encompasses the full-length PEDF ORF, and specifies a PEDF protein of 418 amino acids, with its naturally occurring amino terminus, as set forth in SEQ ID NO: 2. The construct pEV-SH encompasses the full-length PEDF ORF, and specifies a PEDF amino-terminal fusion protein of 425 amino acids, with Met-Asn-Glu-Leu-Gly-Pro-Arg (SEQ ID NO:8) preceding the PEDF sequence of SEQ ID NO:2. These additional amino acids at the amino terminus do not occur in native PEDF, and the codons in pEV-SH specifying these additional amino acids result from the fusion of nucleic acids during the construction of pEV-SH.

To verify production of the recombinant proteins specified by the two vectors, the vectors were introduced into *E. coli* strain RRI [pRK248cIts], and protein induction was performed and monitored by metabolic labeling with $^{35}$S-methionine during induction in a manner similar to that set forth in Example 3. The induced expression of the proteins specified by pRC-SH and pEV-SH had a negative effect on bacterial cell growth. In comparison with bacterial cultures containing the parental plasmids, cultures containing pRC-SH and pEV-SH grew and divided more slowly. This negative effect on bacterial growth correlated with the distance between the initiation codon and the SD, which may suggest that a shorter such distance results in more efficient translation of the recombinant protein. A 46,000 $M_r$ candidate polypeptide for PEDF was not detected in the media or cell lysates of bacterial cultures containing pRC-SH and pEV-SH. However, a 35,000 $M_r$ protein was observed in extracts of cultures containing pRC-SH and pEV-SH, but not in extracts of cultures containing parental plasmids. This may indicate that the amino-terminal end of PEDF is protease-sensitive and that recombinant full-length PEDF is metabolized in this particular host. Alternatively, failure to observe the anticipated-sized recombinant PEDF proteins may reflect an experimental artifact which could be overcome through the use of alternative expression vectors, hosts, inducible promoters, subcloning sites, methods of recombinant protein isolation or detection, or means of protein induction.

EXAMPLE 5

This example describes a method for producing large quantities of recombinantly produced PEDF.

A total of 1 g of E. coli cells containing rPEDF was resuspended in 50 ml 20 mM Tris-HCl, pH 7.5, 20% sucrose, and 1 mM EDTA. The cells were maintained on ice for 10 minutes, sedimented by centrifugation at 4000×g, and were resuspended in 50 ml of ice-cold water for 10 minutes. Lysed outer cell walls were separated from spheroplasts by centrifugation at 8000×g.

The pelleted spheroplasts were resuspended in 10 ml of phosphate buffered saline (PBS) containing 5 mM EDTA, 1 μg/ml pepstatin and 20 μg/ml aprotinin. The suspension was probe-sonicated with a sonicator (Ultrasonics, Inc., model W-225) to lyse the cell membranes. Three bursts at 30 second pulses with a 30 second pause were performed while the sample was immersed in an ice-water bath. RNase TI (1300 units, BRL) and DNase I (500 μg, BRL) were added to the sonicated cell suspension, and the suspension was incubated at room temperature for 10 minutes. This suspension was diluted by the addition of 40 ml of phosphate buffered saline (PBS) containing 5 mM EDTA, 1 μg/ml pepstatin and 20 μg/ml aprotinin, and the crude inclusion bodies were sedimented by centrifugation at 13,000×g for 30 minutes. The particulate material consisting of inclusion bodies was resuspended in 40 ml of PBS containing 25% sucrose, 5 mM EDTA, and 1% Triton X-100, incubated on ice for 10 minutes, and centrifuged at 24,000×g for 10 minutes. The washing step was repeated three times. Finally, the inclusion bodies were resuspended in 10 ml of denaturation buffer containing 50 mM Tris-Cl, pH 8.0, 5M guanidine-Cl, and 5 mM EDTA. The suspension was probe-sonicated briefly for 5 seconds in an ice-water bath. The resulting suspension was incubated on ice for an additional hour. After centrifugation at 12,000×g for 30 minutes, the supernatant was added to 100 ml of renaturation buffer containing 50 mM Tris-Cl, pH 8.0, 20% glycerol, 1 mM DTT, 1 μg/ml pepstatin, and 20 μg/ml aprotinin, and stirred gently at 4° C. overnight to renature the protein. The soluble and insoluble fractions were separated by centrifugation at 13,500×g for 30 minutes.

The soluble fraction was further purified by concentrating it to 1 ml using a Centricon 30 microconcentrator (Amicon Div., W. R. Grace & Co., Beverly, Mass.), and dialyzing it against Buffer A (50 mM sodium phosphate, 1 mM DTT, 20% glycerol, 1 mM EDTA, 1 μg/ml pepstatin, and 1 mM benzamidine) at 4° C. for 3 hours. The dialyzed extract was centrifuged at 14,000 rpm in an Eppendorf Centrifuge (Model 5415C) for ten minutes. The supernatant fraction was layered on a S-Sepharose fast-flow (Pharmacia, New Market, N.J.) column (1 ml bed volume) pre-equilibrated with buffer A. The column was washed with two column-volumes of buffer A. Finally, recombinant rPEDF was eluted with a step gradient of 50, 100, 150, 200, 300, 400, 500, and 1000 mM NaCl in buffer A. Fractions of 1 ml were collected by gravity flow, and were dialyzed against buffer A. Fraction 300, containing recombinant rPEDF, was stored at −20° C. The recovery in fraction 300 was 50 μg per gram of packed cells, which represents 25% of the total protein.

Most of the rPEDF was recovered from the insoluble fraction by dissolving the fraction in 10 ml of 6M guanidinium-Cl in buffer B (50 mM Tris-Cl, pH 8.0, 1 mM DTT, 2 mM EDTA). The solution was centrifuged at 10,000×g for 5 minutes. The supernatant was layered onto a Superose-12 (Pharmacia, New Market, N.J.) column attached in tandem to a second Superose-12 column (each column 2.6 cm ×95 cm) pre-equilibrated with buffer containing 4M guanidinium-Cl in buffer B. The flow rate was 3 ml/minute. Recombinant rPEDF containing fractions from the Superose-12 column were pooled and dialyzed against buffer C (4 M urea, 50 mM sodium phosphate, pH 6.5, 1 mM benzamidine, 1 μg/ml pepstatin, 4 mM EDTA). The dialyzed fraction was passed through a 0.22 μm filter (Miller-GV, Millipore Corp., Bedford, Mass.). The filtered solution was layered onto a mono-S (Pharmacia, New Market, N.J.) column (1 cm×10 cm, d×h) pre-equilibrated with buffer C. The column was washed with buffer C, and recombinant rPEDF was eluted with a gradient of 0 mM–500 mM NaCl in buffer C at 0.5 ml/min. Two-ml fractions were collected, and the peak fractions of recombinant rPEDF were pooled. The recovery in the pooled fractions was 0.5 mg of recombinant PEDF per gram of packed cells.

EXAMPLE 6

This example describes the use of purified recombinant PEDF as a differentiation agent.

Y79 cells (ATCC, HTB18) were grown in Eagle's Minimal Essential Medium with Earl's salts (MEM) supplemented with 15% fetal bovine serum and antibiotics (10,000 u/ml penicillin and 10 mg/ml streptomycin) at 37° C. in a humidified incubator under 5% $CO_2$. Cells were propagated for two passages after receipt from the ATCC, and then frozen in the same medium containing 10% DMSO. A few of the frozen aliquots were used for each differentiation experiment. All experiments were performed in duplicate.

After thawing, the cells were kept, without further passaging, in the serum-containing medium until the appropriate number of cells were available. Cells were collected by centrifugation and washed twofold in PBS, resuspended in PBS, and counted. At that point, $2.5 \times 10^5$ cells were plated into each well of a 6-well plate (Nunc, Inc., Roskilde, Denmark) with 2 ml of serum-free medium (MEM, supplemented with 1 mM sodium pyruvate, 10 mM HEPES, 1× non-essential amino acids, 1 mM L-glutamine, 0.1% ITS mix (5 μg/ml insulin, 5 μg/ml transferrin, 5 ng/ml selenium, Collaborative Research, Bedford, Mass.), and antibiotics as described above.

Differentiation effectors and control buffers were added 12–16 hours after plating, and the cultures were incubated and left undisturbed for 7 days. On the eighth day, cells were transferred to poly-D-lysine-coated six-well plates (Collaborative Research, Bedford, Mass.), and the old medium was replaced with 2 ml of fresh serum-free medium, upon attachment of the cells to the substrate. The cultures were maintained under these conditions for up to 11 days. Post-attachment cultures were examined daily for morphological evidence of differentiation as well as quantification of neurite outgrowth using an Olympus CK2 phase-contrast microscope.

Figure 22A:
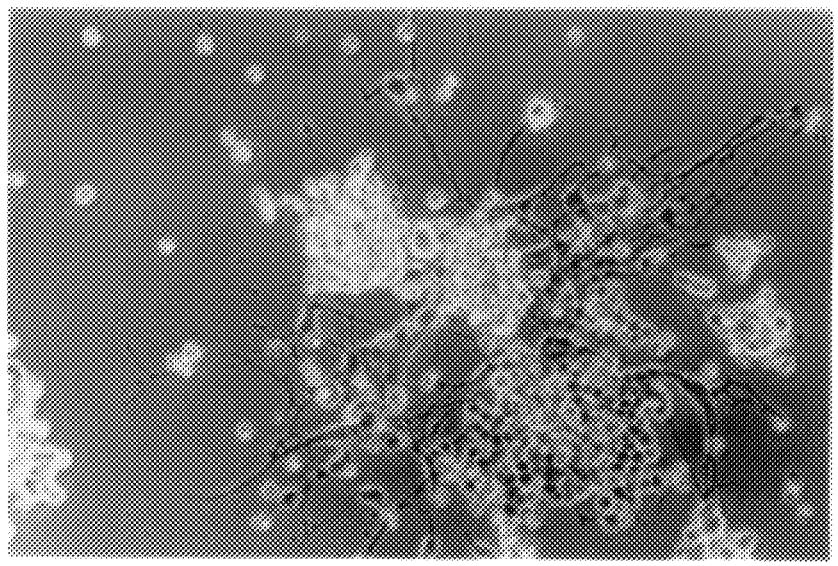
Figure 22B:
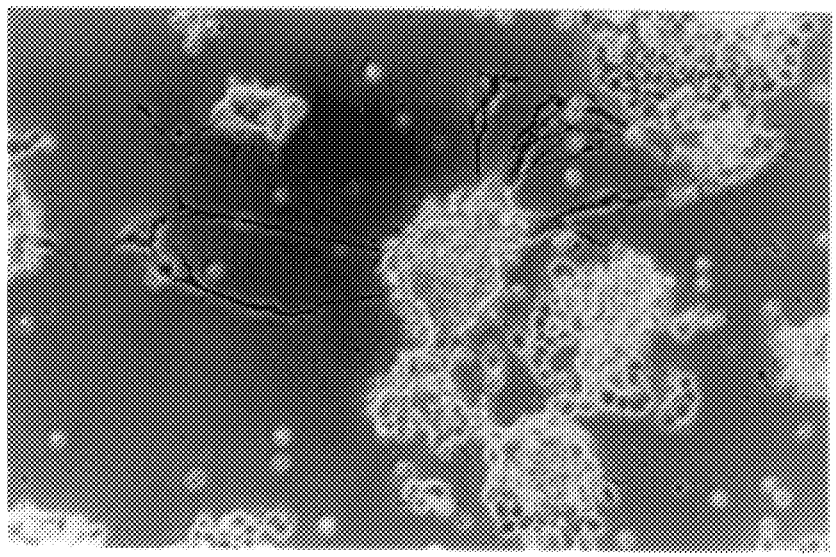
Figure 23:
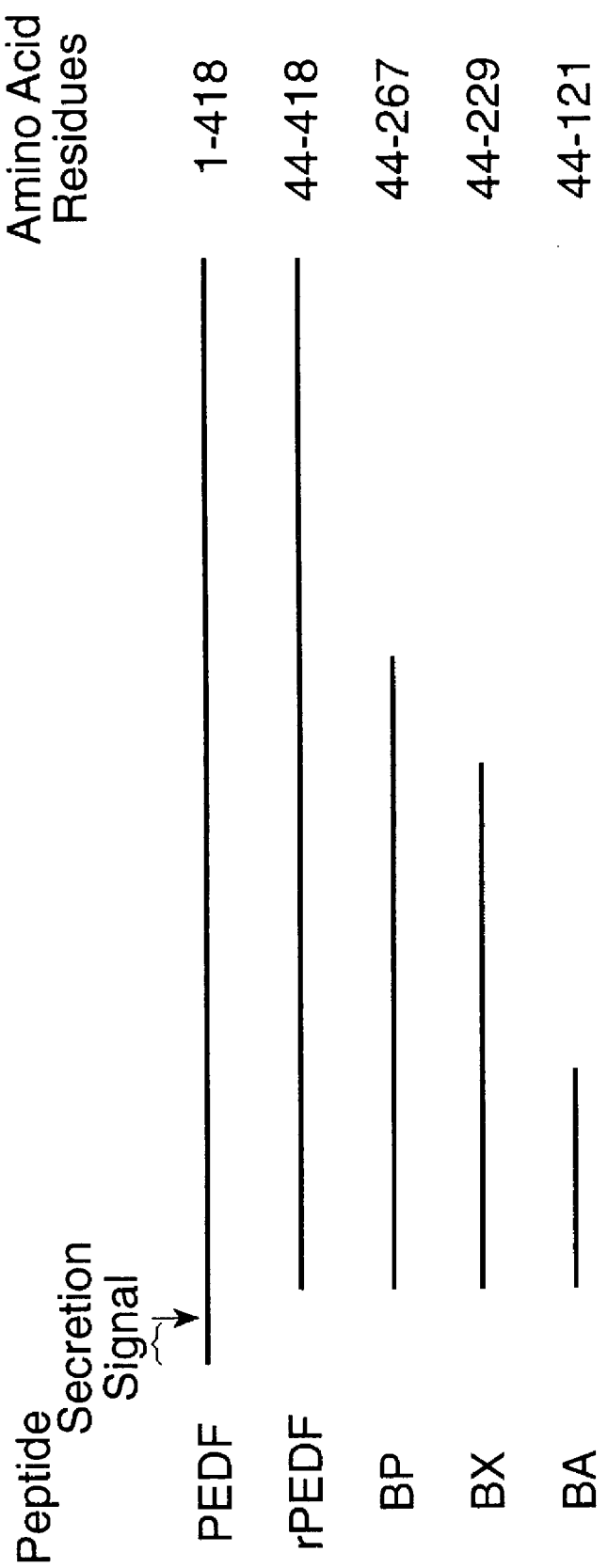

In comparison with untreated cells, only Y79 cultures that were exposed to recombinant rPEDF showed any significant evidence of neuronal differentiation. Some neurite outgrowth (below 5%) was detectable in control cultures treated with the same buffer used to solubilize rPEDF, and no evidence of differentiation was found in cultures processed in the same manner without the addition of rPEDF or buffer (FIG. 22A, "control"). Phase contrast microscopy of rPEDF treated cultures showed that between 50–65% of the cell aggregates had neurite extensions by day 3 post-attachment on poly-D-lysine (FIG. 22B, "PEDFII"). These 3-day neurite extensions appeared as short projections from pear-shaped cells at the edges of the cell aggregates. The number of differentiating aggregates, the number of differentiating cells per aggregate, and the length of the neurite-like processes increased with post-attachment time. By day 5 post-attachment, about 75–85% of the aggregates showed signs of differentiation with neurites extending from most of their peripheral cells. rPEDF-treated cultures reached the maximum extent of differentiation on day 7 post-attachment, when 85–95% of the cells aggregate. At that time, two types of neuronal processes were observed, i.e., single neurites 2–3 fold longer than those observed on day 3 extending from peripheral cells of isolated aggregates, and much longer and thinner processes forming a branching network between neighbor cell aggregates. Upon extended incubation, i.e., beyond 10 days post-attachment, there was a marked decrease in the proportion of the network connections, and no further growth of the single neurites, although the viability of the cell aggregates was not severely affected, and remained at about 75–80% in different experiments. No differences were observed between purified native PEDF and recombinant PEDF (rPEDF) as seen in FIG. 23.

The PEDF and rPEDF cDNA clones not only provide means to produce large quantities of the PEDF and rPEDF proteins but also serve as sources for probes that can be used to study the expression and regulation of the PEDF gene. In addition, these sequences can be used in the antisense technique of translation arrest to inhibit the translation of endogenous PEDF.

The recombinantly produced PEDF and rPEDF proteins and equivalent proteins can be used as potent neurotrophic agents in vitro and in vivo. Additional biochemical activities of these proteins as neurotrophic agents can be determined through standard in vitro tests, which will enable the development of other therapeutic uses for these proteins in the treatment of inflammatory, vascular, degenerative and dystrophic diseases of the retina. Given that these proteins are such potent neurotrophic agents, it can be envisioned that these proteins could be modified for therapeutic utility in the treatment of tissues other than the retina, which also respond to neurotrophic factors. These proteins may even find more generic utility as "differentiation" factors for non-neural tissues and certain types of cancer.

EXAMPLE 7

Along with the 3,000 mol. wt. recombinant PEDF, smaller recombinant constructs have been synthesized to determine if they have neurotrophic activity. Smaller peptides could offer a variety of advantages over the full-length construct such as greater solubility, better membrane penetration, less antigenicity, greater ease in preparation, etc.

Figure 21A:
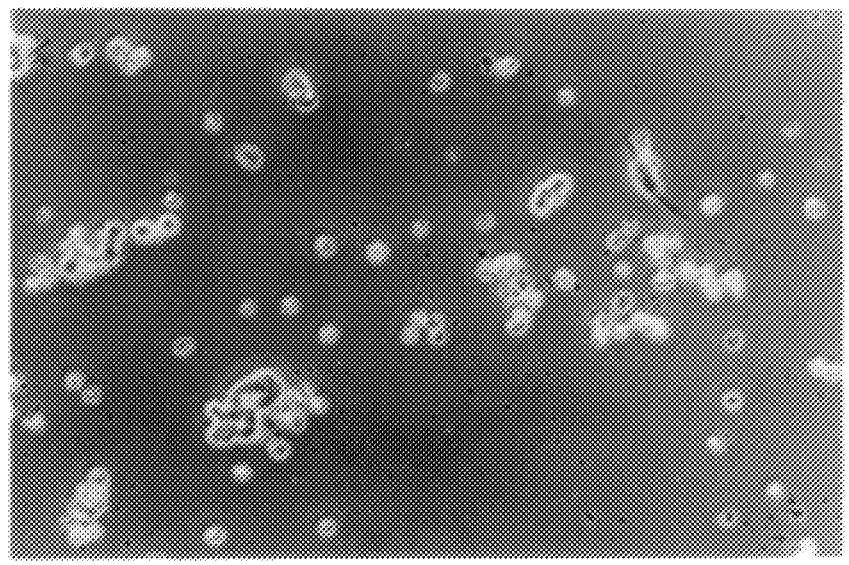
Figure 21B:
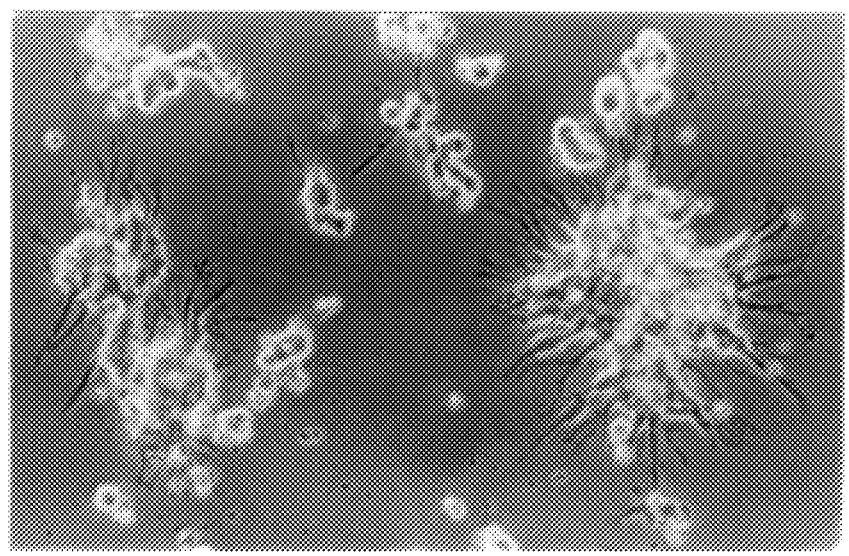

FIG. 23 shows only three of the constructs that have been tested. BP, BX and BA are about 28,000, 24,000 and 9,000 mol. wts. respectively and represent C-terminal deletion mutants. All of these show neurotrophic activity similar to that depicted in FIGS. 21A and B and 22A and B. The novel finding here is that even the 9,000 m.w. peptide (only about 20% of the full m.w. of the native protein) exhibits striking neurotrophic activity. Moreover, the active neurotrophic peptide represents sequences at the N-terminal rather than at the C-terminal which is known to contain the serpin active site. Thus, that the active site is at the N-terminal and activity can be elicited with such a small molecule are surprising findings that could not have been predicted based on any previous findings.

EXAMPLE 8

The Cloning Of Genomic PEDF DNA
Isolation of genomic clones
(a) Screening genomic libraries
Lambda gt 11 plasmid containing a 1.5 kb PEDF CDNA insert was digested with Eco R1 and Hind III (BRL) and insert obtained by gel purification. 25 ng of the purified PEDF cDNA insert was labelled with α-$^{32}$P dCTP (Amersham) by random priming (Random Prime It kit from Stratagene). Unincorporated nucleotide were removed by Stratagene's Nuc trap push columns. This probe was used to screen two genomic DNA libraries: a cosmid library constructed from Mbo I partial digests of human placental DNA (Clonetech) and a human placental genomic library constructed in XDASH II (Stratagene) genomic. Positively hybridizing clones were isolated by standard methods (Troen 1987 *Methods in Enzymology*, 151:416–426 and the DNA purified with Qiagen maxi preparation protocols (Qiagen, Chatsworth, Calif.). Southern blotting analysis of the purified clones revealed the presence of two strongly hybridizing fragments: a 7.1 kb Bam HI fragment (jt101) from the cosmid clone and a 7.2 kb Not 1 fragment (jt106) from the λDASH II clone. These were selected for subcloning in Bluescript and DNA sequencing.

(b) Cloning by PCR

Four sets of primers, 603:604; 605:606; 2238:354 and 2213:2744 designed from the internal coding regions of the PEDF cDNA sequenced were synthesized using an ABI 392 DNA/RNA synthesizer for use as primers in a polymerase chain reaction (PCR) experiment. The primer sequences are as follows: 603: 5'-ACA AGC TGG CAG CGG CTG TC-3' (SEQ ID NO: 13), 604: 5'-CAG AGG TGC CAC AAA GCT GG-3' (SEQ ID NO: 14); 605: 5'-CCA GCT TTG TGG CAC CTC TG-3' (SEQ ID NO: 15), 606: 5'-CAT CAT GGG GAC CCT CAC GG-3' (SEQ ID NO: 16), 2213: 5'-AGG ATG CAG GCC CTG GTG CT-3' (SEQ ID NO: 17), 2744: 5' CCT CCT CCA CCA GCG CCC CT-3' (SEQ ID NO: 18); 2238: 5'-ATG ATG TCG GAC CCT AAG GCT GTT-3' (SEQ ID NO: 19), 354: 5'-TGG GGA CAG TGA GGA CCG CC-3' (SEQ ID NO: 20). Standard reagents (GeneAMP, Perkin-Elmer/Cetus, Norwalk, Conn.) and 25 ng of human genomic DNA obtained from the P1–11. PCR reactions were carried out at a number of different annealing temperatures until only single amplified products were obtained. The primer pairs 603:604 amplified a single 2 kb PCR product (jt108); 605:606 a single 3.3 kb PCR product (jt 109); 2213–2744 amplified a single 2.3 kb PCR product (jt 115) and 2238:354 a single 1.5 kb PCR product (jt 116).

(c) P1 clones

Two primer pairs JT10-UPO1:JT10-DPO1 corresponding to bases 6536–6559 of jt106 genomic sequence and 1590:1591 corresponding to bases 1–89 on the PEDF cDNA sequence were used in PCR reactions to isolate P1 clones (Genome Systems). The primer sequences are as follows; JT10-UP01: 5'- GGT GTG CAA ATG TGT GCG CCT TAG-3' (SEQ ID NO: 21); JT10-DP01: 5'-GGG AGC TGC TTT ACC TGT GGA TAC-3' (SEQ ID NO: 22); 1590: 5'-GGA CGC TGG ATT AGA AGG CAG CAA A-3' (SEQ ID NO: 23); and 1591: 5'-CCA CAC CCA GCC TAG TCC C-3' (SEQ ID NO: 24). Several positive clones were isolated by PCR and two of these designated P1–11 and PI-47 were subjected to southern blotting analysis and PCR assays to confirm the presence of the entire PEDF gene and splice junctions. Primer pairs encompassing contiguous stretches of the PEDF cDNA sequence were used to amplify products from PI-11 The primers were as follows: 601–1591 (bases 1–89) 2213–2744 (bases 114–243); 603:604 (bases 271–590); 605–606 (bases 571–848); 2238–354 (bases 843–1062) and 356:499 (bases 1034–1472). The products obtained were 89 bp, 2.3 kb, 2 kb, 3.3 kb, 1.5 kb and 900 bp respectively. The products were sequenced with an automated fluorescence sequencer to confirm splice junctions of the PEDF gene from sequences obtained from non-PI clones.

EXAMPLE 9

Sequence Analysis Of The Cloned Genomic DNA Fragments

DNA Sequencing (a) Dideoxynucleotide termination method jt101 and jt106 were gel purified and subcloned into the Bam HI and Not I sites respectively, of pBluescript II SK+ vectors (Stratagene). These were used to transform XL-I Blue competent cells (Stratagene). Transformants were isolated and subcloned. The clones were blunt ended using T4 DNA polymerase, gel purified and subcloned into the Eco RV site of pBluescript II SK-(Stratagene) and used to transform XL-I blue cells. Nested deletions were generated from both the T7 and T3 ends of the subclones using Exo III and SI nuclease (Lark Sequencing Co.). Plasmid DNA was prepared using a modified alkaline lysis procedure and deletion clones size selected for DNA sequencing by electrophoresis on agarose gels. DNA sequencing (Lark Sequencing Co.) was performed using standard dideoxynucleotide termination method and sequencing reactions analyzed on 6% polyacrylamide wedge gels containing 8M urea.

jt108, jt109, jt115 and jt116 (PCR products) were cloned into the modified Eco RV site of the PT7 Blue vector (Novagen). These were subsequently used to transform Nova Blue cells (Novagen) such that both orientations of the insert into the vector were obtained. Nested deletions were then generated from the reverse end minilysates using Exo III and SI nuclease and sequenced as above.

(b) Fluorescent automated DNA sequencing

Fluorescent sequencing was performed using an ABI model 370A instrument connected to an Apple MacIntosh ci and ABI's 373 A sequencing software. The sequencing was performed using ABI's Taq DyeDeoxy Terminator cycle sequencing kit following the manufacture's protocol. In general 0.5 pmoles of template obtained form PCR products of the P1–10$^1$ clone and 3 pmoles of primer were used per sequencing reaction. All other details are provided in the ABI's manual included in the sequencing kit.

(c) RACE

For RACE, (Frohman, 1990 *PCR Protocols: A guide to Methods and Applications,* 1st ed. p. 28–38 Academic Press, San Diego, Calif.) experiments 1.0 ug of total human retina was dried down with 20 nanogram of primer 1590, GGA CGC TGG ATT AGA AGG CAG CAA A, complementary to position +1 and +25 in the gene sequence. Reverse transcriptase, reaction buffer and dNTP solution (BRL) were added to a final volume of 20 ul. The reaction was carried out at 42° C. for 30 min followed by a 5 min incubation at 55° C. Templates were tailed with poly (A) using terminal deoxytransferase (BRL). Sequences corresponding to the 5' end of MRNA were then amplified by PCR using a specific primer representing cDNA sequence between nucleotides 223–243, CCT CCT CCA GCG CCC CT, and oligo (dt). The product obtained from the PCR reaction were sequenced directly using and ABI automated fluorescent sequencer.

The seven clones isolated either from genomic libraries or by PCR-mediated cloning were sequenced and used to characterize the exon structure of the PEDF gene and to define the intron/exon junction sequences. The conventional method of cloning was replaced by PCR-mediated cloning because of instability and rearrangement of the gene in both cosmid and lambda genomic libraries.

Two positively hybridizing clones, jt101 of 7.1 kb long and jt106 of 7.2 kb long were isolated from a cosmid and λDASH II genomic libraries respectively. Four clones of length 2 kb (jt108), 3.3 kb (jt109), 2.3 kb (jt115) and 1.5 (kb) (jt116) represented PCR products of human genomic DNA. lr117 clone was obtained from an exon 1-labelled positively hybridizing Bam HI fragment form human genomic and P147 DNA. Two P1 clones, P1–11 and P1–47 containing the entire PEDF gene were also isolated and splice junctions sequenced.

jt101: Sequence analysis of this 7.1 kb Bam HI fragment contained the most 3' end of the PEDF gene. The clone contained exon 7 (bases 903–1113 of the cDNA) and exon 8 (bases 1114–1503 of the cDNA) of 211 bp and 377 bp respectively. Intron 6 and intron 7 were also sequenced from this clone. Intron 7 was intact and is 444 bp in length while intron 6 was found to be somewhat rearranged (FIG. 1)

jt106: Sequence analysis of this 7.2 kb Not I fragment indicated only sequences present in the most 5' end of the PEDF gene. This clone contained the promoter of the PEDF gene as well as exon 1 of 109 bp (bases 1–109 of the cDNA) and an incomplete intron 1 of 535 bp. We were unable to obtain specific PCR amplification products for this intron from either total human genomic DNA or the PI clones suggesting that the size of the first intron was rather enormous (FIG. 1).

jt108: The PCR clone JT108 containing a 2 kb PCR product amplified using primer 603:604 contains most of exon 3 and exon 4. Intron 3 and intron 4 of 980 bp and 689 bp respectively were sequenced from this clone (FIG. 1).

jt109: This 3.3 kb clone representing PCR product obtained with primers 605:606 contains most of exon 5 and exon 6. The clone also contains the 3 kb intron 5 (FIG. 1).

jt115: The 2.3 kb clone JT115 obtained from the PCR product amplified using the primer pair 2213:2744 contained exon 2 and intron 2 which is 2.2 kb in length (FIG. 1).

P1–11: More recently we have sequenced the intron-exon boundaries of the PEDF gene in the P1–11 clone using primers designed from exon sequences flanking each intron. Approximately 200 bp on either side of the junctions were sequenced and these align perfectly with the sequence obtained from the above clones. All splice junctions sequences were confirmed as well as the sizes of introns and exons. From this clone (P1–11), intron no. 2 (JT115) was obtained. The sequences from P1–11 showed that this P1 clone contained the entire PEDF gene.

Thus from the sequence analysis of all the above clones the structure and size of exons and introns of the human PEDF gene were determined. Exon/intron junctions were established by comparing genomic and cDNA sequence of PEDF and by identifying consensus splicing sites (Senapathy et. al., 1990 *Methods in Enzymology,* 183:252). The analysis indicates that the human PEDF gene is approximately 16 kb in length and is composed of 8 exons ranging in size from 92 nt to 377 nt and 7 introns ranging from 0.4 kb to 6 kb (Table 1). The 5' splice donor and 3' splice acceptor sites in all junctions conform to the GT/AG consensus. Exons are distinguished unevenly throughout the gene and the largest intron of 6 kb long is located between exon 1 and exon 2. No significant patterns were seen in the spatial organization of exons, in the distribution of introns or in the occupance of certain types of splice junctions to infer a unique evolutionary relationship among any subset of exons.

TABLE 1

Exon and Intron Organization of the human PEDF Gene

| Exon Number | Exon Size (bp.) | 5' Splice Donor | SEQ. ID. NO. | Intron size (Kb) |
|---|---|---|---|---|
| 1 | 98 | TATCCACAG/gtaaagtag ... | 25 | >6 Kb |
| 2 | 92 | CCGGAGGAG/gtcagtagg ... | 26 | 2.3 Kb |
| 3 | 199 | TCTCGCTGG/gtgagtgct ... | 27 | 1.0 Kb |
| 4 | 156 | TTGAGAAGA/gtgagtcgc ... | 28 | 0.7 KB |
| 5 | 204 | ACTTCAAGG/gtgagcgcg ... | 29 | 3.0 Kb |
| 6 | 143 | AGCTGCAAG/gtctgtggg ... | 30 | 1.3 Kb |
| 7 | 211 | AGGAGATGA/gtatgtctg ... | 31 | 0.4 Kb |
| 8 | 377 | TTTATCCCT/aacttctgt ... | 32 | |

| 3' Splice Acceptor | SEQ. ID. NO. | Intron No. |
|---|---|---|
| GGACGCTGG | 33 | 1 |
| ... ttcttgcag/GCCCCAGGA | 34 | 2 |
| ... tcctgccag/GGCTCCCCA | 35 | 3 |
| ... ctctggcag/GAGCGGACG | 36 | 4 |
| ... tcttctcag/AGCTGCGCA | 37 | 5 |
| ... tcttttccag/GGCAGTGGG | 38 | 6 |
| ... ttgtctcag/ATTGCCCAG | 39 | 7 |
| ... tctctacag/AGCTGCAAT | 40 | 8 |

Table 1: Exons are in upper case and introns sequences lower case. The 5' donor GT and 3' acceptor AG are underlined. Exon and intron sizes are given in bp and kb respectively.

EXAMPLE 10

Expression of PEDF MRNA in Cultured Cells
Gene expression analysis

Multiple human tissue mRNA Northern blots (Clonetech) with 2 ug Poly-(A) RNA per lane were hybridize with a radioactively-labelled 667 bp PCR amplified PEDF product (Tombran-Tink et al., 1994 *Genomics*, 19:266–272). Blots were prehybridized for 15 min at 68° C. in QuickHyb rapid hybridization solution (Stratagene, La Jolla, Calif.) and hybridized for 1 hr at 68° C. in the same solution containing $5 \times 10^6$ cpm DNA/ml. Hybridized blots were washed twice with 100 ml of 2×SSC, 0.1% SDS for 15 min at room temperature and once with 200 ml of 0.1×SSC, 0.1% SDS for 30 min at 68° C. The blots were autoradiographed at −70° C. for 2 hr using Kodax XAR-5 film and DuPont intensifying screens. Gene Expression:

In order to determine whether expression of the PEDF messenger RNA occurs in human tissues other than in cultured human fetal RPE cells, we analyzed multiple tissue human adult and fetal RNA blots containing equal amounts of poly-(A) RNA for each tissue examined. The results are shown in FIG. 4A, B, and C. The PEDF probe identified a single primer 1.5 kb transcript of varying intensity of hybridization in 14 of the 16 adult tissue analyzed. No signal is detected in either adult kidney or peripheral blood leucocytes. Only a weak signal can be observed in adult brain, pancreas, spleen and thymus. The greatest amount of hybridization for PEDF messenger RNA is seen in human adult liver, skeletal muscle, testis and ovary. Surprisingly, only a very weak signal is observed in total brain RNA. In the fetal tissues examined, a very strong PEDF signal is seen in liver tissue, and interestingly a signal of significant intensity in fetal kidney as compared to no PEDF hybridization in adult kidney samples.

In contrast to the single 1.5 kb transcript observed in the adult tissues, an additional minor transcript of less than 500 bp is labelled variably and with lower intensity in fetal heart, lung and kidney. This may be due to partial degradation of the message or an alternative splicing phenomenon. PEDF is also only expressed in early passaged monkey RPE cells (1st–5th passage) and not in late passaged cells (10th passage). These data demonstrate the relevance of PEDF to senescence.

EXAMPLE 11

Figure 5A:
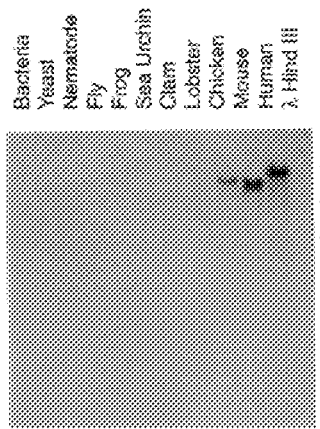
Figure 5B:
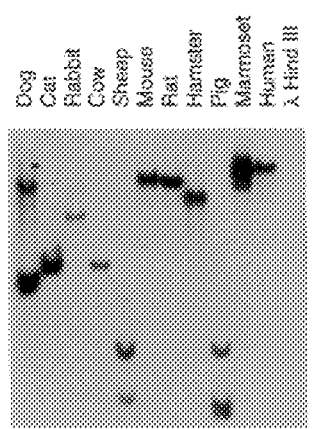
Figure 5C:
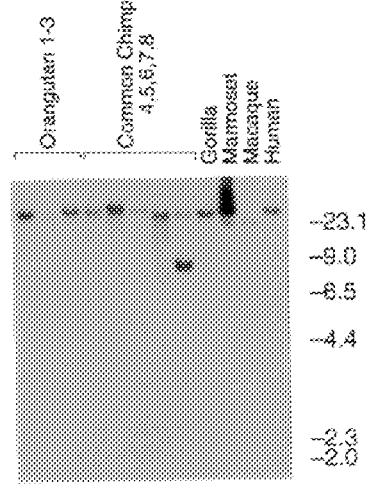

Comparative Analysis Of PEDF In A Variety Of Phylogenetically Related Species
Evolutionary conservation analysis 8 ug of genomic DNA from lymphocytes of a variety of species including a number of mammalian and primate species (BIOS laboratories, New Haven Conn.) was digested with Eco-R1 and separated in 1% agarose gels. The gels were transblotted and membranes containing the digested DNA hybridized using the same procedure and conditions as that for Northern analysis. Evolutionary conservation:

The evolutionary conservation of PEDF among a number of phylogenetically related species was examined. The results are presented in FIG. 5A, B, and C. Using these high stringency hybridization conditions, a large EcoRI restriction fragment of approximately 23 kb is observed in aves, mammals and primates. No hybridization signals were seen in lower species (FIG. 5A) possible due to weak homology of the human PEDF probe used. The EcoRI fragment for both chicken and mouse is somewhat smaller than that for humans. An interesting restriction pattern emerges in several of the mammalian species examined (FIG. 5B). Several smaller restriction fragments ranging in size between 6 kb and 2 kb are seen. The larger fragments range in size between 9 kb and 23 kb and are seen in all primates species examined which has an additional strongly hybridizing polymorphic fragment at approximately 9 kb.

EXAMPLE 12

Neuronotrophic Effects of Pigment Epithelium Derived Factor On Cerebellar Granule Cells In Culture Cell Culture Cerebellar granule cells (CGC) were prepared from 5 or 8-day-old Sprague-Dawley rat pups as described by Novelli et al. (1988, *Brain Res.*, 451:205–212). In brief, tissue free of meninges was minced in a buffer containing 124 mM NaCl, 1 mM $NaH_2PO_4$, 1.2 mM $MgSO_4$, 3 mg/ml bovine serum albumin (BSA), 27 $\mu$M phenol red, and 25 mM HEPES (pH 7.4), and centrifuged at 550 ×g for 3 min. The tissue pellet from 10–20 animals was resuspended and trypsinized (15 min, 37° C.) in 30 ml of the same buffer containing 250 $\mu$g/ml trypsin; a further 15 ml of buffer was added containing 26 $\mu$g/ml DNase I, 166 ug/ml soybean trypsin inhibitor, and 0.5 mM additional $MgSO_4$ and the tissue was centrifuged again as described above. The pellet was resuspended in 1 ml of buffer supplemented with 80 $\mu$g/ml DNase, 0.52 mg/ml of trypsin inhibitor, and 1.6 mM additional $MgSO_4$, and triturated 60 times with a Pasteur pipette. The suspension was diluted with 2 ml of buffer containing 0.1 mM $CaCl_2$ and 1.3 mM additional $MgSO_4$, and undissociated material allowed to settle for 5 min. The supernatant was transferred to another tube, cells were recovered by brief centrifugation and resuspended in serum-containing medium (Eagle's basal medium with 25 mM KCl, 2 mM glutamine, 100 $\mu$g/ml gentamycin, and 10% heat inactivated fetal calf serum) or chemically defined medium (DMEM:F 12 (1:1) with 5 $\mu$g/ml insulin, 30 nM selenium, 100 $\mu$g/ml transferrin, 1000 nM putrescine, 20 nM progesterone, 50 U/ml penicillin, 50 μg/ml streptomycin, and 2 mM glutamine) (Bottenstein, 1985 *Cell Culture in the Neurosciences*, J. E. Bottenstein and G. Sato, eds. New York Plenum Publishing Corp. p. 3–43). Cells were plated in poly-L-lysine-coated 96 well plates (for MTS assay and neurofilament ELISA assay) or 8-well chamber slides (for immunocytochemistry and BrdU labelling) at $2.5 \times 10^5$ cells/$cm^2$ and grown at 37° C. in an atmosphere consisting of 5% $CO_2$ in air. After 1 day in culture, cytosine arabinoside (Ara-C) was added only to cells in serum-supplemented medium (final concentration 50 μM).

MTS Assay

Cerebellar granule cells in 96 well plates were incubated in a $CO_2$ incubator for 4 hours with MTS (3-(4,5-dimethylthiazol-2-yl)-5-(3-carboxymethoxyphenyl)-2-(4-sulfophenyl)-2H-tetrazolium, inner salt) and PMS (phenazine methosulfate) final concentration; 333 μg/ml MTS and 25 μM PMS) (Promega Corp.). In the presence of PMS, MTS is converted to a water-soluble formazan by a dehydrogenase enzyme found in metabolically active cells (Cory et al., 1991 *Cancer Comm*, 3:207–212). The quantity of formazan product was determined by spectrophotometry at 490 nm.

Immunocytochemistry

After 7 days in vitro (DIV), the cells were washed three times in calcium-and magnesium-free phosphate-buffered saline (PBS) and fixed with 2% paraformaldehyde for 10 min, followed by 10 min at -20° C. in 95% ethanol/5% acetic acid. Incubation with primary antibodies against NSE (neuron specific enolase), GABA, calbindin, or glial fibrillary acidic protein (GFAP) was carried out for 60 min at RT. Antibodies were applied at 1:1000–1:5000 in the presence of 2% normal goat serum and 0.2% BSA. The antibodies were visualized using the ABC system (Vector Laboratories) and diaminobenzidine. At least 20 fields were counted from 2–3 wells for each experiment. The average number of cells per field was then calculated to determine the ratio for the number of cells stained by the other antibodies relative to NSE-positive cells in control cultures.

Bromodeoxyridine (BrdU) Labeling

BrdU labeling was performed by the method of Gao et al. (1991 *Neuron*, 6: 705–715) with the following modification. The cells were plated in 8-well chamber slides and rPEDF added immediately. After 24 hours, BrdU (1:100; Amersham cell proliferation kit) was added to the culture medium for 24 hours, after which the cells were fixed in 2% paraformaldehyde (10 min), treated with 95% ethanol / 5 acetic acid (10 min), and incubated with an anti-BrdU monoclonal antibody (1:20 for 2 hrs). The cultures were then incubated with a horseradish peroxidase-conjugated goat anti-mouse secondary antibody for 60 min. After diaminobenzidine-peroxidase, the cells were mounted in Gel Mount. The mitotic index was determined by counting the percentage of labeled cells with a microscopy. For each value, a random sample of 3000 cells was counted.

Neurofilament ELISA Assay

The neurofilament ELISA was performed according to the method of Doherty et al. (1984 *J. Neurochem.*, 42:1116–1122) with slight modification. Cultures grown in 96-well microtiter plates were fixed with 4% paraformaldehyde in PBS at 4° C. for 2 hr. The fixed cells were permeabilized by treatment for 15 min with 0.1% Triton X-100 in PBS, followed by incubation for 60 min with PBS containing 10% goat serum to block nonspecific binding. The cultures were then incubated with a monoclonal anti-neurofilament antibody overnight at 4° C. (RMO-42 at 1:100; which stains only neurites in the cultures of cerebellar granule cells). After washing twice with PBS containing 10% goat serum, cells were incubated with secondary antibody (horseradish peroxidase-conjugated goat anti-mouse at 1:1000) for 1 hr. Following sequential washing with PBS and water, the cultures were incubated with 0.2% O-phenylenediamine and 0.02% $H_2O_2$ in 50 mM citrate buffer (pH 5.0) for 30 min. The reaction was stopped by adding an equal volume of 4.5M $H_2SO_4$. Product formation was quantitated by reading the optical density (O.D.) of an aliquot of the reaction product at 490 nm using a microplate reader.

Figure 6A:
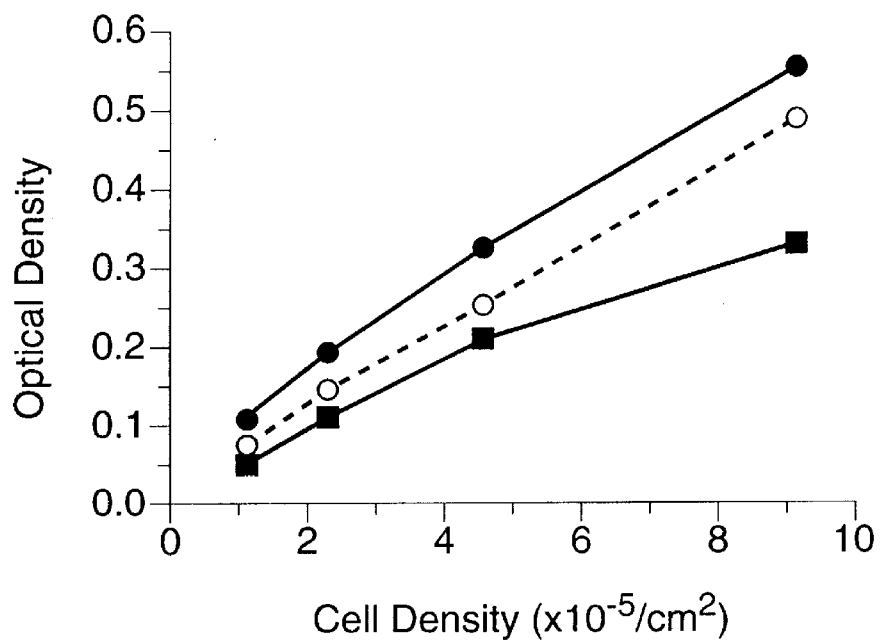
Figure 6B:
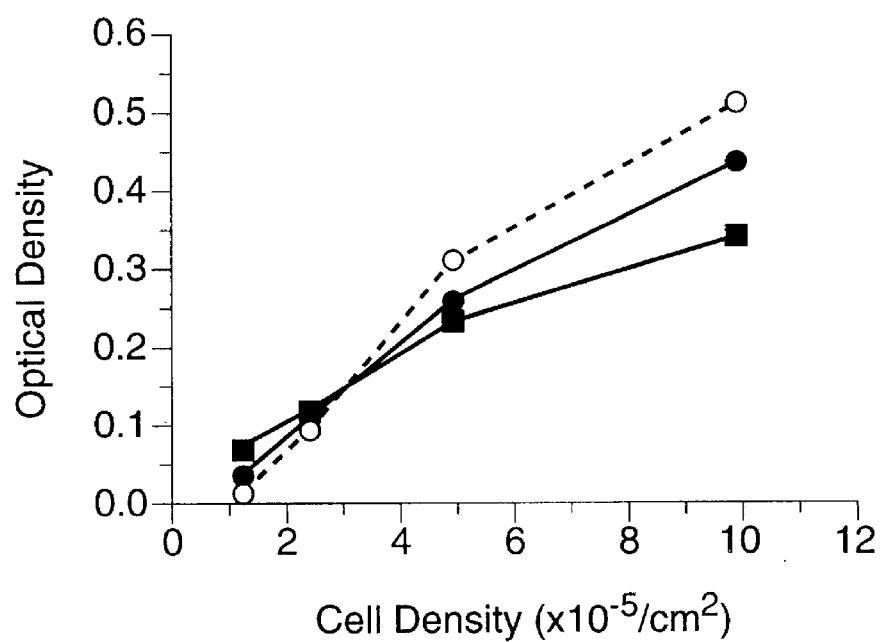

In order to validate the MTS assay as a measure of live cells, and to determine the range of cell number over which the results would be linear, the experiments shown in FIG. 6 were carried out. In serum-containing medium (SCM) (FIG. 6A), optical density (O.D.) was proportional to cell number plated over a range from $1-9 \times 10^5$ cells/$cm^2$. In contrast, for cells grown in chemically-defined medium (CDM) (FIG. 6B), the linear range covered $1-5 \times 10^5$ cells/$cm^2$. For all subsequent experiments, cells were plated at $2.5 \times 10^5$ cells/$cm^2$, in the middle of the linear range for either type of culture medium.

Figure 7:
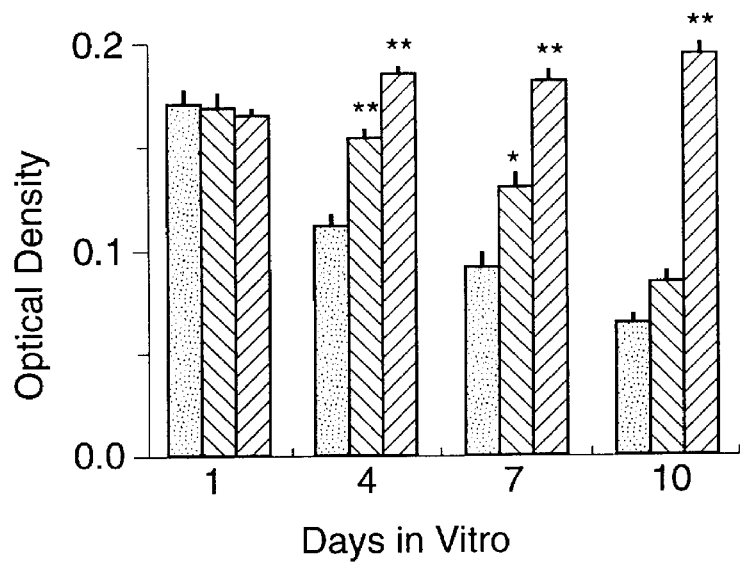
Figure 8:
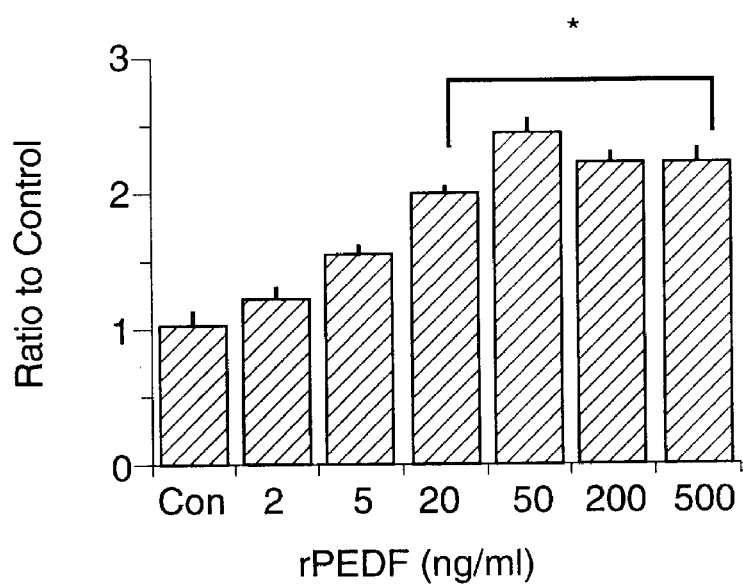

FIG. 7 shows that PEDF caused a significant increase in cell number by DIV4 with a larger difference at DIV7 and 10. However, the 2–3 fold increases were the result of large decreases in cell numbers in the control cultures. The dose-response curve in chemically-defined medium (FIG. 8), showed that there is a statistically significant effect at 20 ng/ml. Increasing the concentration of PEDF above 50 ng/ml did not produce further increases in CDM.

Figure 9:
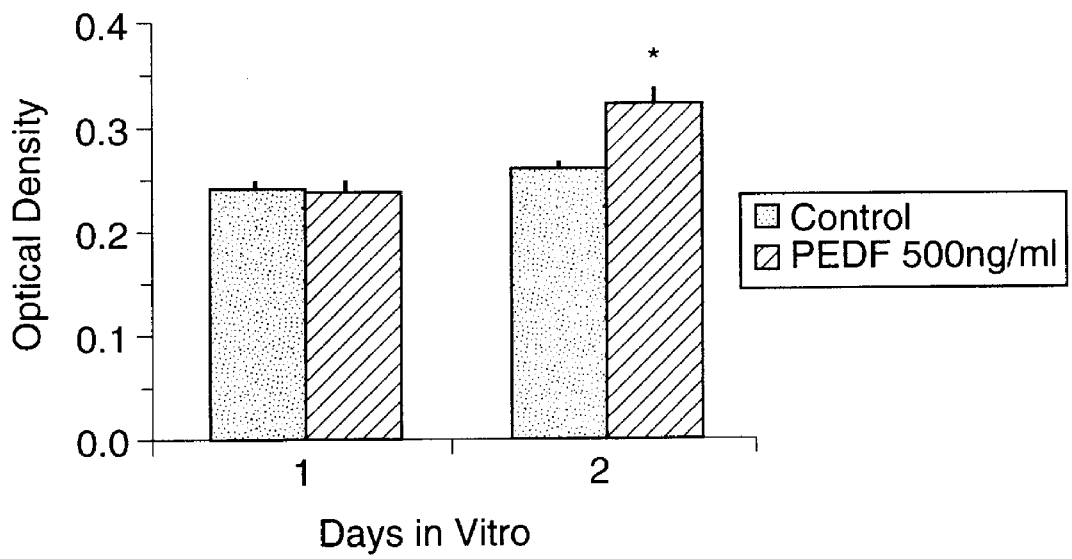
Figure 10:
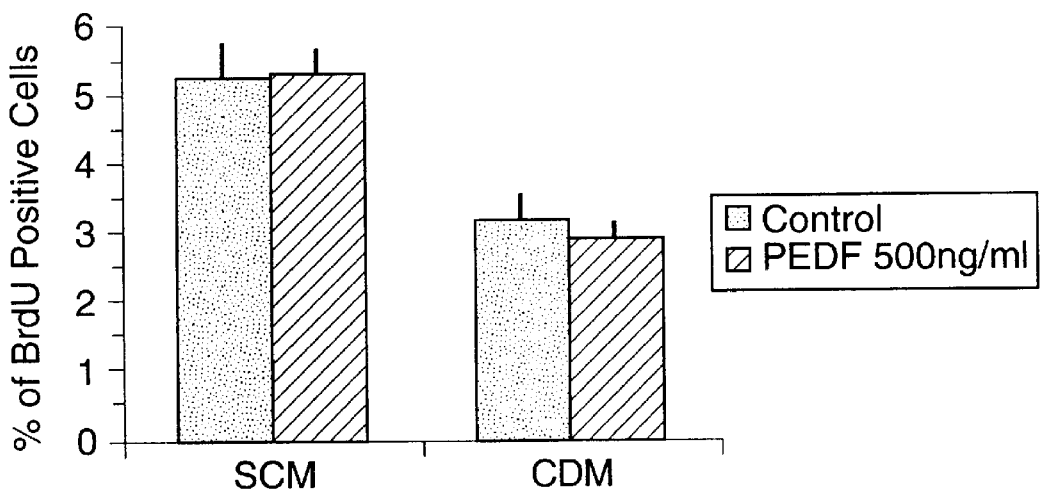

In order to determine whether the increase in O.D. (MTS assay) in response to PEDF reflected an increase in surviving cells or an increase in proliferation, a BrdU labeling study was performed using cultures from postnatal day 5 (P5) animals (a time when cerebellar granule cells are still dividing in the animal). FIG. 9 shows the effect of PEDF on P5 CGC cultures at DIV1 and 2. Using the MTS assay, PEDF had no effect at DIV1 but caused a small increase in O.D. at DIV2 in either serum-containing medium or chemically defined medium. Therefore, BrdU was added at day 1 and cells were fixed on day 2. The BrdU labeling index was 5% in SCM and 3% in CDM, under control conditions, and PEDF did not increase the BrdU labeling index in either culture medium (FIG. 10). The lack of stimulation of the BrdU labeling index by PEDF implies that enhanced survival rather than increased cell division is responsible for the increased O.D. measured by the MTS assay after exposure to PEDF.

Immunocytochemistry was used to identify the cells present in cultures before and after treatment with PEDF. P8 cultures grown for 7 days with and without PEDF (500 ng/ml) were stained with four different antibodies: a polyclonal rabbit antibody to neuron-specific enolase (NSE), which recognizes all cerebellar neurons (Schmechel et al. 1978 *Science*, 199:313–315); a polyclonal antibody to GABA, which is synthesized in all cerebellar neurons except cerebellar granule cells (Gruol and Crimi, 1988 *Dev. Brain Res.*, 41:135–146); an antibody to calbindin, which is a neuron-specific protein and GFAP, an intermediate filament protein present only in astrocytes. The results are summarized in Table 2. PEDF significantly increased the number of NSE-positive cells in both SCM (30% increase) and in CDM (60% increase). There was a small, not statistically significant, increase in the number of GABA-positive neurons and Purkinje cells (calbindin-positive). Thus, PEDF is neuronotrophic only for granule neurons. In addition, PEDF significantly decreased the number of GFAP-positive astrocytes present in the cultures (30% decrease in SCM and 40% decrease in CDM). This "gliastatic" property of PEDF is further discussed in Example 14.

TABLE 2

Immunocytochemistry demonstrates that PEDF Increased The Number of NSE-Positive Cells (Neurons) But Decreased GFAP-Positive Cells (Glia)

| Antigen | Treatment | SCM | CDM |
| --- | --- | --- | --- |
| NSE | Control PEDF | 100.0 ± 6.2 | 100.0 ± 4.5 |
|  | PEDF | 127.0 ± 5.9* | 157.2 ± 7.4* |
| GABA | Control | 2.8 ± 0.2 | 1.4 ± 0.2 |
|  | PEDF | 3.2 ± 0.2 | 1.8 ± 0.2 |
| Calbindin | Control | 0.06 ± 0.01 | 0.07 ± 0.02 |
|  | PEDF | 0.07 ± 0.02 | 0.12 ± 0.02 |
| GFAP | Control | 0.86 ± 0.07 | 0.99 ± 0.07 |
|  | PEDF | 0.60 ± 0.03* | 0.60 ± 0.06* |

Postnatal-day 8 cerebellar granule cells were cultured in 8-well chamber slides. PEDF (500 ng/ml) was added at DIV 0, the cells were fixed on DIV 7, and the immunocytochemistry was carried out using antibodies against NSE, GABA, Calbindin and GFAP. At least 20 fields were counted from 2–3 wells for each experiment. Data are expressed as percent of control of NSE-positive cells. Each experiment value represents mean cell number ± SEM. *P < 0.005 compared with each other control by using non-paired test.

Figure 11:
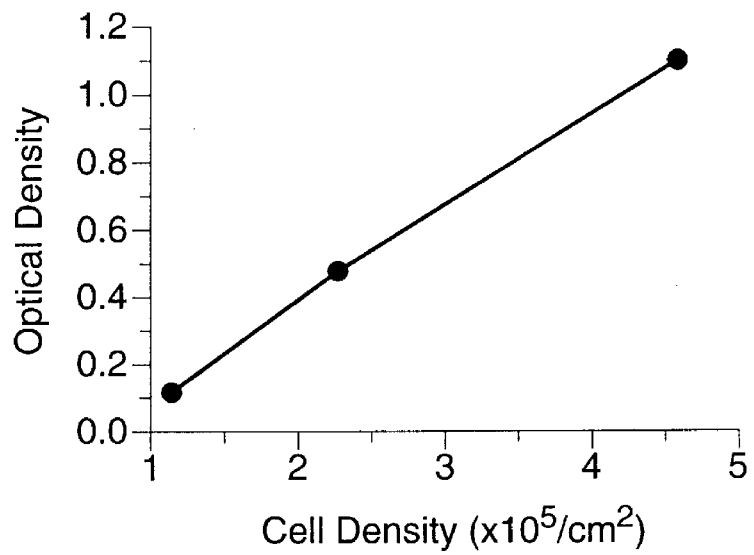
Figure 12:
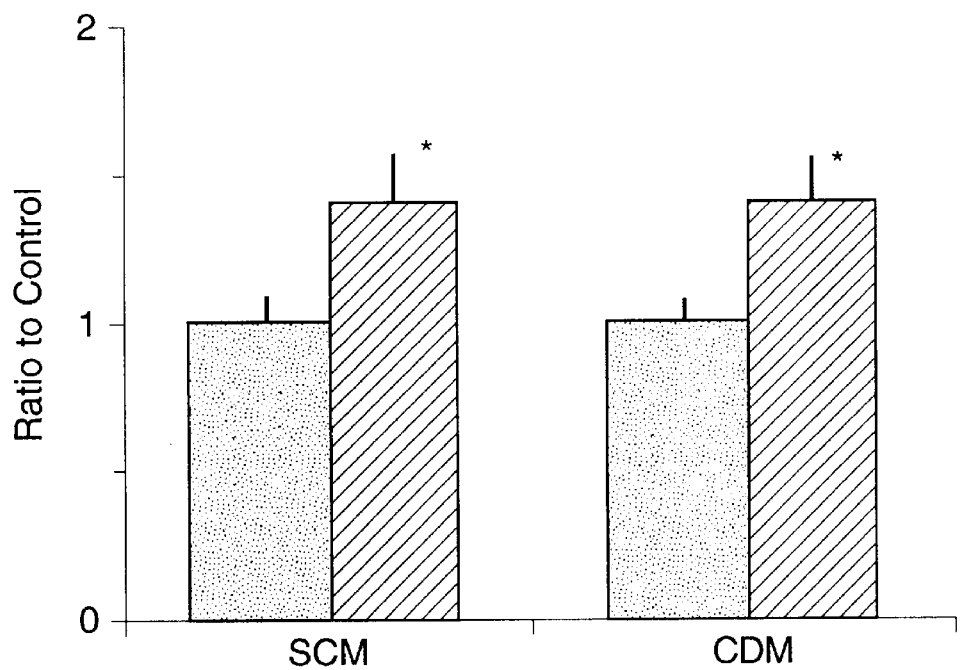

In order to investigate the effects of PEDF on neurite outgrowth, a neurofilament ELISA assay was used. Immunocytochemistry had shown that the monoclonal antibody RMO-42, stained only the neurites of cerebellar granule cells in culture, so this antibody was used as a direct measure of neurofilament present only in processes and not the cell body (FIG. 11). PEDF slightly increased neurofilament content, both in SCM and CDM, but the increase was directly proportional to the increase in cell number (FIG. 12).

Figure 13:
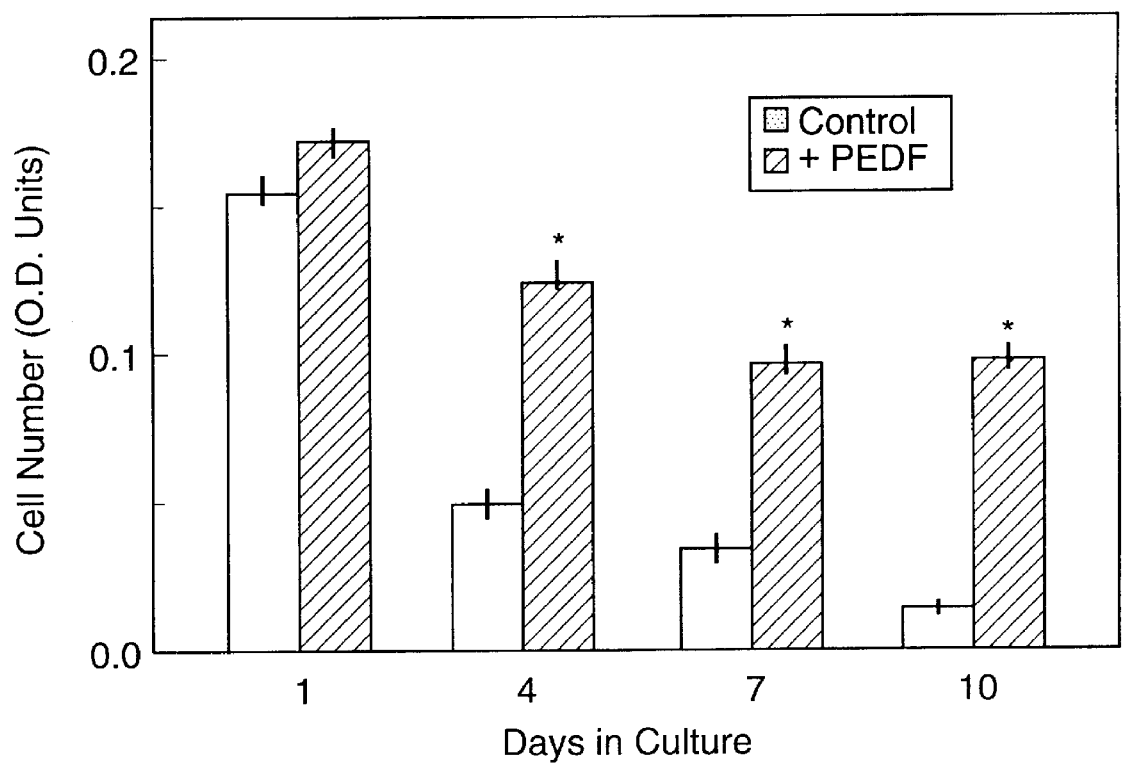

FIG. 13 summarizes the data from this Example. By 10 days in culture, most untreated CGCs die (control) but 60% or more of the PEDF-treated cells remain viable. PEDF is thus a potent survival factor for brain neurons.

EXAMPLE 13
Neuronotrophic properties of rPEDF peptides, BP and BX

Figure 14:
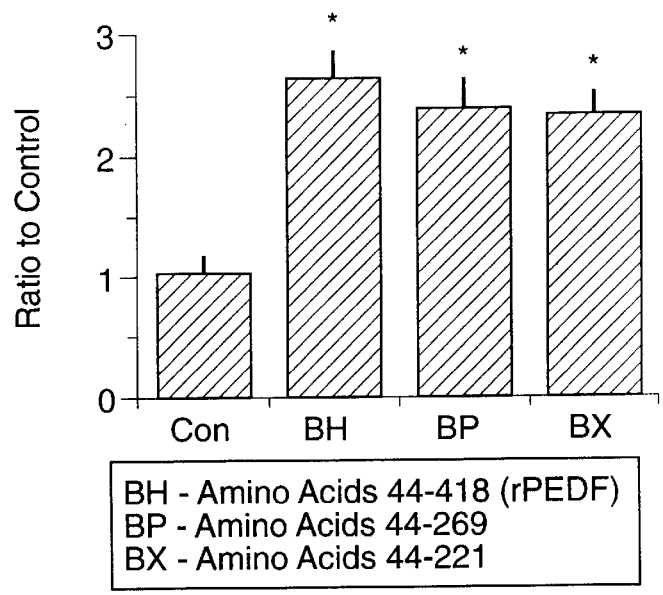

Described in the previous sections on the "neuronotrophic" activity of PEDF is the fact that we can produce relatively large amounts of a recombinant PEDF (rPEDF) that exhibits potent neurotrophic activity. Using appropriate recombinant molecular biological technology, we can also produce smaller fragments of the PEDF molecule that can be tested for either neurotrophic or neuronotrophic activity. FIG. 14 shows the effects of two of these truncated forms of PEDF on CGC viability. BX and BP are 24 and 28 kDa fragment from the amino-terminal portion of the PEDF molecule, respectively. Both fragments at 1× or 10× concentrations act as neuron-survival factors, significantly promoting the life of the CGC's. In this experiment, the peptide was given once at the beginning of the experiment and the cell number was determined 7 days later. We conclude that, along with the full PEDF molecule, smaller recombinant peptides near the N-terminal of the molecule are "neuronotrophic".

EXAMPLE 14
Gliastatic properties of PEDF

Along with neurons in the primary cultures of rat cerebellar granule cells are a small number of different types of glia. Glia are the "support" elements in the CNS for neurons, forming the architectural framework and the metabolic support system on which neurons depend. Glia are also of clinical importance since tumors of the brain are mostly formed by glia and gliosis is a problem in several neurodegenerative diseases. In our system, we first noticed an effect of PEDF on glia when we immunocytochemically stained the cultured mixed population of cells with antibodies specific for neurons and other antibodies specific for different types of glia. For this purpose, we used the standard markers Neuron-Specific Enolase (NSE) and others to demonstrate the presence of neurons, Glial Fibrillary Acidic Protein (GFAP) to demonstrate the presence of astroglia and OX-42 to stain microglia. In this experiment (Table 2), we found the expected increase in NSE staining with PEDF treatment since we then knew that the neurons were living longer but we found an unexpected decrease in GFAP staining. This indicated the possibility of fewer astrocytes in the PEDF-treated cultures.

Figure 15:
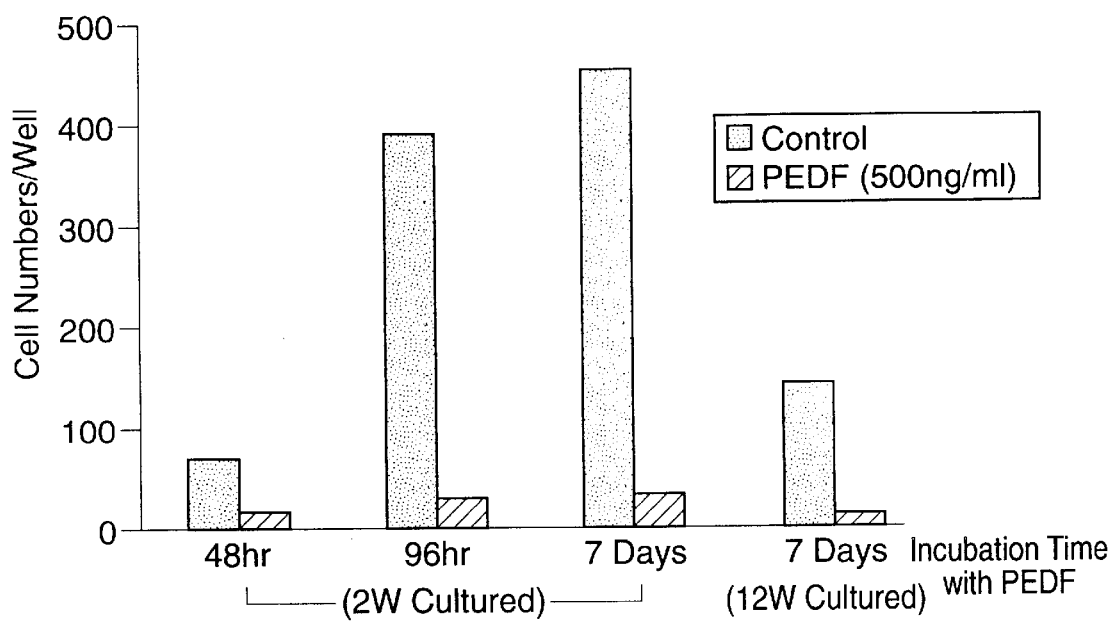
Figure 16:
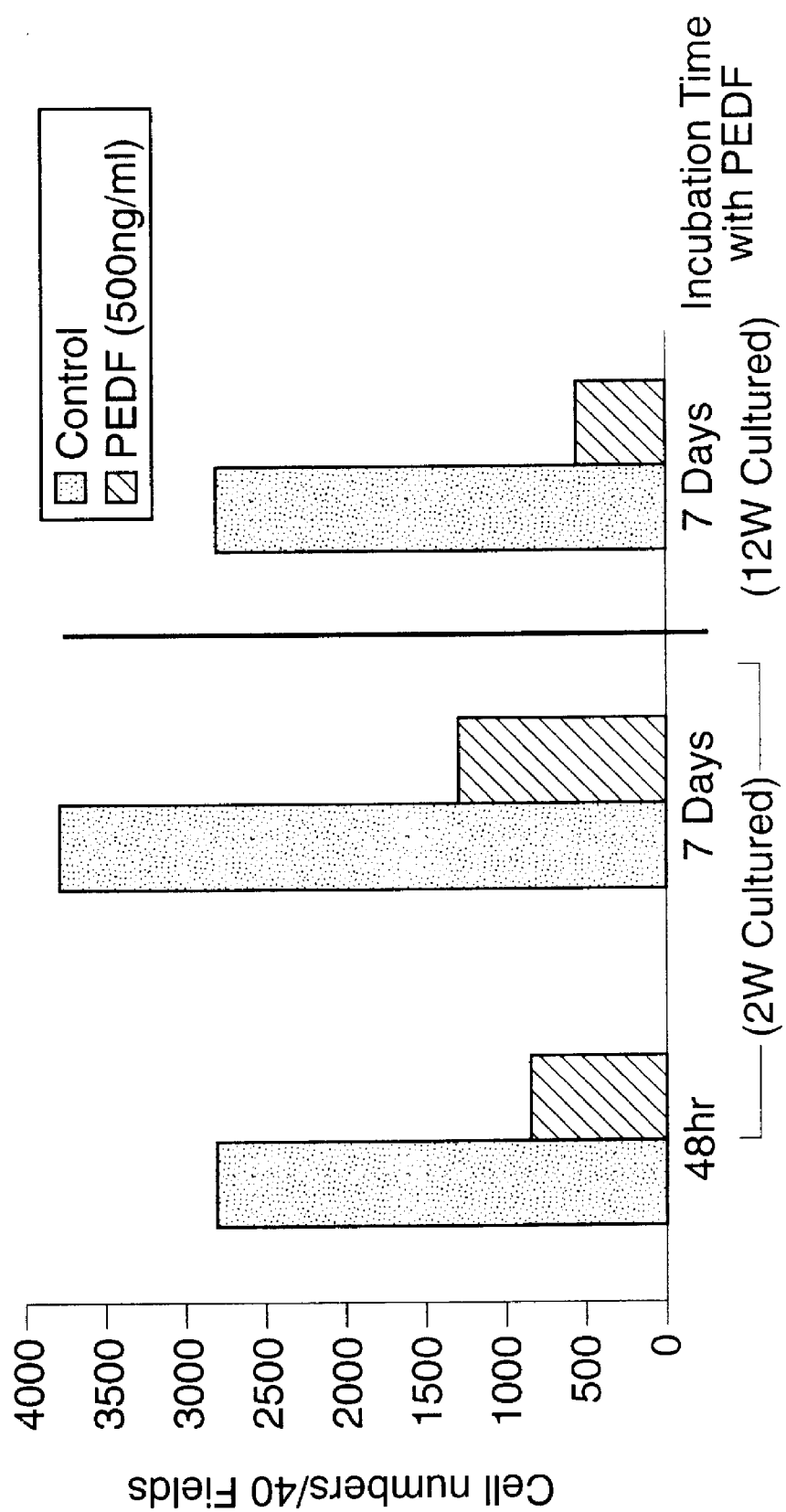

Because of the distinctive morphology of astroglia and microglia in the culture dishes and their selective staining for GFAP or OX-42, it is possible to individually count their numbers under the microscope under different experimental conditions. This has now been done as outlined in FIGS. 15 and 16. FIG. 15 shows the effects of PEDF on numbers of astroglia in cultures obtained from rat brain at 2 weeks (2 w) or 12 weeks (12 w) in culture. Times given are 48 hrs, 96 hrs or 7 days after treatment with PEDF. Clearly, under all the conditions tested, PEDF treatment results in a dramatic decrease in the number of astroglia. FIG. 16 shows a parallel analysis of microglia in the same cultures. Administration of PEDF for 48 hrs. or 7 days resulted in fewer numbers of the cells whether they has been cultured for 2 weeks (2 W) or 12 weeks (12 W). Thus, PEDF substantially decreases glial elements over a very long period of time while acting as a survival factor for neurons.

EXAMPLE 15
Characterization of Native Bovine PEDF

Since the specific antibody indicated the presence of PEDF in the adult IPM, we used bovine IPM washes as a source for purification of native PEDF. Although RPE and retinal cells express PEDF mRNA, anti-BH could not detect PEDF bands on Western transfers in these cell extracts, suggesting a rapid PEDF release into the IPM. We now estimate that PEDF is present in bovine IPM at less than 1% of the total soluble protein (i.e. about 2–5 ng/bovine eye). At physiological temperatures, the PEDF protein in the IPM remains stable for extended periods of time and does not form non-reduced complexes resistant to SDS. Thus, its potential usefulness in culture experiments and transplantation in vivo is greatly enhanced due to its stable nature.

Figure 17B:
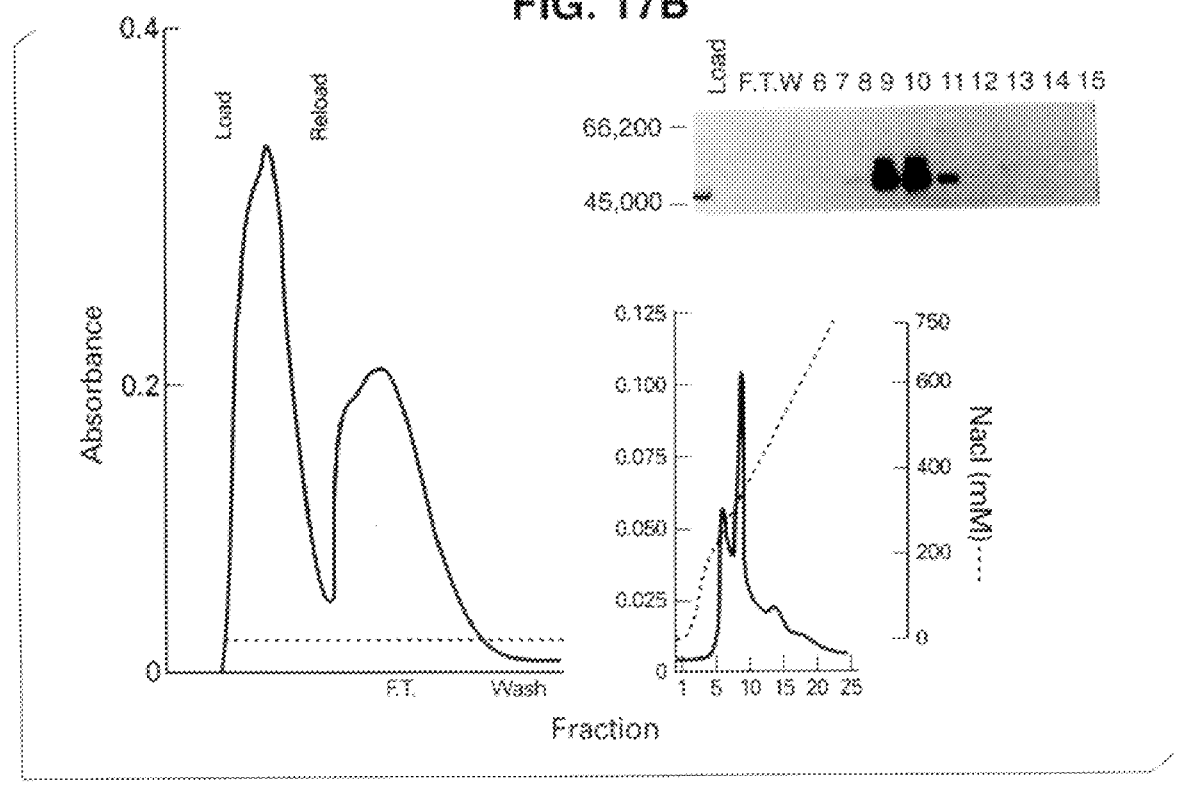

Purification to apparent homogeneity is achieved by a simple two-step procedure (FIG. 17A and B). Components of IPm were fractionated by size-exclusion column chromatography (TSK-3000). The PEDF-immunoreactive fractions were pooled, applied to a cation-exchange column (Mono-S) and immunoreactivity was eluted with a NaCl linear gradient. Purification protocol is detailed in Materials and Methods. Elution profiles of each chromatography are shown in: panel A, TSK-3000 size-exclusion column chromatography, and panel B, mono-S column chromatography. Absorbance at 280 nm is represented by ___, and NaCl concentration by —, PEDF-immunoreactivity was followed with antiserum Ab-rPEDF. The inserts correspond to Western blot analysis of the indicated fractions. Immunoreaction was performed with a 1:10,000 dilution of Ab-rPEDF and stained with 4-chloro-1-napthtol. Molecular size standards for the TSK-3000 chromatography were: BSA, bovine serum albumin (66,000); and CA, bovine carbonic anhydrase (29,000).

Starting with a wash of soluble IPM components, the first step involves removal of the most abundant protein, IRBP, by size exclusion chromatography. PEDF elutes as a monomeric polypeptide around 50 kDa in size. Since we have determined that PEDF's isoelectric point is 7.2–7.8, we have used S-sepharose column chromatography at pH 6.0 in the second step of our procedure to simultaneously purify and concentrate the protein. Purified protein is recovered at about 2 ug protein per adult bovine eye with a recovery of about 40%. Native PEDF behaves like a monomeric glycoprotein with an apparent molecular weight of 49,500±1,000 on SDS-PAGE.

Figure 18A:
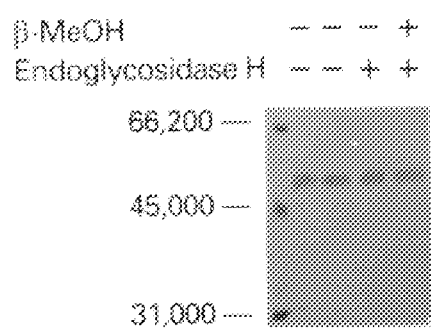
Figure 18B:
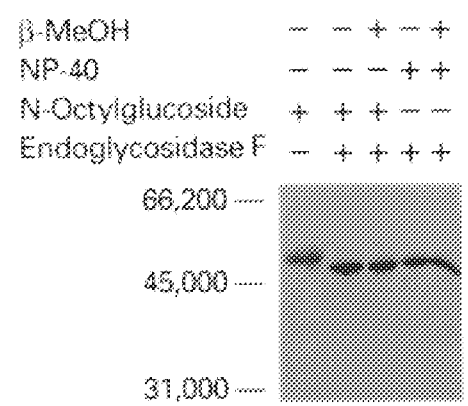

The purified protein is sensitive to glycosidase F, revealing N-linked oligosaccharides that account for up to 3,000-Mr of the native protein (FIG. 18). To remove asparagine-linked oligosaccharides purified PEDF protein was treated with endoglycosidase H and N-Glycosidase F. Enzymatic reactions were performed as described in Materials and Methods with a total of 200 ng of PEDF protein in the presence or absence of β-mercaptoethanol. Reactions mixtures were applied to SDS-12.5% polyacrylamide gel. Photographs of western transfers of endoglycosidase H (left panel) and N-Glycosidase F (right panel) reactions are shown. Immunoblots were treated with antiserum Ab-rPEDF diluted 1:10,000. Addition in each reaction are indicated at the top. The numbers at the right side of each photograph indicate the migration of biotinylated SDS-PAGE standards: bovine serum albumin (66,200), ovalbumin (45,000) and bovine carbonic anhydrase (31,000). We have shown that purified bovine PEDF promotes neurite outgrowth on Y-79 cells and Weri retinoblastoma cells, and that this activity is blocked by Anti-rPEDF (see below).

The present invention provides the tools for determining the effect of authentic PEDF on the expression of neuronal and glial markers in the CGC cultures and Y-79 tumor cells including NSE, GFAP, neurofilament (NF-200) protein.

EXAMPLE 16

Figure 19A:
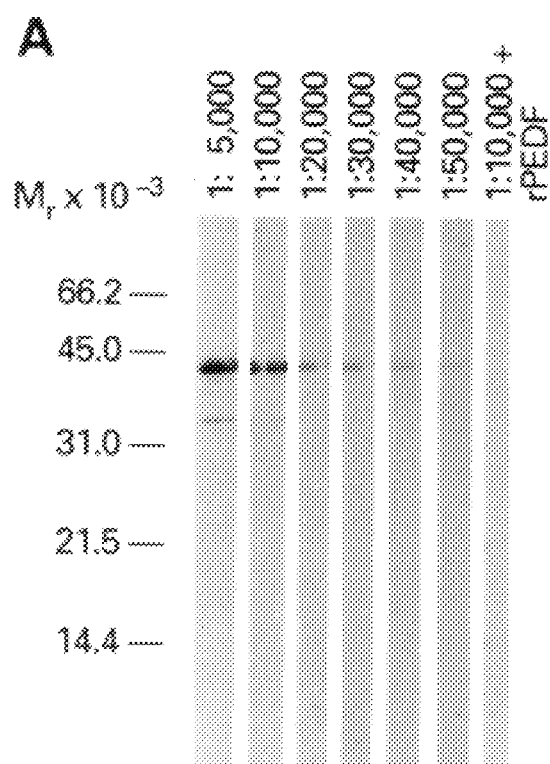
Figure 19B:
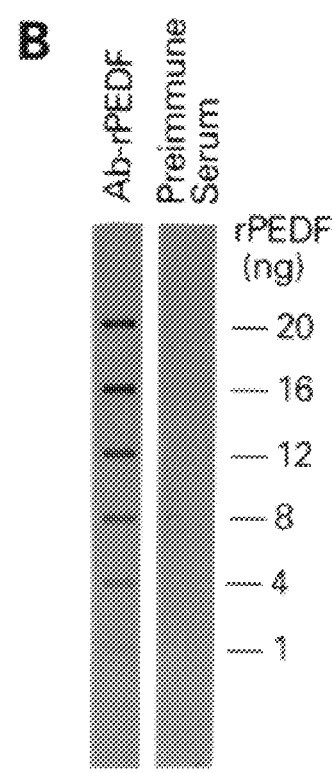

Pigment Epithelium-Derived Factor: Characterization Using A Highly Specific Polyclonal Antibody We have used purified recombinant human PEDF produced in E. coli to develop polyclonal antibodies against PEDF. Anti-rPEDF specifically recognized one polypeptide on Western transfer of IPM wash from adult bovine eyes (FIG. 19A and B). Polyclonal antiserum to human recombinant PEDF specifically recognizes rPEDF. Western transfer and slot blot of human rPEDF were treated with rabbit polyclonal antiserum to rPEDF, Ab-rPEDF. Photographs of immunostaining with 4-chloro-naphthol are shown. Panel A, Western transfers of 0.5 μg of rPEDF were used to assay increasing dilutions of antiserum. rPEDF protein was resolved by SDS-12.5% PAGE before transfer. Dilutions are indicated at the top of each lane. Diluted antiserum was preincubated with rPEDF at 5 μg/ml before using for immunodetection and is indicated as 1:10,000+rPEDF. The numbers to the left indicate the molecular weight of biotinylated SDS-PAGE standards. Panel B increasing amounts of rPEDF in 1% BSA/PBS were applied to a nitrocellulose membrane with a manifold. The membranes were treated with antiserum Anti-rPEDF and rabbit preimmune serum diluted 1:10,000. The numbers to the right indicate the amounts of rPEDF protein blotted on the membrane. The sera used in each paper are indicated at the top of the figure.

Figure 20:
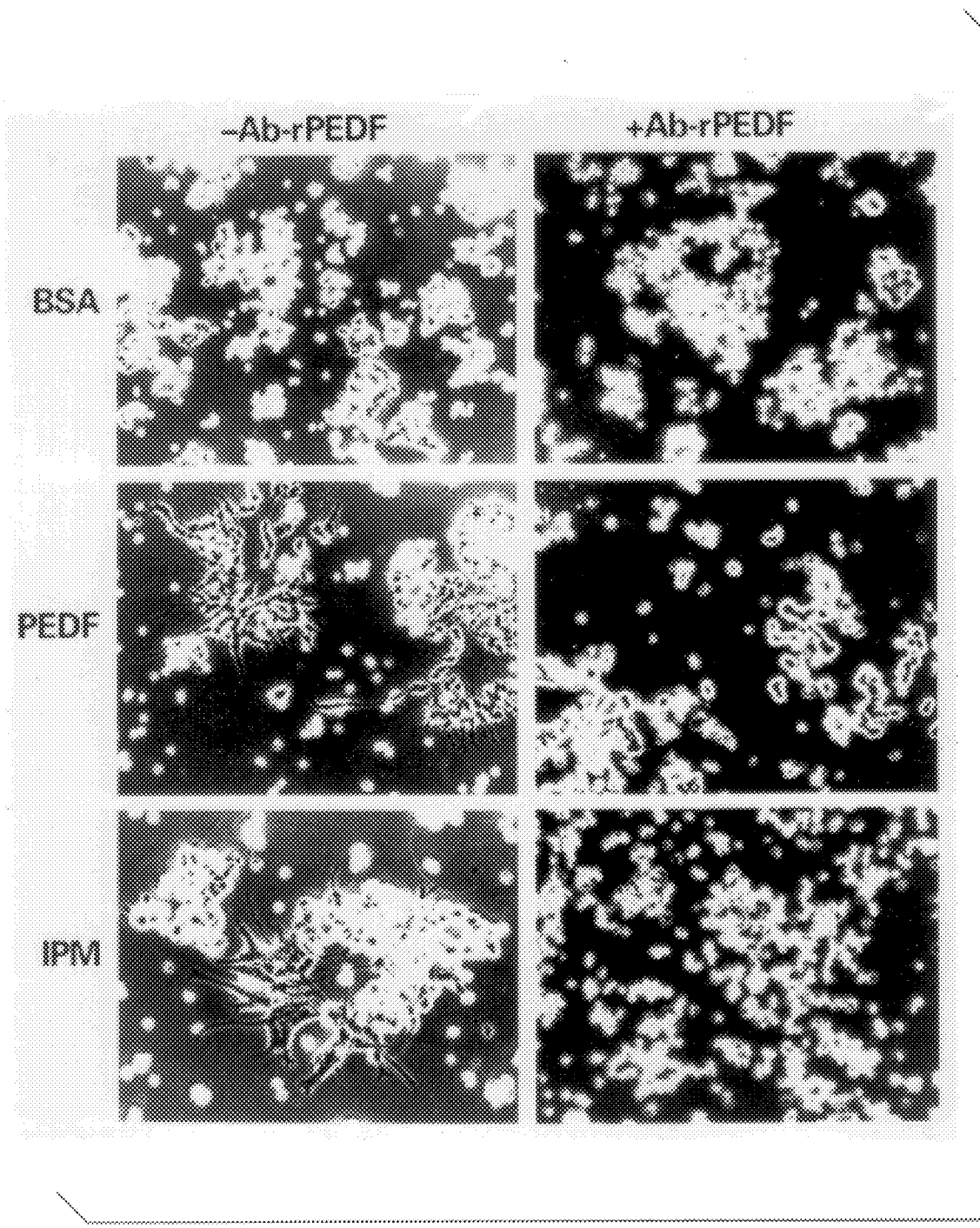

Anti-BH specifically recognizes human PEDF on Western transfers at dilutions as low as 1:50,000; importantly, it does not recognize serum $\alpha_1$-antitrypsin. The antibody recognizes one major band on Western transfers of conditioned medium from juvenile monkey RPE cells in culture as well as of IPM from adult bovine eyes. Anti-rPEDF blocked the IPM-promoting neurotrophic activity (FIG. 20). Human retinoblastoma Y-79 cells exponentially growing in serum containing medium were washed twice with PBS, and plated ($2.5 \times 10^5$) cell per ml) in serum-free MEM supplemented with insulin, transferring and selenium (ITS mix, Collaborative Research Products). Effectors were then added to the cultures. After 7 days at 37° C. in 5% $CO_2$, the cells were attached to poly-D-lysine coated plates with fresh serum-free medium. The differentiation state of the cultures was monitored at different intervals after attachment. Morphology characteristic of 9-day post-attachment cultures is shown. Addition of effectors were as indicated in each panel at the following final concentrations: 125 μg/ml BSA, 1% IPM, and 100 ng/ml purified bovine PEDF. In order to block the neurite outgrowth inducing activity each effector was preincubated with an excess of antiserum Anti-rPEDF (1 μl) in 1% BSA/PBS at 4° C. for at least 6 hours. All photographs are shown at ×50 magnification.

The anti-rPEDF also blocked the neurite-outgrowth activity promoted by the purified PEDF. Our data indicate that PEDF is the only neurotrophic factor in the IPM. These results also suggest that the anti-rPEDF will be useful in probing the PEDF neurotrophic active site as well as the physiological role of PEDF in the IPM and other tissues (e.g. brain) as well. Further, these results indicate that PEDF is a bona fide component of the IPM and is probably the sole neurotrophic component in the extracellular matrix. Moreover, the protein is present in a wide range of tissues and extracellular spaces. The blocking antibody is useful in studies probing the physiological functions of PEDF.

EXAMPLE 17

Pigment Epithelium-Derived Factor: A Serpin With Neurotrophic Activity

The amino acid sequence derived from a fetal human PEDF cDNA shares identity of its primary structure (~30%) with the serine protease inhibitor (serpin) family, preserving 90% of the residues essential for the structural integrity of serpins. However, recombinant PEDF does not inhibit the serine proteases trypsin, chymotrypsin, elastase or cathepsin G. A natural target for PEDF has not yet been identified. We have analyzed proteins from the interphotoreceptor matrix (IPM), the space between the retinal pigment epithelium and the retina by immunodetection on Western blots with antibodies raised against PEDF and by zymography in gels containing casein as a proteolytic substrate. Our results show that bovine IPM contains a stable, glycosylated PEDF polypeptide (50,000 Mr) at about 2–5 μg per eye. Limited proteolysis of bovine PEDF produced a polypeptide of 46,000 Mr with trypsin, subtilisin, chymotrypsin and elastase, suggesting a globular structure with a hinge region susceptible to proteolytic cleavage. On the other hand, casein SDS-PAGE zymography revealed low protease activity in the IPM which migrated as a double of about 80,000±5,000 Mr. The caseinolytic activities were inhibited 100% with 1 μg/ml aprotinin and 10 mM PMSF added to the gel mixture, but were not affected by E64 or EDTA. Importantly, IPM protein did not react with antibody against plasminogen, a serine protease of about 80,000 Mr. When rPEDF protein was added at 1 μg/ml, the signal for these caseinolytic activities, as well as another serine protease activity of unknown origin, diminished by about 50%. Our results suggest the IPm as a natural extracellular site for a novel serine protease and the serpin PEDF, both present at ≦1% of the total protein.

All of the references cited herein are hereby incorporated in their entireties by reference.

The present invention discloses the general structural features of PEDF and beginnings of understanding of how these relate to function of the protein. PEDF possesses the structural features and general tertiary characteristics previously attributed to serpins but not its anti-protease activity. PEDF is a neurotrophic protein and appears to be the sole component of the IPM that promotes neurite-outgrowth on retinoblastoma cells. However, the reactive center for serine protease inhibition found near the carboxy terminal of classical serpins is not necessary for PEDF's neurotrophic biological activity. Specifically, a polypeptide chain containing a domain from the amino-terminal portion of the molecule (BA) is sufficient for neurotrophic and neuron-survival activity. The present invention further allows for determination of whether the CGC neurons normally die by apoptosis and whether PEDF is an apoptosis inhibitor. In other words, the present invention allows one to determine by what mechanism PEDF "saves" neurons and "inhibits" glia growth or proliferation.

The present invention is useful in determining the specific neurotrophic "active site". Further, the use of rPEDF truncated peptides allows us to define the elements necessary for neuronotrophic and perhaps gliastatic activity of PEDF. The present invention further provides necessary tools to study the interactions of PEDF that trigger the signal for differentiation of retinoblastoma. Recent experiments demonstrate that $^{125}$I-BH binds to retinoblastoma cells in competitive fashion only when added in medium that had been previously "conditioned" by retinoblastoma cells. This suggests that one or more co-factors produced by the cells could be required for binding. The present invention further provides the tools necessary to identify and characterize a putative cell-surface receptor for PEDF or for a PEDF complex from our CGC and retinoblastoma test systems.

Recombinant mutated proteins, proteolytic products and synthetic peptides have become instrumental in domain mapping of functional sites of proteins. Further, the recombinant proteins of the present invention allow the mapping of neurotrophic and neuronotrophic "active sites" on the PEDF molecule and the determination of the cellular transduction mechanism through which this interesting protein exerts its dramatic biological effects.

While this invention has been described with an emphasis upon preferred embodiments, it will be obvious to those of ordinary skill in the art that variations in the preferred nucleic acids coding for, and the amino acid sequences of, PEDF, rPEDF, and equivalent proteins, (BP, BX, BA) the vectors utilizing any such nucleic acids, the recombinant methods of producing such proteins, and the methods of using such proteins, may be realized and that it is intended that the invention may be practiced otherwise than as specifically described herein. Accordingly, this invention includes all modifications encompassed within the spirit and scope of the invention as defined by the following claims.

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 1489 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: mRNA
        ( B ) LOCATION: 1..1489
        ( D ) OTHER INFORMATION: PEDF coding region
            starts at nucleotide 117

( x i ) SEQUENCE DESCRIPTION: SEQ ID NO:1:

```
GGACGCTGGA    TTAGAAGGCA    GCAAAAAAG    ATCTGTGCTG                    4 0

GCTGGAGCCC    CCTCAGTGTG    CAGGCTTAGA    GGGACTAGGC                    8 0

TGGGTGTGGA    GCTGCAGCGT    ATCCACAGGC    CCCAGGATGC                    1 2 0

AGGCCCTGGT    GCTACTCCTC    TGCATTGGAG    CCCTCCTCGG                    1 6 0

GCACAGCAGC    TGCCAGAACC    CTGCCAGCCC    CCCGGAGGAG                    2 0 0

GGCTCCCCAG    ACCCCGACAG    CACAGGGGCG    CTGGTGGAGG                    2 4 0
```

| | | | | |
|---|---|---|---|---|
| AGGAGGATCC | TTTCTTCAAA | GTCCCCGTGA | ACAAGCTGGC | 280 |
| AGCGGCTGTC | TCCAACTTCG | GCTATGACCT | GTACCGGGTG | 320 |
| CGATCCAGCA | TGAGCCCCAC | GACCAACGTG | CTCCTGTCTC | 360 |
| CTCTCAGTGT | GGCCACGGCC | CTCTCGGCCC | TCTCGCTGGG | 400 |
| AGCGGACGAG | CGAACAGAAT | CCATCATTCA | CCGGGCTCTC | 440 |
| TACTATGACT | TGATCAGCAG | CCCAGACATC | CATGGTACCT | 480 |
| ATAAGGAGCT | CCTTGACACG | GTCACTGCCC | CCAGAAGAA | 520 |
| CCTCAAGAGT | GCCTCCCGGA | TCGTCTTTGA | GAAGAAGCTA | 560 |
| CGCATAAAAT | CCAGCTTTGT | GGCACCTCTG | GAAAAGTCAT | 600 |
| ATGGGACCAG | GCCCAGAGTC | CTGACGGGCA | ACCCTCGCTT | 640 |
| GGACCTGCAA | GAGATCAACA | ACTGGGTGCA | GGCGCAGATG | 680 |
| AAAGGGAAGC | TCGCCAGGTC | CACAAAGGAA | ATTCCCGATG | 720 |
| AGATCAGCAT | TCTCCTTCTC | GGTGTGGCGC | ACTTCAAGGG | 760 |
| GCAGTGGGTA | ACAAAGTTTG | ACTCCAGAAA | GACTTCCCTC | 800 |
| GAGGATTTCT | ACTTGGATGA | AGAGAGGACC | GTGAGGGTCC | 840 |
| CCATGATGTC | GGACCCTAAG | GCTGTTTTAC | GCTATGGCTT | 880 |
| GGATTCAGAT | CTCAGCTGCA | AGATTGCCCA | GCTGCCCTTG | 920 |
| ACCGGAAGCA | TGAGTATCAT | CTTCTTCCTG | CCCCTGAAAG | 960 |
| TGACCCAGAA | TTTGACCTTG | ATAGAGGAGA | GCCTCACCTC | 1000 |
| CGAGTTCATT | CATGACATAG | ACCGAGAACT | GAAGACCGTG | 1040 |
| CAGGCGGTCC | TCACTGTCCC | CAAGCTGAAG | CTGAGTTACG | 1080 |
| AAGGCGAAGT | CACCAAGTCC | CTGCAGGAGA | TGAAGCTGCA | 1120 |
| ATCCTTGTTT | GATTCACCAG | ACTTTAGCAA | GATCACAGGC | 1160 |
| AAACCCATCA | AGCTGACTCA | GGTGGAACAC | CGGGCTGGCT | 1200 |
| TTGAGTGGAA | CGAGGATGGG | GCGGGAACCA | CCCCCAGCCC | 1240 |
| AGGGCTGCAG | CCTGCCCACC | TCACCTTCCC | GCTGGACTAT | 1280 |
| CACCTTAACC | AGCCTTTCAT | CTTCGTACTG | AGGGACACAG | 1320 |
| ACACAGGGGC | CCTTCTCTTC | ATTGGCAAGA | TTCTGGACCC | 1360 |
| CAGGGCCCCT | AATATCCCAG | TTTAATATTC | CAATACCCTA | 1400 |
| GAAGAAAACC | CGAGGGACAG | CAGATTCCAC | AGGACACGAA | 1440 |
| GGCTGCCCCT | GTAAGGTTTC | AATGCATACA | ATAAAAGAGC | 1480 |
| TTTATCCCT | | | | 1489 |

( 2 ) INFORMATION FOR SEQ ID NO:2:

( i ) SEQUENCE CHARACTERISTICS:
        ( A ) LENGTH: 418 amino acids
        ( B ) TYPE: amino acid
        ( D ) TOPOLOGY: linear ( i i ) MOLECULE TYPE: protein ( i x ) FEATURE:
        ( A ) NAME/KEY: CDS
        ( B ) LOCATION: 117..1373
        ( D ) OTHER INFORMATION: /note="product =
          " pigment epithelial-derived factor"

gene ="PEDF"codon_start = 1"

( i x ) FEATURE:
    ( A ) NAME/KEY: sig_peptide
    ( B ) LOCATION: 117..170
    ( D ) OTHER INFORMATION: PEDF amino acid
        sequence ( x i ) SEQUENCE DESCRIPTION: SEQ ID NO:2:

| | | | | | | | | | |
|---|---|---|---|---|---|---|---|---|---|
| Met | Gln | Ala | Leu | Val | Leu | Leu | Cys | Ile | Gly | Ala |
| 1 | | | | 5 | | | | | 10 | |
| Leu | Leu | Gly | His | Ser | Ser | Cys | Gln | Asn | Pro | Ala | Ser |
| | | 15 | | | | 20 | | | | | |
| Pro | Pro | Glu | Glu | Gly | Ser | Pro | Asp | Pro | Asp | Ser | Thr |
| 25 | | | | | 30 | | | | | 35 | |
| Gly | Ala | Leu | Val | Glu | Glu | Glu | Asp | Pro | Phe | Phe | Lys |
| | | | 40 | | | | | 45 | | | |
| Val | Pro | Val | Asn | Lys | Leu | Ala | Ala | Val | Ser | Asn |
| | 50 | | | | | 55 | | | | 60 |
| Phe | Gly | Tyr | Asp | Leu | Tyr | Arg | Val | Arg | Ser | Ser | Met |
| | | | | 65 | | | | | 70 | | |
| Ser | Pro | Thr | Thr | Asn | Val | Leu | Leu | Ser | Pro | Leu | Ser |
| | | 75 | | | | | 80 | | | | |
| Val | Ala | Thr | Ala | Leu | Ser | Ala | Leu | Ser | Leu | Gly | Ala |
| 85 | | | | | 90 | | | | | 95 | |
| Asp | Glu | Arg | Thr | Glu | Ser | Ile | Ile | His | Arg | Ala | Leu |
| | | | 100 | | | | | 105 | | | |
| Tyr | Tyr | Asp | Leu | Ile | Ser | Ser | Pro | Asp | Ile | His | Gly |
| | | 110 | | | | 115 | | | | | 120 |
| Thr | Tyr | Lys | Glu | Leu | Leu | Asp | Thr | Val | Thr | Ala | Pro |
| | | | | 125 | | | | | 130 | | |
| Gln | Lys | Asn | Leu | Lys | Ser | Ala | Ser | Arg | Ile | Val | Phe |
| | | 135 | | | | | 140 | | | | |
| Glu | Lys | Lys | Leu | Arg | Ile | Lys | Ser | Ser | Phe | Val | Ala |
| 145 | | | | | 150 | | | | | 155 | |
| Pro | Leu | Glu | Lys | Ser | Tyr | Gly | Thr | Arg | Pro | Arg | Val |
| | | | 160 | | | | | 165 | | | |
| Leu | Thr | Gly | Asn | Pro | Arg | Leu | Asp | Leu | Gln | Glu | Ile |
| | 170 | | | | | 175 | | | | | 180 |
| Asn | Asn | Trp | Val | Gln | Ala | Gln | Met | Lys | Gly | Lys | Leu |
| | | | | 185 | | | | | 190 | | |
| Ala | Arg | Ser | Thr | Lys | Glu | Ile | Pro | Asp | Glu | Ile | Ser |
| | | 195 | | | | | 200 | | | | |
| Ile | Leu | Leu | Leu | Gly | Val | Ala | His | Phe | Lys | Gly | Gln |
| 205 | | | | | 210 | | | | | 215 | |
| Trp | Val | Thr | Lys | Phe | Asp | Ser | Arg | Lys | Thr | Ser | Leu |
| | | | 220 | | | | | 225 | | | |
| Glu | Asp | Phe | Tyr | Leu | Asp | Glu | Glu | Arg | Thr | Val | Arg |
| | | 230 | | | | 235 | | | | | 240 |
| Val | Pro | Met | Met | Ser | Asp | Pro | Lys | Ala | Val | Leu | Arg |
| | | | | 245 | | | | | 250 | | |
| Tyr | Gly | Leu | Asp | Ser | Asp | Leu | Ser | Cys | Lys | Ile | Ala |
| | | 255 | | | | 260 | | | | | |
| Gln | Leu | Pro | Leu | Thr | Gly | Ser | Met | Ser | Ile | Ile | Phe |
| 265 | | | | | 270 | | | | | 275 | |
| Phe | Leu | Pro | Leu | Lys | Val | Thr | Gln | Asn | Leu | Thr | Leu |

|     |     |     |     |     | 280 |     |     |     | 285 |     |     |
| --- | --- | --- | --- | --- | --- | --- | --- | --- | --- | --- | --- |

Ile Glu Glu Ser Leu Thr Ser Glu Phe Ile His Asp
    290                               295                     300

Ile Asp Arg Glu Leu Lys Thr Val Gln Ala Val Leu
                     305                            310

Thr Val Pro Lys Leu Lys Leu Ser Tyr Glu Gly Glu
           315                     320

Val Thr Lys Ser Leu Gln Glu Met Lys Leu Gln Ser
325                     330                        335

Leu Phe Asp Ser Pro Asp Phe Ser Lys Ile Thr Gly
           340                       345

Lys Pro Ile Lys Leu Thr Gln Val Glu His Arg Ala
    350                    355                     360

Gly Phe Glu Trp Asn Glu Asp Gly Ala Gly Thr Thr
                365                     370

Pro Ser Pro Gly Leu Gln Pro Ala His Leu Thr Phe
        375                  380

Pro Leu Asp Tyr His Leu Asn Gln Pro Phe Ile Phe
385                     390                      395

Val Leu Arg Asp Thr Asp Thr Gly Ala Leu Leu Phe
           400                      405

Ile Gly Lys Ile Leu Asp Pro Arg Gly Pro
410                     415

( 2 ) INFORMATION FOR SEQ ID NO:3:

( i ) SEQUENCE CHARACTERISTICS:
        ( A ) LENGTH: 379 amino acids
        ( B ) TYPE: amino acid
        ( D ) TOPOLOGY: linear ( i i ) MOLECULE TYPE: protein ( i x ) FEATURE:
        ( A ) NAME/KEY: Region
        ( B ) LOCATION: 1..4
        ( D ) OTHER INFORMATION: /note= "Met 1...Ile 4 is
            an N- terminal fusion to Asp 26...Pro 400 of
            SEQ ID NO:2; Met -18...Glu 25 of SEQ ID
            NO:2 is deleted"

( x i ) SEQUENCE DESCRIPTION: SEQ ID NO:3:

Met Asn Arg Ile Asp Pro Phe Phe Lys Val Pro Val
1                  5                         10

Asn Lys Leu Ala Ala Ala Val Ser Asn Phe Gly Tyr
            15                    20

Asp Leu Tyr Arg Val Arg Ser Ser Met Ser Pro Thr
25                     30                      35

Thr Asn Val Leu Leu Ser Pro Leu Ser Val Ala Thr
            40                    45

Ala Leu Ser Ala Leu Ser Leu Gly Ala Asp Glu Arg
    50                  55                    60

Thr Glu Ser Ile Ile His Arg Ala Leu Tyr Tyr Asp
                  65                    70

Leu Ile Ser Ser Pro Asp Ile His Gly Thr Tyr Lys
        75                  80

Glu Leu Leu Asp Thr Val Thr Ala Pro Gln Lys Asn
85                     90                      95

Leu Lys Ser Ala Ser Arg Ile Val Phe Glu Lys Lys

|   |   |   |   |   | 100 |   |   |   |   | 105 |   |
|---|---|---|---|---|---|---|---|---|---|---|---|
| Leu | Arg | Ile | Lys | Ser | Ser | Phe | Val | Ala | Pro | Leu | Glu |
|  | 110 |  |  |  |  | 115 |  |  |  |  | 120 |
| Lys | Ser | Tyr | Gly | Thr | Arg | Pro | Arg | Val | Leu | Thr | Gly |
|  |  |  |  | 125 |  |  |  |  | 130 |  |  |
| Asn | Pro | Arg | Leu | Asp | Leu | Gln | Glu | Ile | Asn | Asn | Trp |
|  |  | 135 |  |  |  |  | 140 |  |  |  |  |
| Val | Gln | Ala | Gln | Met | Lys | Gly | Lys | Leu | Ala | Arg | Ser |
| 145 |  |  |  |  | 150 |  |  |  |  | 155 |  |
| Thr | Lys | Gln | Ile | Pro | Asp | Glu | Ile | Ser | Ile | Leu | Leu |
|  |  |  | 160 |  |  |  |  | 165 |  |  |  |
| Leu | Gly | Val | Ala | His | Phe | Lys | Gly | Gln | Trp | Val | Thr |
|  | 170 |  |  |  |  | 175 |  |  |  |  | 180 |
| Lys | Phe | Asp | Ser | Arg | Lys | Thr | Ser | Leu | Glu | Asp | Phe |
|  |  |  |  | 185 |  |  |  |  | 190 |  |  |
| Tyr | Leu | Asp | Glu | Glu | Arg | Thr | Val | Arg | Val | Pro | Met |
|  |  | 195 |  |  |  |  | 200 |  |  |  |  |
| Met | Ser | Asp | Pro | Lys | Ala | Val | Leu | Arg | Tyr | Gly | Leu |
| 205 |  |  |  |  | 210 |  |  |  |  | 215 |  |
| Asp | Ser | Asp | Leu | Ser | Cys | Lys | Ile | Ala | Gln | Leu | Pro |
|  |  |  | 220 |  |  |  |  | 225 |  |  |  |
| Leu | Thr | Gly | Ser | Met | Ser | Ile | Ile | Phe | Phe | Leu | Pro |
|  | 230 |  |  |  |  | 235 |  |  |  |  | 240 |
| Leu | Lys | Val | Thr | Gln | Asn | Leu | Thr | Leu | Ile | Glu | Glu |
|  |  |  |  | 245 |  |  |  |  | 250 |  |  |
| Ser | Leu | Thr | Ser | Glu | Phe | Ile | His | Asp | Ile | Asp | Arg |
|  |  | 255 |  |  |  |  | 260 |  |  |  |  |
| Glu | Leu | Lys | Thr | Val | Gln | Ala | Val | Leu | Thr | Val | Pro |
| 265 |  |  |  |  | 270 |  |  |  |  | 275 |  |
| Lys | Leu | Lys | Leu | Ser | Tyr | Glu | Gly | Glu | Val | Thr | Lys |
|  |  |  | 280 |  |  |  |  | 285 |  |  |  |
| Ser | Leu | Gln | Glu | Met | Lys | Leu | Gln | Ser | Leu | Phe | Asp |
|  | 290 |  |  |  |  | 295 |  |  |  |  | 300 |
| Ser | Pro | Asp | Phe | Ser | Lys | Ile | Thr | Gly | Lys | Pro | Ile |
|  |  |  |  | 305 |  |  |  |  | 310 |  |  |
| Lys | Leu | Thr | Gln | Val | Glu | His | Arg | Ala | Gly | Phe | Glu |
|  |  | 315 |  |  |  |  | 320 |  |  |  |  |
| Trp | Asn | Glu | Asp | Gly | Ala | Gly | Thr | Thr | Pro | Ser | Pro |
| 325 |  |  |  |  | 330 |  |  |  |  | 335 |  |
| Gly | Leu | Gln | Pro | Ala | His | Leu | Thr | Phe | Pro | Leu | Asp |
|  |  |  | 340 |  |  |  |  | 345 |  |  |  |
| Tyr | His | Leu | Asn | Gln | Pro | Phe | Ile | Phe | Val | Leu | Arg |
|  | 350 |  |  |  |  | 355 |  |  |  |  | 360 |
| Asp | Thr | Asp | Thr | Gly | Ala | Leu | Leu | Phe | Ile | Gly | Lys |
|  |  | 375 |  |  |  |  | 380 |  |  |  |  |
| Ile | Leu | Asp | Pro | Arg | Gly | Pro |  |  |  |  |  |
|  |  |  | 400 |  |  |  |  |  |  |  |  |

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:4:

AGYAAYTTYT AYGAYCTSTA 20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

CTYTCYTCRT CSAGRTARAA 20

( 2 ) INFORMATION FOR SEQ ID NO:6:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Thr Ser Leu Glu Asp Phe Tyr Leu Asp Glu Arg
1               5                   10
Thr Val Arg Val Pro Met Met
            15

( 2 ) INFORMATION FOR SEQ ID NO:7:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Ala Leu Tyr Tyr Asp Leu Ile Ser Ser Pro Asp Ile
1               5                   10
His Gly Thr Tyr Lys Glu Leu Leu Asp Thr Val Thr
            15              20
Ala Pro Gln Xaa Asn
25

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Met Asn Glu Leu Gly Pro Arg
1               5

( 2 ) INFORMATION FOR SEQ ID NO:9:

( i ) SEQUENCE CHARACTERISTICS:
  ( A ) LENGTH: 4421 Base Pairs
  ( B ) TYPE: Nucleic Acid
  ( C ) STRANDEDNESS: Double
  ( D ) TOPOLOGY: Unknown ( i i ) MOLECULE TYPE: Genomic DNA ( v i ) ORIGINAL SOURCE:
  ( A ) ORGANISM: Human ( i x ) FEATURE:
  ( A ) NAME/KEY: JT101
  ( B ) LOCATION:
  ( C ) IDENTIFICATION METHOD:
  ( D ) OTHER INFORMATION: 7.1 kb Bam HI
        fragment Derived from human placental
        genomic DNA ( x i ) SEQUENCE DESCRIPTION: SEQ ID NO:9:

| | | | | |
|---|---|---|---|---|
| GGATCCCTTG | GTTGGGGTGT | TGGGGAAGGC | AGGGTTTTAA | 40 |
| CGGAAATCTC | TCTCCATCTC | TACAGAGCTG | CAATCCTTGT | 80 |
| TTGATTCACC | AGACTTTAGC | AAGATCACAG | GCAAACCCAT | 120 |
| CAAGCTGACT | CAGGTGGAAC | ACCGGGCTGG | CTTTGAGTGG | 160 |
| AACGAGGATG | GGGCGGGAAC | CACCCCCAGC | CCAGGGCTGC | 200 |
| AGCCTGCCCA | CCTCACCTTC | CCGCTGGACT | ATCACCTTAA | 240 |
| CCAGCCTTTC | ATCTTCGTAC | TGAGGGACAC | AGACACAGGG | 280 |
| GCCCTTCTCT | TCATTGGCAA | GATTCTGGAC | CCCAGGGGCC | 320 |
| CCTAATATCC | CAGTTTAATA | TTCCAATACC | CTAGAAGAAA | 360 |
| ACCCGAGGGA | CAGCAGATTC | CACAGGACAC | GAAGGCTGCC | 400 |
| CCTGTAAGGT | TTCAATGCAT | ACAATAAAAG | AGCTTTATCC | 440 |
| CTAACTTCTG | TTACTTCGTT | CCTCCTCCTA | TTTTGAGCTA | 480 |
| TGCGAAATAT | CATATGAAGA | GAAACAGCTC | TTGAGGAATT | 520 |
| TGGTGGTCCT | CTACTTCTAG | CCTGGTTTTA | TCTAAACACT | 560 |
| GCAGGAAGTC | ACCGTTCATA | AGAACTCTTA | GTTACCTGTG | 600 |
| TTGGATAAGG | CACGGACAGC | TTCTCTGCTC | TGGGGTATT | 640 |
| TCTGTACTAG | GATCAGTGAT | CCTCCCGGGA | GGCCATTTCC | 680 |
| TGCCCCCATA | ATCAGGAAG | CCTGCTCGTA | AACAACACAT | 720 |
| GGACAGATAG | GAGAGGCCAT | TTGTAACTTA | AGGAAACGGA | 760 |
| CCCGATACGT | AAAGATTCTG | AACATATTCT | TTGTAAGGAG | 800 |
| GTATGCCTAT | TTTACAAAGT | ACAGCCGGGT | GTGGTGGCTC | 840 |
| ATGGCTATAA | TCCCAGCACT | TTGGGAGGCC | GAGGCGGGCG | 880 |
| GATCACCTGA | GATCAGGAGT | TTGAGACCAG | CCTGACCAAC | 920 |
| ACGGAGAAAC | CCCGTCTGTA | CTAAAATAC | AAAATTAGCA | 960 |
| GGGTGTGGTG | GTACATGCCT | GTAATCCCAG | CTACTGGGGA | 1000 |
| GGCTGAGGCA | GGAGAATCAC | TTGAACCCGG | GAGGCGGAGG | 1040 |
| TTGCAGTGAG | CCGAGATCAC | GCCATTGCAC | TCCAATCTAG | 1080 |
| GCAATAAGAG | CAAAACTCCG | TCTCAAACAA | CAAAAAACCA | 1120 |
| AAGTATAACT | GGGCTTTTTG | AAGAACATGA | AACATGCCCA | 1160 |
| GTGTCTGAAG | TAGAATAACT | ACCGAACTGT | CCGTAGGACT | 1200 |

| | | | | |
|---|---|---|---|---|
| AAACTTTTTC | TTGAAAAAGC | TCTACCAAAA | AAAGTCACCG | 1240 |
| GCCACTCCCT | TGTCACAGTT | ATTAGACAGG | AGGAGAAATG | 1280 |
| ATAATTCTAC | TGCCCTTCAT | TCTACAAATG | TTTGAGTGCT | 1320 |
| AACTGTATTC | CAGATTCTCA | AAAAGCTATT | GCCAGGTATC | 1360 |
| TCTGGGGCTA | CTGATTTCCT | GATCATAATG | CAATGGCAAC | 1400 |
| CAACAGGCAC | TTGGGCATGG | TGAGGGTGGG | CAAGCTTTCA | 1440 |
| AAAGCAGCGT | GGATCTGGCA | TTCTTTTCCA | CGAATGCACC | 1480 |
| TCAACTACTT | GGCACCAGTG | GTAACACAGC | AACCAGGGTT | 1520 |
| CCGACCTAGA | GAATCCCGTA | ACCTTCTGAC | TGGAACGGGG | 1560 |
| TCTGGGCTGT | CGCTACACAT | CCTGGTGGAA | GGCAGCTATC | 1600 |
| ATCCCTACCT | TCTGCCTTCT | GTCTCTTAAA | TCTGAACCAC | 1640 |
| AAACAGCAAC | GTCCATACCC | TCAGCATTGT | TAGAATCCCC | 1680 |
| TGCAGCCTCC | AGTTCTCATA | CTGTCTGTAT | TCTACTCGCC | 1720 |
| AGTTTGGAGA | GGTCTGGTGG | AGAAAAGGAG | TCTCTTTTCA | 1760 |
| GGCTTGACAA | CAAATAGAAC | TCAGGGCCGG | GCGCGGTGGC | 1800 |
| TCACGCCTGT | CATCCCAGCA | CTGTGGGAGG | CCGAAGCGGG | 1840 |
| CGGATCACCT | GAGGTCGGGA | GCTCAAGACC | AGCCTGGCCA | 1880 |
| ACATGGAGAA | ATCCCATCTT | TACTAAAAAT | ACAAAATTAG | 1920 |
| CCGGGCGTAC | TGGCGAATGC | CTGTAATGCC | AGCTTCTCGG | 1960 |
| GAGGCTGAGG | CAGGAGAATC | GCTTGAACCT | GGGAGGCAGA | 2000 |
| GGTTGCGGTG | AGCCAAGACT | GTGCCACTGT | ACTCCAGCCT | 2040 |
| TGGTGACAGA | GGGAGACTCT | GTCTTAAGAA | AAAAAGAAAA | 2080 |
| AAAAAAAAAA | AGGGCCGGGC | TCACGCCTGT | AATCCCAGCA | 2120 |
| CTTTGGGAGG | CCAAATCACC | TGAGGCCGGG | AGTTTGATAC | 2160 |
| CAACCTGACC | AACATAGTGA | AATCCCGTCT | CTACTAAAAA | 2200 |
| TACAAAATTA | GCCAGGCGTG | GTGGCGGGCG | CCTGTAATCC | 2240 |
| CAGCTACTCG | GGAGGCTGAA | GCAGGAGAAT | CACTTGAACC | 2280 |
| CGGAAGGCGG | AGGTTGCCGT | AAGCCAAGAT | CGCGCCATTG | 2320 |
| CGCTCCAGCC | TGGGCAACAA | GAGTGAAACT | CCATCTCAAA | 2360 |
| AACAAAACAA | AACAAAACAA | AACCAACAAC | TCAGAAGGAG | 2400 |
| GCATATGTGT | TATAAAGTCT | TTACTACAAC | TTTGATTTTA | 2440 |
| TTAGTGGTTG | GTTACTGACT | CTGCCAAGAG | TACAGAATGA | 2480 |
| AGGGCAGAGA | GTAAGGACTG | GAAAACTGGC | AGGAAACACA | 2520 |
| CTGACAGCCG | TCATCCCTGG | AGGAAACTGC | TCAATAAAAC | 2560 |
| GGCTCCATAT | TTACTTCTCT | GGTCACAGTT | CATACTCCAC | 2600 |
| GATTTTAACA | AAGGAGTCGA | GGAAGCTAGA | TACTGTAAGT | 2640 |
| GGAACGGTGT | GTCTCTGGAG | GTAAGCAGGC | TTGCTGATTT | 2680 |
| CTTGTTTTAT | AATTCTTTTT | TAATTACAAT | GTAACTACTA | 2720 |
| AGAGCTTCAG | TTCCCACTGG | AGTGGTGCAC | ACATCTCATT | 2760 |
| ACTACTAAAA | CCACAGGAAT | GTTCCAGGGA | AACAGACTAT | 2800 |

```
CATCACTGAG CGAGGTGGAA TCCAGCCAAA ACCCCAGGCT                2840
AACATCCAGA TGCCTGCATA TCAGCTAAAA TCCTTTTAAA                2880
GGACTTGGAA TCTCCAGATA CTAGTTTTAA GTCTTTTCTG                2920
GGAACTGGGA GTTTGTACTG GAGGCCACTT AACTATTTCA                2960
AAAAATATTC ACCAAAATAG GTGTCTCTCT GACTGCAACG                3000
GTTTGAGTCC TCCTCAGCCC TCATATCCTA GGCTTCGGAC                3040
TGTTGGGAAA GTCTTATCTT CCTGACGAAA GCTCAGCAGC                3080
AACAGAACCT GTTATTTTTT TGTTGAGACA GGGTCTTACT                3120
CTGTCACCCA GGCTGGAGTG CAGTAGTGCG ATCTTGGCTC                3160
ACTGCAGCCT CAGCCTACCA GGCTCAGGTG ACCCTATCTC                3200
AGCTTCTCGA GTAGGTGGGA CTACAGGCAT GTGCCACCAT                3240
GCTCGGTGAA CTAAACAAAC TTTTTGTAG TGATACGGTC                 3280
TCACTATATT GCCCAGGCTG GTTTTGAACT CCTGGGCTCA                3320
AGTGATCCTC CCACCTCAGC GTCTCAAAGT ACTGGGATTA                3360
CAGGTGTGAG CCTCTACACT GGGCCTGCAG AACCTACACA                3400
GAATCCGCAC CTGGTCTGCA GAACCCACAC CCGACCCACA                3440
GAACCCACAC CCGACCCACA GAACCCACAT CTGGCAGCAG                3480
AACCTCTTAG TATTTTTTTT TTTTCTTTGA GATGGAGTCT                3520
GGCTCTGTCA CCCAGGCTGG AGTGCAGTGG CGCGATCTCG                3560
GCTCACTGCA AGCTCTTCCT CCCGGGTTCA CCCCATTCTC                3600
CTGCCTCAAC CTCCCGAGTA GCTGTGAATA CAGGCGTCCG                3640
CCACCACGCC CGACTAATTT TTTTGTATTT TTAGTAGAGA                3680
CGGGGTTTCA CCGTGTTAGC CAGGATGGTC TGGATCTCCT                3720
GACCTCGTGA TCTGCCTGCC TCGGCCTCCC AAAGTGCTGG                3760
GATTACAGGC TTGAGCCACC GCACCCGGCC TCTTATTTTT                3800
TTTTTTGAGA TGGAGTCTCA CACTGTCACC TGGGCTGGAG                3840
TGCAGTGGAG CGATCTCGGC TCACTGCAAC CTCCGCCTCC                3880
TGGGTTCAAG AGATTCTCCT GCCTCAGCCT CCCAAGTAGC                3920
TGGGATTACA GGTGCCCACC ACCACGCCTG GCTAGTTTTT                3960
TGTATTTTTA GTAAAGATGG GGTTTCACCA TGTTGGCCAG                4000
GCTGGTCTTG AACTCCTGAC ATCAGGTGAT CCGCCCACCT                4040
TAGCCTCCCA AAGTGCTGGG ATTACAGGCG TGAGCCACCA                4080
TACCTGGCCA GCAAAACCTC TTTAACTTGT GTTCCATGGG                4120
CTCCTTTTCT GTGGGTCAAA ATCCTCCTGG AACCCTACAA                4160
TGCAGGCCCT ACAGGGGTGG GTGGTAAGTC CAACAAACAG                4200
GATTTCATCT TCTGGAGCTC CTGGATTTCA TCGTCCCATG                4240
GGCCACAGTG CAGCGACAGA ACCTCCTCAG CTTTCTGTAT                4280
TGTGCTCAGG GCTTCGGGTA CTGCAAACCT GAGCCAAGGG                4320
AGGTAAGAGG AGTTAGTTCA CTGATTCGTG AGGCAAATGT                4360
TAATTGAGGG CCTACTCACA CACCGTGAAG AATGTAAGAT                4400
```

| | | | | |
|---|---|---|---|---|
| CATTTCTGTC | ATCAAGGATC | C | | 4421 |

(2) INFORMATION FOR SEQ ID NO:10:

(i) SEQUENCE CHARACTERISTICS:
        (A) LENGTH: 7210 Base Pairs
        (B) TYPE: Nucleic Acid
        (C) STRANDEDNESS: Double
        (D) TOPOLOGY: Unknown (ii) MOLECULE TYPE: Genomic DNA (vi) ORIGINAL SOURCE:
        (A) ORGANISM: Human (vii) IMMEDIATE SOURCE:
        (A) LIBRARY: DASH II (ix) FEATURE:
        (A) NAME/KEY: JT106
        (B) LOCATION:
        (C) IDENTIFICATION METHOD:
        (D) OTHER INFORMATION: 7.2 kb Not 1 fragments
                Derived from human placental genomic DNA (xi) SEQUENCE DESCRIPTION: SEQ ID NO:10:

| | | | | |
|---|---|---|---|---|
| GATCTAGAGC | GGCCGCAGGG | TGGACTGTGC | TGAGGAACCC | 40 |
| TGGGCCCAGC | AGGGGTGGCA | GCCCGCGCAG | TGCCACGTTT | 80 |
| GGCCTCTGGC | CGCTCGCCAG | GCATCCTCCA | CCCCGTGGTC | 120 |
| CCCTCTGACC | TCGCCAGCCC | TCCCCCGGGA | CACCTCCACG | 160 |
| CCAGCCTGGC | TCTGCTCCTG | GCTTCTTCTT | CTCTCTATGC | 200 |
| CTCAGGCAGC | CGGCAACAGG | GCGGCTCAGA | ACAGCGCCAG | 240 |
| CCTCCTGGTT | TGGGAGAAGA | ACTGGCAATT | AGGGAGTTTG | 280 |
| TGGAGCTTCT | AATTACACAC | CAGCCCTCT | GCCAGGAGCT | 320 |
| GGTGCCCGCC | AGCCGGGGGC | AGGCTGCCGG | GAGTACCCAG | 360 |
| CTCCAGCTGG | AGACAGTCAG | TGCCTGAGGA | TTTGGGGGAA | 400 |
| GCAGGTGGGG | AAACCTTGGC | ACAGGGCTGA | CACCTTCCTC | 440 |
| TGTGCCAGAG | CCCAGGAGCT | GGGGCAGCGT | GGGTGACCAT | 480 |
| GTGGGTGGGC | ACGCTTCCCT | GCTGGGGGTG | CAGGGGGTCC | 520 |
| ACGTGGCAGC | GGCCACCTGG | AGCCCTAATG | TGCAGCGGTT | 560 |
| AAGAGCAAGC | CCCTGGAAGT | CAGAGAGGCC | TGGCATGGAG | 600 |
| TCTTGCTTCT | TGCAAACGAG | CCGTGTGGAG | AGAGAGATAG | 640 |
| TAAATCAACA | AAGGGAAATA | CATGGTCTGT | CCGAGGATGA | 680 |
| GCTGCCGGAG | AGCAATGGTG | AAAGTGAAGT | GGGGGAGGGG | 720 |
| GCGGGGCTGG | GAGGAAAAGC | CTTGTGAGAA | GGTGACACGA | 760 |
| GAGCACGGCC | TTGAAGGGGA | AGAAGGAGGG | CACTATGGAG | 800 |
| GTCCCGGCGA | AGCGTGGCCT | GGCCGAGGAA | CGGCATGTGC | 840 |
| AGAGGTCCTG | CCGAGGAGCT | CAAGACAAGT | AGGGGACGGT | 880 |
| GGGGCTGGAG | TGGAGAGAGT | GAGTGGGAGG | AGGAGTAGGA | 920 |
| GTCAGAGAGG | AGCTCAGGAC | AGATCCTTTA | GGCTCTAGGG | 960 |
| ACACGATAAA | CACAGTGTTT | TTTGTCTTGT | CAAGTGTGTC | 1000 |
| CTTTTTATTT | TTTTGAAAGA | GTCTCGCTCT | GTAGCCCAGG | 1040 |

| | | | | |
|---|---|---|---|---|
| CTGGAGTGCA | GCGGTGCGAC | CTCGGCTCAC | TGCAACCTCT | 1080 |
| GCCTCCCGGG | TCCAAGCAAT | TCTCCTGCCT | CAGCCTCCCG | 1120 |
| AGTAGCTGGG | ATTACAGGCA | CCCGCCACCA | CGCACTGCTA | 1160 |
| ATTTTTGTAT | TTTAGTAGAG | ACCGGGTTTT | GCCATGTTGG | 1200 |
| TCAGGCTGGT | CTCGAACTCC | TGACCTCAGG | TGATCCGCCC | 1240 |
| GCCTCGGCCT | CCCAGAGTGG | TGTGAGCCAC | TATGCCCTGC | 1280 |
| AGCACTTGTC | AAGTCTTTCT | CAGCGTTCCC | CTCCTCTCCA | 1320 |
| CTGCAGCTCC | CAGTGCCCCA | GTCTGGGCCT | CGTCTTCACT | 1360 |
| TCCTGGGATC | CCTGACATTG | CCTGCTAGGC | TCTCCCTGTC | 1400 |
| TCTGGTCTGG | CTGCCTTCAC | TGTAACCTCC | ACCCAGCAGG | 1440 |
| TACCTCTTCA | GCACCTCCCA | TGAACCCAGC | AGAATACCAA | 1480 |
| GCCCTGGGGA | TGCAGCAACG | AACAGGTAGA | CGCTGCACTC | 1520 |
| CAGCCTGGGC | GACAGAGCAA | GACTCCGCCT | GAAGAAAAAA | 1560 |
| AAAAGGACCA | GGCCGGGCGC | GGTGGCTCAC | GCCTGTAATC | 1600 |
| CCAGCACTTT | GGGAGGCCGA | GGTGGGTGGA | TCATGAGGTC | 1640 |
| AGGAGTTCAA | GACCAGCCTG | GCCAAAATGG | TGAAACCCCG | 1680 |
| TCTCTACTGA | AAAATACAAA | AATTAGCTGG | GTGCAGTGGC | 1720 |
| GGGCGCCTGT | AGTCTCAGCT | ACTCAGGAGG | CTGAGGCAGG | 1760 |
| ATAATTGCTT | GACCCCAGGA | GGCAGAGGTT | GCAGTGAACC | 1800 |
| GAGATCACGC | CACTGCACTC | CAGCCTGGGC | GACAGAGCAA | 1840 |
| GACTCTGCCT | CAAAAAAAAG | AATAAAAATA | AAAAAAGGA | 1880 |
| CCAGATACAG | AAAACAGAAG | GAGACGTACT | ATGAAGGAAA | 1920 |
| TTGGAGAGCT | TTTGGGATAC | TGAGTAACTC | AGGGTGGCCT | 1960 |
| TTCCCAGGGG | ACATTTAGCT | GAGAGATAGA | CGGTATGAAG | 2000 |
| ACCTGACCGT | TCAGAAACAG | GGGAAGAGGC | AGCAGCCCGG | 2040 |
| GCAAAGGCCT | TTGGGGCAGG | AAAGGGCTTG | GATCACTGGA | 2080 |
| GAAGCAGAAA | GATGGCCAGT | GTGACCAGAG | TGTGACAAAG | 2120 |
| TCAGAGAAAA | CCAGGAAGAT | GGAGCTGGAG | ACACAGGCGG | 2160 |
| GGCCAGATCA | CGAGGGTCCT | CGCAGACCAG | AGCAAGGGTT | 2200 |
| TGGATTTTAT | TCCAAGTATG | AAGGGAAGCT | GCTGAAGTGT | 2240 |
| GTTTTCCTTT | ACAATTTGTA | GTTGAAATAT | AATATGCAAA | 2280 |
| GTACACAAGT | CTTAACTATA | TGTAAGCTTA | ATGAATGTTT | 2320 |
| CCATGAACCA | AATACCGCTG | TGCAACCATC | ACCAGCTCAA | 2360 |
| GAGACGAACC | CTTCTCCCTC | CTCCTGACTG | CCAGTAACAT | 2400 |
| AGTGGTTCAG | CTCAAGAAAC | AGAACTCTTC | TGACTTCCCC | 2440 |
| TAACATAGCG | GGTTTTCTTT | TTTGTTTGT | TTTTGTTGT | 2480 |
| TTTTAAGAG | ACAATGTCTT | TATTATTTTT | ATTTTTTTT | 2520 |
| ATTTTTGAGA | CGGAGTCTTG | CTGTCGCCCA | GGCTGGAGTG | 2560 |
| CAGTGGTGCG | ATCTCGGCTC | ACTGCAGGCT | CTGCCCCCCG | 2600 |
| GGGTTCATGC | CATTCTCCTG | CCTCAGCCTC | CCTAGCAGCT | 2640 |

```
GGGACTACAG GTGCCCGCCA CCTCGCCCGG CTATTTTTTT           2680

GTATTTTTAG TGGAGACGGG GTTTCACCGT GTTAGCCAGG           2720

ATGGTCTCGA TCTCCTGACC TCGTGATCCG CCCACCTCGG           2760

CCTCCCAAAG TGCTGGGATT ACAGGCATGA GCCACCGCGC           2800

CCAGCCAAGA GACACGGTCT TGCTCTGTCG CCCAGGCTGG           2840

ATGGAGTGCC GTGGTGCGAT CACAGCTCGC GGCAGCCTTG           2880

ACATCCTGGG CTCAAGCAAC CTTCCTGCCT TGGCCTCCCA           2920

AATGTTGGGA TTATAGGCAT GAGCCACTGT GCTTGGCATC           2960

TATTCATCTT TAATGTCAAG CAGGCAATTG AATATTTGAT           3000

CAGGGATAGA ATTGTCTATT TGGGGGTATG CAGATGTGCT           3040

TCATGTCATG GAACTGGGCC GGGCGCGGTG GCTCATGCCT           3080

ATAATCCCAG CACTTTGGGA GGCCGAGGCA GGCGGATCAT           3120

AAGGTCAGGA GATCGAGACC ATCCGGGCCA ACACGGTGAA           3160

ACCCCGTCTC TACTAAAAAT ACAAAAATTA GCCAGGTGTG           3200

GTGGTGCGTG CCTGTAGTCC CAGCTACTCA GGGAGGCTGA           3240

GACAGGAGAA TTGATTGAAC CTGGGAGGCA GAGGTTGTAG           3280

TGAGCCAAGA TCGCGCCACT GCACTCCAGC CTGGGCGACA           3320

TGAGCGAGAC TCCGTCTCAA AAATAAACAA AAAAAAGTCA           3360

TGGAATTGAT GGAAATTGCC TAAGGGGAGA TGTAGAAGAA           3400

AAGGGGTCTC AGGATCAAGC CAGCAGAGAA GGCAGAAAAG           3440

GTAAGGTGTG TGAGGTGGCA GAAAAAGGGA AGAGTGTGGA           3480

CAGTGAGGGT TTCAAGGAGG AGGAACTGTC TACTGCCTCC           3520

TGCCAAGGAC GGAGGTGTCC ACTGCCAGTT GACATAAGGT           3560

CACCCATGAA CTTGGTGACA GGAATTTCAG TGGAGAAGTG           3600

GCCACAGACA CAAGTCTAGA ATTGAAATGG GAGCCGAGGC           3640

AGCGTAGACA AAAGAGGAAA CTGCTCCTTC CAGAGCGGCT           3680

CTGAGCGAGC ACCGAGAAAT GGGCAGTGGC TTTAGGGGAT           3720

GTAGCGTCAA GGAAGTGTCT TTTAAAGAAG TCGGGGGCCG           3760

GGCACGGTGG CTCACGCCTG TAGTCCCAGC ACTTTGGGAG           3800

GCCGAGGCAG GCAGATCACT TGAGGTCAGG AGTTCGAGAC           3840

CAGCCTGGCT AACACGATGA AACCCCGTCT CTACTAAAAA           3880

TACAAAAAAT TAGCTGGGCA CGGTGGCTCG TGCCTGTAAT           3920

CCCAGCACTT TGGGAGGCAG AGGTGGGCAG ATCACTTGAG           3960

GTCAGGAGTT TGAGACCAGC CTAGCCAACA TGGTGAAACC           4000

CCATCTCTAC TAAAACTACA AAAATTAGCC GGGAGTGGTG           4040

GCACGTGCCT GTAATCCCAG CCAGTCAGGA GGCTGAGGCA           4080

GGAGAATCAC TGGAATCCTG GAGGTGGAGG TGGCAGTGAG           4120

CCGAGATGGT ACCTCTGTAC TCCAGCCTGG GGACAGAGT            4160

GAGACTCCGT CTCAAAAAAA AAAGAAGGTG GGAAGGATC            4200

TTTGAGGGCC GGACACGCTG ACCCTGCAGG AGAGGACACA           4240
```

```
TTCTTCTAAC  AGGGGTCGGA  CAAAAGAGAA  CTCTTCTGTA        4280

TAATTTATGA  TTTTAAGATT  TTTATTTATT  ATTATTTTTT        4320

ATAGAGGCAA  GCATTTTTCA  CCACGTCACC  CAGGCTGGTC        4360

TCCAACTCCT  GGGCTCAAGT  GTGCTGGGAT  TATAGCCATG        4400

AGTCACCACA  CCTGGCCCAG  AAACTTTACT  AAGGACTTAT        4440

TTAAATGATT  TGCTTATTTG  TGAATAGGTA  TTTTGTTCAC        4480

GTGGTTCACA  ACTCAAAAGC  AACAAAAAGC  ACCCAGTGAA        4520

AAGCCTTCCT  CTCATTCTGA  TTTCCAGTCA  CTGGATTCTA        4560

CTCTTGGGAT  GCAGTGTTTT  TCATCTCTTT  TTTGTATCCT        4600

TTTGGAAATA  GTATTCTGCT  TTAAAAGCA   AATACAGGCC        4640

AGGTATGGTG  GCTCACTCCT  GTAATCCCAG  CACTTTGGGA        4680

GCCGAGGCAG  GTGATCACCT  AAGGTCAGGA  GTTCAAGACC        4720

AGCCTGGCCA  ATATGGTGAA  ACCCTGTCTG  TACCAAAACA        4760

CAAAACAAA   AACAAAAACA  AAAATTAGCC  GGGCGTGGTG        4800

GCGTGCTCCT  GTAATCCCAG  CTACTCAGGA  GGCTGAGGCA        4840

GGAGAATCGC  TTGAACCTGG  GAGGCAGAGG  TTGCAGTGAG        4880

CCGAGATTGT  GCCACTGTAC  TCCAGCCTGG  GCCACAGAGC        4920

AAGGTTCCAT  CTCAAACAAA  ACAAAACAAA  ACAAACAAAA        4960

AAACAAAACA  AAAGCTAATA  CAAACACATA  TACAATAGAC        5000

AAAACTGTAA  ATATTTTATT  ATTTTTATTT  TTTTAGTAG         5040

AGACAGGGTT  TCACCATGTT  GGCCAGGATG  GTCTCAAACT        5080

CCTGACCTCA  GGTGATCCAC  CCACCTCAGC  CTCCCGATAG        5120

TTAGGATTAC  AGGCATGAGC  CACCACACCC  GGCCTAAAAT        5160

TGTAAACGTT  TTAGAAGAAA  GTATAGATGA  ATCCCTTCGT        5200

GATCTCGGGG  AAGAAGAGAT  TTTTTAAAAA  AGATACCAAA        5240

AGAAGCACAA  ATTATAAAAG  AAAAGATTGA  AAATGTTGGT        5280

GTTAAAATTA  AAAACTTGTT  TTAAAACAAG  CTTGTGTAAC        5320

CCATGACCCA  CAGGCTGCAT  GTGGCCCAGA  AAAGCTTTGA        5360

CTGCAGCCCA  ACACAAATTC  GTAAACTTTC  CTAAAACATT        5400

ATGAGATTTT  TTTTGAGATT  TTGTTTTGTT  TTGTTTTTTG        5440

TTTTTTTAGC  TCATTCGGTA  TCATTAATGT  TAGCATATTT        5480

TACGTGGGGC  CCAAGACAAT  TCTTCTTCCA  ATGTGTCTCA        5520

GGGGAGCCAA  AAGATTGGAC  ACCCCTGCCA  TAAACATGAA        5560

AAGACAATGG  CCGGGCACGG  TGGCTCACGC  CTGTAATCCC        5600

AGCACTTTGG  GAGGCTGAGG  GGGGCGGGAT  CACCTGAGGT        5640

CAGGAGTTTG  AGACAAGCGT  GACCAATGTG  GTGAAACCCT        5680

GTCTCTACTA  AAAATACAAA  AATTAGCCGG  GCATGCTCGT        5720

GCACACCTAT  AGTCCCAACT  ACTCAGCAGG  GTGAGGCAGG        5760

AGAACCTCTT  GAACCCGGGA  AGCGGAGGTT  GCAGTGAGCC        5800

GACATTGCAC  CCCTGCACTC  CAGCCTGGGT  GACAGAGTGA        5840
```

| | | | | |
|---|---|---|---|---|
| GTCTCCACTG | GAAAAAAAAA | AAAAAGAACA | GTGTGATACA | 5880 |
| TTGACCTAAG | GTTTAAGAAC | ATGCAAACTG | ATACTATATA | 5920 |
| TCACTTAGGG | ACAAAAACTT | ACATGGTAAA | AGTAAAAAGA | 5960 |
| AATGTACGAA | AATAATAAAA | ATCAAATTCA | AGATGGTGGT | 6000 |
| TATGGTGACG | GGAAAGAACT | GAGGCGGAAA | TATAAGGTTG | 6040 |
| TCACTATATT | GAGAAATTTT | TCTATCTTTT | TTTCTTTTTT | 6080 |
| CTTTTTTTGA | GACGGGGTCT | CGCTCTGTCG | CCCAGGATGG | 6120 |
| AGTGCAGTGG | TGTGATCTCA | GCTCACTGCA | ACCTCCGCCT | 6160 |
| CCCAGGTTTA | AGTGATTCTC | CTGCCTCAGA | CTCCCAAGTA | 6200 |
| GCTGGGACTA | CAGGTGCGCG | CCAACACACC | TGGGTAATTT | 6240 |
| TGTTTGTATT | TTTAGTAGAG | ATGGGGTTTC | ACCGTGTTGA | 6280 |
| CTAGGCTGGT | CTCGAACTCC | TGACCTCAGG | TGATCCCCCG | 6320 |
| GCCTCGGTCT | CCCAAAGTGC | TGGGATAACA | AGCGTGAGCC | 6360 |
| ACTGCGCCCA | GCTTTGTTTG | CATTTTTAGG | TGAGATGGGG | 6400 |
| TTTCACCACG | TTGGCCAGGC | TGGTCTTGAA | CTCCTGACCT | 6440 |
| CAGGTGATGC | ACCTGCCTCA | GTCTCCCAAA | GTGCTGGATT | 6480 |
| ACAGGCGTTA | GCCCCTGCGC | CCGGCCCCTG | AAGGAAAATC | 6520 |
| TAAAGGAAGA | GGAAGGTGTG | CAAATGTGTG | CGCCTTAGGC | 6560 |
| GTAATGGATG | GTGGTGCAGC | AGTGGGTTAA | AGTTAACACG | 6600 |
| AGACAGTGAT | GCAATCACAG | AATCCAAATT | GAGTGCAGGT | 6640 |
| CGCTTTAAGA | AAGGAGTAGC | TGTAATCTGA | AGCCTGCTGG | 6680 |
| ACGCTGGATT | AGAAGGCAGC | AAAAAAAGCT | CTGTGCTGGC | 6720 |
| TGGAGCCCCC | TCAGTGTGCA | GGCTTAGAGG | GACTAGGCTG | 6760 |
| GGTGTGGAGC | TGCAGCGTAT | CCACAGGTAA | AGCAGCTCCC | 6800 |
| CTGGCTGCTC | TGATGCCAGG | GACGGCGGGA | GAGGCTCCCC | 6840 |
| TGGGCTGGGG | GGACAGGGGA | GAGGCAGGGG | CACTCCAGGG | 6880 |
| AGCAGAAAAG | AGGGGTGCAA | GGGAGAGGAA | ATGCGGAGAC | 6920 |
| AGCAGCCCCT | GCAATTTGGG | CAAAAGGGTG | AGTGGATGAG | 6960 |
| AGAGGGCAGA | GGGAGCTGGG | GGGACAAGGC | CGAAGGCCAG | 7000 |
| GACCCAGTGA | TCCCCAAATC | CCACTGCACC | GACGGAAGAG | 7040 |
| GCTGGAAAGG | CTTTTGAATG | AAGTGAGTGG | GAAACAGCGG | 7080 |
| AGGGGCGGTC | ATGGGGAGGA | AAGGGGAGCT | AAGCTGCTGG | 7120 |
| GTCGGGTCTG | AGCAGCACCC | CAAGACTGGA | GCCCGAGGCA | 7160 |
| AGGAGGCTCA | CGGGAGCTGC | TTCCACCAAG | GGCAGTCAGG | 7200 |
| AAGGCGGCCG | | | | 7210 |

( 2 ) INFORMATION FOR SEQ ID NO:11:

( i ) SEQUENCE CHARACTERISTICS:
        ( A ) LENGTH: 1988 Base Pairs
        ( B ) TYPE: Nucleic Acid
        ( C ) STRANDEDNESS: Double
        ( D ) TOPOLOGY: Unknown ( i i ) MOLECULE TYPE: Genomic DNA ( v i ) ORIGINAL SOURCE:
    ( A ) ORGANISM: Human ( i x ) FEATURE:
    ( A ) NAME/KEY: JT108
    ( B ) LOCATION:
    ( C ) IDENTIFICATION METHOD:
    ( D ) OTHER INFORMATION: 2 kb PCR product using primers, SEQ ID: 13 and 14.

( x i ) SEQUENCE DESCRIPTION: SEQ ID NO:11:

| | | | | |
|---|---|---|---|---|
| ACAAGCTGGC | AGCGGCTGTC | TCCAACTTCG | GCTATGACCT | 40 |
| GTACCGGGTG | CGATCCAGCA | NGAGCCCCAC | GACCAACGTG | 80 |
| CTCCTGTCTC | CTCTCAGTGT | GGCCACGGCC | CTCTCGGCCC | 120 |
| TCTCGCTGGG | TGAGTGCTCA | GATGCAGGAA | GCCCCAGGCA | 160 |
| GACCTGGAGA | GGCCCCCTGT | GGCCTCTGCG | TAAACGTGGC | 200 |
| TGAGTTTATT | GACATTTCAG | TTCAGCGAGG | GGTGAAGTAG | 240 |
| CACCAGGGGC | CTGGCCTGGG | GGTCCCAGCT | GTGTAAGCAG | 280 |
| GAGCTCAGGG | GCTGCACACA | CACGATTCCC | CAGCTCCCCG | 320 |
| AAAGGGGCTG | GGCACCACTG | ACATGGCGCT | TGGCCTCAGG | 360 |
| GTTCGCTTAT | TGACACAGTG | ACTTCAAGGC | ACATTCTTGC | 400 |
| ATTCCTTAAC | CAAGCTGGTG | CTAGCCTAGG | TTCCTGGGAT | 440 |
| GTAACTGCAA | ACAAGCAGGT | GTGGGCTTGC | CCTCACCGAG | 480 |
| GACACAGCTG | GGTTCACAGG | GGAACTAATA | CCAGCTCACT | 520 |
| ACAGAATAGT | CTTTTTTTTT | TNTTTTTTTN | NNCTTTCTGA | 560 |
| GACGGAGTCT | CGCTTTGTCN | CCAAGGCTGG | AGTGCAGTGG | 600 |
| TGTGATCTCA | GCTCACTGCA | ACCTCTGCCT | CCCTGGTTCA | 640 |
| AGGAATTCTC | CTGCCTCAGC | CTCCAGAGTA | GCTGGGATTA | 680 |
| CAGGCACCTG | CCATCATGCC | CAGCTAATTT | TTGTATTTTT | 720 |
| AGTAGAGACG | GGGTTTCACC | ATGTTGCCTA | GGCTGGTCTC | 760 |
| AAACTCCCGG | GCTCAAGCGA | TCCACCCGCC | TTGGCCTCCC | 800 |
| AAAGTGCTGG | GATTACAGGC | GTGAGCCACC | GCGCCTGGCC | 840 |
| AGAATAATCT | TAAGGGCTAT | GATGGGAGAA | GTACAGGGAC | 880 |
| TGGTACCTCT | CACTCCCTCA | CTCCCACCTT | CCAGGCCTGA | 920 |
| TGCCTTTAAC | CTACTTCAGG | AAAATCTCTA | AGGATGAANA | 960 |
| TTCCTTGGCC | ACCTAGATTG | TCTTGAAGAT | CAGCCTACTT | 1000 |
| GGGCTCTCAG | CAGACAAAAA | AGATGAGTAT | AGTGTCTGTG | 1040 |
| TTCTGGGAGG | GGGCTTGATT | TGGGGCCCTG | GTGTGCAGTT | 1080 |
| ATCAACGTCC | ACATCCTTGT | CTCTGGCAGG | AGCGGAGCAG | 1120 |
| CGAACAGAAT | CCATCATTCA | CCGGGCTCTC | TACTATGACT | 1160 |
| TGATCAGCAG | CCCAGACATC | CATGGTACCT | ATAAGGAGCT | 1200 |
| CCTTGACACG | GTCACTGCCC | CCCAGAAGAA | CCTCAAGAGT | 1240 |
| GCCTCCCGGA | TCGTCTTTGA | GAAGAGTGAG | TCGCCTTTGC | 1280 |
| AGCCCAAGTT | GCCTGAGGCA | TGNGGGNTCC | ATGCTGCAGG | 1320 |

| | | | | |
|---|---|---|---|---|
| CTGGGGGGGT | CTTTTTTTTT | TTTTNNNNA | GACGGAGTCT | 1360 |
| CGCTCTGTTG | CCCAGGCTGG | AGTGCAGTGG | CGNGATCTCG | 1400 |
| GCTCACTGCA | ACCTCCACCT | CCCGGGTTCA | CACCATCCTC | 1440 |
| CTGCCTCAGC | CTCCCGAGTA | GCTGGGACTG | CAGGNGCCCA | 1480 |
| GCTAATCTTT | NTTGTATTTT | TAGCAGAGAC | GGGGTTTCAC | 1520 |
| CGTGTTTGCC | AGGATAGTCT | CGATCTCCTG | ACCTGGTGTT | 1560 |
| CTGCCCGCCT | CGACCTCCCA | AAGTGCTGGG | ATTACAGGTG | 1600 |
| TGAGCCACCG | CGCTCGGCCC | GTTTCTAAAC | AATAGATCAT | 1640 |
| GTGTGCCCAG | GCCTGGCCTG | GCACTGGTGT | GGAGGAAGGG | 1680 |
| CCCGTGAGCC | CAAAGAGGCT | CAGAAAGAGG | AAGTGGGCTG | 1720 |
| CAGGAGACGG | TGGGAGGGGC | NGGGAGGGCA | GTGGCGCGAT | 1760 |
| GTGGGGAAAT | CTGCTGCCCC | CCTGGCCAGT | GCCTGGGGAT | 1800 |
| GCCAGCAGAA | GTCCTGGCAA | GTCACAGGAA | GATGCTGGCT | 1840 |
| GGGAAGTCAG | GGCCTGCTGA | GCGCTAAACC | AGAACCCGAG | 1880 |
| CCTGGCAGGC | TCTCAAAGAC | GGGATGCTTG | TCGTNGAGTC | 1920 |
| TCATANGCTA | ACCTCTGCTC | CGCCTCTTCT | CAGAGCTGCG | 1960 |
| CATAAAATCC | AGCTTTGTGG | CACCTCTG | | 1988 |

( 2 ) INFORMATION FOR SEQ ID NO:12:

( i ) SEQUENCE CHARACTERISTICS:
            ( A ) LENGTH: 3267 Base Pairs
            ( B ) TYPE: Nucleic Acid
            ( C ) STRANDEDNESS: Double
            ( D ) TOPOLOGY: Unknown ( i i ) MOLECULE TYPE: Genomic DNA ( i x ) FEATURE:
            ( A ) NAME/KEY: JT109
            ( B ) LOCATION:
            ( C ) IDENTIFICATION METHOD:
            ( D ) OTHER INFORMATION: 3.3 kb PCR product
                  using primers, SEQ ID No: 15 and 16

( x i ) SEQUENCE DESCRIPTION: SEQ ID NO:12:

| | | | | |
|---|---|---|---|---|
| GATTCCAGCT | TTGTGGCACC | TCTGGAAAAG | TCATATGGGA | 40 |
| CCAGGCCCAG | AGTCCTGACG | GGCAACCCTC | GCTTGGACCT | 80 |
| GCAAGAGATC | AACAACTGGG | TGCAGGCGCA | GATGAAAGGG | 120 |
| AAGCTCGCCA | GGTCCACAAA | GGAAATTCCC | GATGAGATCA | 160 |
| GCATTCTCCT | TCTCGGTGTG | GCGCACTTCA | AGGGTGAGCG | 200 |
| CGTCTCCAAT | TCTTTTTCAT | TTATTTTACT | GTATTTTAAC | 240 |
| TAATTAATTA | ATTCGATGGA | GTCTTACTCT | GTAGCCCTAA | 280 |
| CTGGAGTGCA | GTGGTGCGAT | CTCAGCTCAA | TGCAACCTCC | 320 |
| GCCTCCCAGG | TTCAAGCAAT | TCTTGTGCCT | CAGCCTCCCG | 360 |
| AGTAGCTGGG | ATTACAGGGA | TGTACCACCA | CTCCCGGCTA | 400 |
| ATTTTTTGTA | TTTAATAGAC | ATGGGGTTTC | ACCATGTTGG | 440 |
| CCAGGCTGGT | CTCGAACTCC | TGAGCTCAGG | TGGTCTGCCC | 480 |
| GCCTCAGCCT | CCCAAAGTGC | TAGGATTACA | AGCTTGAGCC | 520 |

| | | | | |
|---|---|---|---|---:|
| ACCACGCCCA | GCCCTTTTTA | TTTTTAAATT | AAGAGACAAG | 560 |
| GTGTTGCCAT | GATGCCCAGG | CTGGTCTCGA | ACTCCTGGGC | 600 |
| TCAAGTAATC | CTCCCACCTT | GGCCTCCCAA | AGTGCTGGGA | 640 |
| TTACAGGCAT | GAGCCACCGC | GCCCGGCCCT | TTTACATTTA | 680 |
| TTTATTTATT | TTTTGAGACA | GAGTCTTGCT | CTGTCACCCA | 720 |
| GGCTGGAGTG | CAGTGGCGCG | ATCTCGGCTC | ACTGCAAGCT | 760 |
| CTGCCTTCCA | GGTTCACACC | ATTCTCCTGC | CTCGACCTCC | 800 |
| CGAGTAGCTG | GGACTACAGG | CGCCCGCCAC | TGCGCCCTAC | 840 |
| TAATTTTTTG | TATTTTTAGT | AGAGACGGGG | TTTCACCGTG | 880 |
| GTCTCGATCT | CCTGACCTCG | TGATCCACCC | GCCTCAGCCT | 920 |
| CCCAAAGTGC | TGGGATTACA | GGCGTGAGCC | ACTGCGCCCG | 960 |
| GCCCTTTTAC | ATTTATTTTT | AAATTAAGAG | ACAGGGTGTC | 1000 |
| ACTATGATGC | CGAGGCTGGT | CTCGAACTCC | TGAGCTGAAG | 1040 |
| TGATCCTCCC | ACCTCGGCCT | CCCAAAATGC | TGGGATTACC | 1080 |
| ATGTCCAACT | TTCCACTTCT | TGTTTGACCA | AGGATGGATG | 1120 |
| GCAGACATCA | GAAGGGCTT | GGAAAGGGAG | GTGTCAAAGA | 1160 |
| CCTTGCCCAG | CATGGAGTCT | GGGTCACAGC | TGGGGGAGGA | 1200 |
| TCTGGGAACT | GTGCTTGCCT | GAAGCTTACC | TGCTTGTCAT | 1240 |
| CAAATCCAAG | GCAAGGCGTG | AATGTCTATA | GAGTGAGAGA | 1280 |
| CTTGTGGAGA | CAGAAGAGCA | GAGAGGGAGG | AAGAATGAAC | 1320 |
| CTGGGTCTGT | TTGGGGCTTT | CCCAGCTTTT | GAGTCAGACA | 1360 |
| AGATTTATTT | ATTTATTTAA | GATGGAGTCT | CATTCTGTTG | 1400 |
| CCCAGGCTGG | AGTGCAGTGG | TGCCATCTTG | GCTCACTACA | 1440 |
| GCCTCCCCAC | CTCCCAGGTT | CAAGTGCTTC | TCCTGCCTCA | 1480 |
| GCCTCCCGAG | TAGTTGGGAT | TACAGGCGCC | CGCCACCACA | 1520 |
| CCCAGCTAAT | TTTTGTATTT | TCAGTAGAGA | TGGGGTTTCG | 1560 |
| CCATGCTGGC | CAGGCTGTTC | TCGAAAACTC | CTGACCTCAG | 1600 |
| ATGATCCACC | CGCCTCGGCC | TCCCACAGTG | CTGGGATTAC | 1640 |
| AGGCGTGAGC | CACTGCGCTG | GCCAAATCAG | ACAAGGTTTA | 1680 |
| AATCCCAGCT | CTGCCTGTAC | TAGCTGAGGA | ACTCTGCACA | 1720 |
| CATTTCATAA | CCTTTCTGGG | CCTACGTTCT | CACCTTTAAC | 1760 |
| GTGAGGATAA | TATATCTACT | TCATAGACAC | CTTTTTATGT | 1800 |
| TGTCTCCAAG | TTTTCTAACA | GCTCTAGTTC | TGTACCCAAG | 1840 |
| ACATGGCAGG | TGGCCAACGA | CATCCTTCTA | GGCTGTGGTG | 1880 |
| ATGTGTTTGG | AGCTTGTTCC | ACGGGTCTTG | TGTGGGGCCA | 1920 |
| GCCCTGTTCA | GATAAGGCCT | TGTGGGGTGG | CCTGGGGTAG | 1960 |
| GGGGAGGGGT | TGGGCAAACT | CTCCCTTAAA | ACGCTTTGTA | 2000 |
| ACCATCTGAG | GCACCAGCAA | GAGCGGCCCC | CGAGCCTGGA | 2040 |
| CAAAATCCAA | ACGGCTTCCT | ACTTCAAGCA | CTGATGTCTA | 2080 |
| GTGAGTGAAG | GAACAGCTCT | GGGTCCAGGA | TATTATAGGT | 2120 |

| | | | | |
|---|---|---|---|---|
| CACATTAAAC | TAAAGGGGCT | TGGCCATCAG | CTGGCTTCCA | 2160 |
| GAGCGTCAGC | CAGTTACTTC | ACCTCTTTGG | CTTTGGCCTG | 2200 |
| TTTTCAGCTA | CAAGAGGACT | TAATCCAGAG | GACCTCAGAG | 2240 |
| GTCCTTCCCA | GCTCAGACCT | TCTTTGACTG | TCTCCCAGAG | 2280 |
| ACACTGCTGT | AGGAGTGCAC | ACCAGTTAC | TTTTCTTTCT | 2320 |
| TTTGTTTTTG | AGATGGAGTT | TCGCTCTTTT | TGCCTAGGCT | 2360 |
| GGAGTGCTGT | GGTGTGATCT | CAGCTCACTG | CAACCTCTGG | 2400 |
| CTCCCAGGTT | CAAGTGATTC | TCCTGTCTCT | GCCTCCCGAG | 2440 |
| TAGCTGGGAT | TACAGACACC | CACCACTGCA | CCCGGCTAGT | 2480 |
| TTTTGTATTT | TCAGTAGAGA | TGGGGTTTCG | CCATGCTGGC | 2520 |
| CAGGCTGTTC | TCGAAAACTC | CTGACCTCAG | ATGATCCATC | 2560 |
| CGCCTTGGCC | TCCCAAAGTG | CTGAGATTAC | AGATGTGAGG | 2600 |
| CACCACACCC | GGCCATTTTT | GTATTTTAG | TAGAGACGGG | 2640 |
| GTTTTGCCAT | GTTGGCCACG | CTGGTCTCAA | ACTCCTGACC | 2680 |
| TCAAGTGATC | TGCCCACCTT | GGCCTCCTGA | AGGGCTGGGA | 2720 |
| CTACAGGCGT | GAGTCACCGT | GCCCGGCCAT | TTTTGTATTT | 2760 |
| TTAGGACAGC | GTTTTTTCAT | GTTGGCCAGG | CTGGTCTCAA | 2800 |
| ACTCCTGACC | TCAAGTGATC | CACCCACCCC | GGCCTCCCAA | 2840 |
| TATGCTGGGA | TTCCAGGTGT | GAGTTACCAT | GCCCGGCTAC | 2880 |
| CACTTTACTT | TTCCTGCAGG | CTATCACAGA | ACGTGTACAA | 2920 |
| TCTAGACTCT | AATCAACCAA | ATCAACGTCT | TGCCATCGGA | 2960 |
| GTTTGCTGGT | GAAGGGCACT | TGGGGTCCTG | GAAATAACTG | 3000 |
| TAGGCTCCAA | GCCACACACA | CTGAGATAGG | CCTATTCCCT | 3040 |
| GAGGCCTCAG | AGCCCCTGAC | AGCTAAGCTC | CCTTGAGTCG | 3080 |
| GGCAATTTTC | AACAACGTGC | TCTGGGGACA | CAGCATGGCG | 3120 |
| CCACTGTCTT | TCTGGTCTCC | TGGGGCTCAG | ACTATGTCAT | 3160 |
| ACACTTCTTT | CCAGGGCAGT | GGGTAACAAA | GTTTGACTCC | 3200 |
| AGAAAGACTT | CCCTCGAGGA | TTTCTACTTG | GATGAAGAGA | 3240 |
| GGACCGTGAG | GGTCCCCATG | ATGAATC | | 3267 |

( 2 ) INFORMATION FOR SEQ ID NO:13:

( i ) SEQUENCE CHARACTERISTICS:
        ( A ) LENGTH: 20 Base Pairs
        ( B ) TYPE: Nucleic Acid
        ( C ) STRANDEDNESS: Unkown
        ( D ) TOPOLOGY: Unknown ( i i ) MOLECULE TYPE: Oligonucleotide ( i x ) FEATURE:
        ( A ) NAME/KEY: 603
        ( B ) LOCATION:
        ( C ) IDENTIFICATION METHOD:
        ( D ) OTHER INFORMATION: primer in a polymerase
            chain reaction ( x i ) SEQUENCE DESCRIPTION: SEQ ID NO:13:

ACAAGCTGGC AGCGGCTGTC        20

( 2 ) INFORMATION FOR SEQ ID NO:14:

( i ) SEQUENCE CHARACTERISTICS:
        ( A ) LENGTH: 20 Base Pairs
        ( B ) TYPE: Nucleic Acid
        ( C ) STRANDEDNESS: Unkown
        ( D ) TOPOLOGY: Unknown ( i i ) MOLECULE TYPE: Oligonucleotides ( i x ) FEATURE:
        ( A ) NAME/KEY: 604
        ( B ) LOCATION:
        ( C ) IDENTIFICATION METHOD:
        ( D ) OTHER INFORMATION: primer in a polymerase
              chain reaction ( x i ) SEQUENCE DESCRIPTION: SEQ ID NO:14:

CAGAGGTGCC ACAAAGCTGG        20

( 2 ) INFORMATION FOR SEQ ID NO:15:

( i ) SEQUENCE CHARACTERISTICS:
        ( A ) LENGTH: 20 Base Pairs
        ( B ) TYPE: Nucleic Acid
        ( C ) STRANDEDNESS: Unkown
        ( D ) TOPOLOGY: Unknown ( i i ) MOLECULE TYPE: Oligonucleotides ( i x ) FEATURE:
        ( A ) NAME/KEY: 605
        ( B ) LOCATION:
        ( C ) IDENTIFICATION METHOD:
        ( D ) OTHER INFORMATION: primer in a polymerase
              chain reaction ( x i ) SEQUENCE DESCRIPTION: SEQ ID NO:15:

CCAGCTTTGT GGCACCTCTG        20

( 2 ) INFORMATION FOR SEQ ID NO:16:

( i ) SEQUENCE CHARACTERISTICS:
        ( A ) LENGTH: 20 Base Pairs
        ( B ) TYPE: Nucleic Acid
        ( C ) STRANDEDNESS: Unknown
        ( D ) TOPOLOGY: Unknown ( i i ) MOLECULE TYPE: Oligonucleotide ( i x ) FEATURE:
        ( A ) NAME/KEY: 606
        ( B ) LOCATION:
        ( C ) IDENTIFICATION METHOD:
        ( D ) OTHER INFORMATION: primer in a polymerase
              chain reaction ( x i ) SEQUENCE DESCRIPTION: SEQ ID NO:16:

CATCATGGGG ACCCTCACGG        20

( 2 ) INFORMATION FOR SEQ ID NO:17:

( i ) SEQUENCE CHARACTERISTICS:
        ( A ) LENGTH: 20 Base Pairs
        ( B ) TYPE: Nucleic Acid
        ( C ) STRANDEDNESS: Unknown
        ( D ) TOPOLOGY: Unknown ( i i ) MOLECULE TYPE: Oligonucleotide ( i x ) FEATURE:
        ( A ) NAME/KEY: 2213
        ( B ) LOCATION:

(C) IDENTIFICATION METHOD:
(D) OTHER INFORMATION: primer in a polymerase
      chain reaction (xi) SEQUENCE DESCRIPTION: SEQ ID NO:17:

AGGATGCAGG CCCTGGTGCT                    20

(2) INFORMATION FOR SEQ ID NO:18:

(i) SEQUENCE CHARACTERISTICS:
        (A) LENGTH: 20 Base Pairs
        (B) TYPE: Nucleic Acid
        (C) STRANDEDNESS: Unknown
        (D) TOPOLOGY: Unknown (ii) MOLECULE TYPE: Oligonucleotide (ix) FEATURE:
        (A) NAME/KEY: 2744
        (B) LOCATION:
        (C) IDENTIFICATION METHOD:
        (D) OTHER INFORMATION: primer in a polymerase
              chain reaction (xi) SEQUENCE DESCRIPTION: SEQ ID NO:18:

CCTCCTCCAC CAGCGCCCCT                    20

(2) INFORMATION FOR SEQ ID NO:19:

(i) SEQUENCE CHARACTERISTICS:
        (A) LENGTH: 24 Base Pairs
        (B) TYPE: Nucleic Acid
        (C) STRANDEDNESS: Uknown
        (D) TOPOLOGY: Unknown (ii) MOLECULE TYPE: Oligonucleotide (ix) FEATURE:
        (A) NAME/KEY: 2238
        (B) LOCATION:
        (C) IDENTIFICATION METHOD:
        (D) OTHER INFORMATION: primer in a polymerase
              chain reaction (xi) SEQUENCE DESCRIPTION: SEQ ID NO:19:

ATGATGTCGG ACCCTAAGGC TGTT               24

(2) INFORMATION FOR SEQ ID NO:20:

(i) SEQUENCE CHARACTERISTICS:
        (A) LENGTH: 20 Base Pairs
        (B) TYPE: Nucleic Acid
        (C) STRANDEDNESS: Unknown
        (D) TOPOLOGY: Unknown (ii) MOLECULE TYPE: Oligonucleotide (ix) FEATURE:
        (A) NAME/KEY: 354
        (B) LOCATION:
        (C) IDENTIFICATION METHOD:
        (D) OTHER INFORMATION: primer in a polymerase
              chain reaction (xi) SEQUENCE DESCRIPTION: SEQ ID NO:20:

TGGGGACAGT GAGGACCGCC                    20

(2) INFORMATION FOR SEQ ID NO:21:

(i) SEQUENCE CHARACTERISTICS:
        (A) LENGTH: 24 Base Pairs
        (B) TYPE: Nucleic Acid ( C ) STRANDEDNESS: Unknown
( D ) TOPOLOGY: Unknown ( i i ) MOLECULE TYPE: Oligonucleotide ( i x ) FEATURE:
      ( A ) NAME/KEY: JT10 - UP01
      ( B ) LOCATION:
      ( C ) IDENTIFICATION METHOD:
      ( D ) OTHER INFORMATION: primer in a polymerase chain reaction ( x i ) SEQUENCE DESCRIPTION: SEQ ID NO:21:

GGTGTGCAAA TGTGTGCGCC TTAG     24

( 2 ) INFORMATION FOR SEQ ID NO:22:

( i ) SEQUENCE CHARACTERISTICS:
      ( A ) LENGTH: 24 Base Pairs
      ( B ) TYPE: Nucleic Acid
      ( C ) STRANDEDNESS: Unkown
      ( D ) TOPOLOGY: Unknown ( i i ) MOLECULE TYPE: Oligonucleotide ( i x ) FEATURE:
      ( A ) NAME/KEY: JT10 - DP01
      ( B ) LOCATION:
      ( C ) IDENTIFICATION METHOD:
      ( D ) OTHER INFORMATION: primer in a polymerase chain reaction ( x i ) SEQUENCE DESCRIPTION: SEQ ID NO:22:

GGGAGCTGCT TTACCTGTGG ATAC     24

( 2 ) INFORMATION FOR SEQ ID NO:23:

( i ) SEQUENCE CHARACTERISTICS:
      ( A ) LENGTH: 25 Base Pairs
      ( B ) TYPE: Nucleic Acid
      ( C ) STRANDEDNESS: Unknown
      ( D ) TOPOLOGY: Unknown ( i i ) MOLECULE TYPE: Oligonucleotide ( i x ) FEATURE:
      ( A ) NAME/KEY: 1590
      ( B ) LOCATION:
      ( C ) IDENTIFICATION METHOD:
      ( D ) OTHER INFORMATION: primer in a polymerase chain reaction ( x i ) SEQUENCE DESCRIPTION: SEQ ID NO:23:

GGACGCTGGA TTAGAAGGCA GCAAA     25

( 2 ) INFORMATION FOR SEQ ID NO:24:

( i ) SEQUENCE CHARACTERISTICS:
      ( A ) LENGTH: 19 Base Pairs
      ( B ) TYPE: Nucleic Acid
      ( C ) STRANDEDNESS: Unknown
      ( D ) TOPOLOGY: Unknown ( i i ) MOLECULE TYPE: Oligonucleotide ( i x ) FEATURE:
      ( A ) NAME/KEY: 1591
      ( B ) LOCATION:
      ( C ) IDENTIFICATION METHOD:
      ( D ) OTHER INFORMATION: primer in a polymerase chain reaction ( x i ) SEQUENCE DESCRIPTION: SEQ ID NO:24:

CCACACCCAG CCTAGTCCC                                                                                              19

( 2 ) INFORMATION FOR SEQ ID NO:25:

( i ) SEQUENCE CHARACTERISTICS:
        ( A ) LENGTH: 18 Base Pairs
        ( B ) TYPE: Nucleic Acid
        ( C ) STRANDEDNESS: Double
        ( D ) TOPOLOGY: Unknown ( i i ) MOLECULE TYPE: Genomic DNA ( i x ) FEATURE:
        ( A ) NAME/KEY: 5'splice site of EXON 1
        ( B ) LOCATION:
        ( C ) IDENTIFICATION METHOD:
        ( D ) OTHER INFORMATION: 5'Splice Donor site is
              located between nucleotides 9 and 10

( x i ) SEQUENCE DESCRIPTION: SEQ ID NO:25:

TATCCACAGG TAAAGTAG                                                                                               18

( 2 ) INFORMATION FOR SEQ ID NO:26:

( i ) SEQUENCE CHARACTERISTICS:
        ( A ) LENGTH: 18 Base Pairs
        ( B ) TYPE: Nucleic Acid
        ( C ) STRANDEDNESS: Double
        ( D ) TOPOLOGY: Unknown ( i i ) MOLECULE TYPE: Genomic DNA ( i x ) FEATURE:
        ( A ) NAME/KEY: 5'splice site of EXON 2
        ( B ) LOCATION:
        ( C ) IDENTIFICATION METHOD:
        ( D ) OTHER INFORMATION: 5'Splice Donor site is
              located between nucleotides 9 and 10

( x i ) SEQUENCE DESCRIPTION: SEQ ID NO:26:

CCGGAGGAGG TCAGTAGG                                                                                               18

( 2 ) INFORMATION FOR SEQ ID NO:27:

( i ) SEQUENCE CHARACTERISTICS:
        ( A ) LENGTH: 18 Base Pairs
        ( B ) TYPE: Nucleic Acid
        ( C ) STRANDEDNESS: Double
        ( D ) TOPOLOGY: Unknown ( i i ) MOLECULE TYPE: Genomic DNA ( i x ) FEATURE:
        ( A ) NAME/KEY: 5'splice site of EXON 3
        ( B ) LOCATION:
        ( C ) IDENTIFICATION METHOD:
        ( D ) OTHER INFORMATION: 5'Splice Donor site
              is located between nucleotides 9 and 10

( x i ) SEQUENCE DESCRIPTION: SEQ ID NO:27:

TCTCGCTGGG TGAGTGCT                                                                                               18

( 2 ) INFORMATION FOR SEQ ID NO:28:

( i ) SEQUENCE CHARACTERISTICS:
        ( A ) LENGTH: 18 Base Pairs
        ( B ) TYPE: Nucleic Acid
        ( C ) STRANDEDNESS: Double
        ( D ) TOPOLOGY: Unknown ( i i ) MOLECULE TYPE: Genomic DNA ( i x ) FEATURE:

(A) NAME/KEY: 5'splice site of EXON 4
(B) LOCATION:
(C) IDENTIFICATION METHOD:
(D) OTHER INFORMATION: 5'Splice Donor site is located between nucleotides 9 and 10

(x i) SEQUENCE DESCRIPTION: SEQ ID NO:28:

TTGAGAAGAG TGAGTCGC    18

(2) INFORMATION FOR SEQ ID NO:29:

(i) SEQUENCE CHARACTERISTICS:
(A) LENGTH: 18 Base Pairs
(B) TYPE: Nucleic Acid
(C) STRANDEDNESS: Double
(D) TOPOLOGY: Unknown (ii) MOLECULE TYPE: Genomic DNA (ix) FEATURE:
(A) NAME/KEY: 5'splice site of EXON 5
(B) LOCATION:
(C) IDENTIFICATION METHOD:
(D) OTHER INFORMATION: 5'Splice Donor site is located between nucleotides 9 and 10

(x i) SEQUENCE DESCRIPTION: SEQ ID NO:29:

ACTTCAAGGG TGAGCGCG    18

(2) INFORMATION FOR SEQ ID NO:30:

(i) SEQUENCE CHARACTERISTICS:
(A) LENGTH: 18 Base Pairs
(B) TYPE: Nucleic Acid
(C) STRANDEDNESS: Double
(D) TOPOLOGY: Unknown (ii) MOLECULE TYPE: Genomic DNA (ix) FEATURE:
(A) NAME/KEY: 5'splice site of EXON 6
(B) LOCATION:
(C) IDENTIFICATION METHOD:
(D) OTHER INFORMATION: 5'Splice Donor site is located between nucleotides 9 and 10

(x i) SEQUENCE DESCRIPTION: SEQ ID NO:30:

AGCTGCAAGG TCTGTGGG    18

(2) INFORMATION FOR SEQ ID NO:31:

(i) SEQUENCE CHARACTERISTICS:
(A) LENGTH: 18 Base Pairs
(B) TYPE: Nucleic Acid
(C) STRANDEDNESS: Double
(D) TOPOLOGY: Unknown (ii) MOLECULE TYPE: Genomic DNA (ix) FEATURE:
(A) NAME/KEY: 5'splice site of EXON 7
(B) LOCATION:
(C) IDENTIFICATION METHOD:
(D) OTHER INFORMATION: 5'Splice Donor site is located between nucleotides 9 and 10

(x i) SEQUENCE DESCRIPTION: SEQ ID NO:31:

AGGAGATGAG TATGTCTG    18

(2) INFORMATION FOR SEQ ID NO:32:

(i) SEQUENCE CHARACTERISTICS:

( A ) LENGTH: 18 Base Pairs
            ( B ) TYPE: Nucleic Acid
            ( C ) STRANDEDNESS: Double
            ( D ) TOPOLOGY: Unknown ( i i ) MOLECULE TYPE: Genomic DNA ( i x ) FEATURE:
            ( A ) NAME/KEY: 5'splice site of EXON 8
            ( B ) LOCATION:
            ( C ) IDENTIFICATION METHOD:
            ( D ) OTHER INFORMATION: 5'Splice Donor site is
                    located between nucleotides 9 and 10

( x i ) SEQUENCE DESCRIPTION: SEQ ID NO:32:

TTTATCCCTA ACTTCTGT                                                                           1 8

( 2 ) INFORMATION FOR SEQ ID NO:33:

( i ) SEQUENCE CHARACTERISTICS:
            ( A ) LENGTH: 9 Base Pairs
            ( B ) TYPE: Nucleic Acid
            ( C ) STRANDEDNESS: Double
            ( D ) TOPOLOGY: Unknown ( i i ) MOLECULE TYPE: Genomic DNA ( i x ) FEATURE:
            ( A ) NAME/KEY: 3'splice site of INTRON 1
            ( B ) LOCATION:
            ( C ) IDENTIFICATION METHOD:
            ( D ) OTHER INFORMATION: 3'Splice Acceptor site
                    is located between nucleotides 9 and 10

( x i ) SEQUENCE DESCRIPTION: SEQ ID NO:33:

GGACGCTGG                                                                                      9

( 2 ) INFORMATION FOR SEQ ID NO:34:

( i ) SEQUENCE CHARACTERISTICS:
            ( A ) LENGTH: 18 Base Pairs
            ( B ) TYPE: Nucleic Acid
            ( C ) STRANDEDNESS: Double
            ( D ) TOPOLOGY: Unknown ( i i ) MOLECULE TYPE: Genomic DNA ( i x ) FEATURE:
            ( A ) NAME/KEY: 3'splice site of INTRON 2
            ( B ) LOCATION:
            ( C ) IDENTIFICATION METHOD:
            ( D ) OTHER INFORMATION: 3'Splice Acceptor site
                    is located between nucleotides 9 and 10

( x i ) SEQUENCE DESCRIPTION: SEQ ID NO:34:

TTCTTGCAGG CCCCAGGA                                                                           1 8

( 2 ) INFORMATION FOR SEQ ID NO:35:

( i ) SEQUENCE CHARACTERISTICS:
            ( A ) LENGTH: 18 Base Pairs
            ( B ) TYPE: Nucleic Acid
            ( C ) STRANDEDNESS: Double
            ( D ) TOPOLOGY: Unknown ( i i ) MOLECULE TYPE: Genomic DNA ( i x ) FEATURE:
            ( A ) NAME/KEY: 3'splice site of INTRON 3
            ( B ) LOCATION:
            ( C ) IDENTIFICATION METHOD:
            ( D ) OTHER INFORMATION: 3'Splice Acceptor site
                    is located between nucleotides 9 and 10

( x i ) SEQUENCE DESCRIPTION: SEQ ID NO:35:

TCCTGCCAGG GCTCCCCA                                                                                    18

( 2 ) INFORMATION FOR SEQ ID NO:36:

( i ) SEQUENCE CHARACTERISTICS:
        ( A ) LENGTH: 18 Base Pairs
        ( B ) TYPE: Nucleic Acid
        ( C ) STRANDEDNESS: Double
        ( D ) TOPOLOGY: Unknown ( i i ) MOLECULE TYPE: Genomic DNA ( i x ) FEATURE:
        ( A ) NAME/KEY: 3'splice site of INTRON 4
        ( B ) LOCATION:
        ( C ) IDENTIFICATION METHOD:
        ( D ) OTHER INFORMATION: 3'Splice Acceptor site
            is located between nucleotides 9 and 10

( x i ) SEQUENCE DESCRIPTION: SEQ ID NO:36:

CTCTGGCAGG AGCGGACG                                                                                    18

( 2 ) INFORMATION FOR SEQ ID NO:37:

( i ) SEQUENCE CHARACTERISTICS:
        ( A ) LENGTH: 18 Base Pairs
        ( B ) TYPE: Nucleic Acid
        ( C ) STRANDEDNESS: Double
        ( D ) TOPOLOGY: Unknown ( i i ) MOLECULE TYPE: Genomic DNA ( i x ) FEATURE:
        ( A ) NAME/KEY: 3'splice site of INTRON 5
        ( B ) LOCATION:
        ( C ) IDENTIFICATION METHOD:
        ( D ) OTHER INFORMATION: 3'Splice Acceptor site
            is located between nucleotides 9 and 10

( x i ) SEQUENCE DESCRIPTION: SEQ ID NO:37:

TCTTCTCAGA GCTGCGCA                                                                                    18

( 2 ) INFORMATION FOR SEQ ID NO:38:

( i ) SEQUENCE CHARACTERISTICS:
        ( A ) LENGTH: 18 Base Pairs
        ( B ) TYPE: Nucleic Acid
        ( C ) STRANDEDNESS: Double
        ( D ) TOPOLOGY: Unknown ( i i ) MOLECULE TYPE: Genomic DNA ( i x ) FEATURE:
        ( A ) NAME/KEY: 3'splice site of INTRON 6
        ( B ) LOCATION:
        ( C ) IDENTIFICATION METHOD:
        ( D ) OTHER INFORMATION: 3'Splice Acceptor site
            is located between nucleotides 9 and 10

( x i ) SEQUENCE DESCRIPTION: SEQ ID NO:38:

TCTTTCCAGG GCAGTGGG                                                                                    18

( 2 ) INFORMATION FOR SEQ ID NO:39:

( i ) SEQUENCE CHARACTERISTICS:
        ( A ) LENGTH: 18 Base Pairs
        ( B ) TYPE: Nucleic Acid
        ( C ) STRANDEDNESS: Double
        ( D ) TOPOLOGY: Unknown ( i i ) MOLECULE TYPE: Genomic DNA ( i x ) FEATURE:
    ( A ) NAME/KEY: 3'splice site of INTRON 7
    ( B ) LOCATION:
    ( C ) IDENTIFICATION METHOD:
    ( D ) OTHER INFORMATION: 3'Splice Acceptor site
        is located between nucleotides 9 and 10

( x i ) SEQUENCE DESCRIPTION: SEQ ID NO:39:

TTGTCTCAGA TTGCCCAG                                                                    18

( 2 ) INFORMATION FOR SEQ ID NO:40:

( i ) SEQUENCE CHARACTERISTICS:
        ( A ) LENGTH: 18 Base Pairs
        ( B ) TYPE: Nucleic Acid
        ( C ) STRANDEDNESS: Double
        ( D ) TOPOLOGY: Unknown ( i i ) MOLECULE TYPE: Genomic DNA ( i x ) FEATURE:
        ( A ) NAME/KEY: 3'splice site of INTRON 8
        ( B ) LOCATION:
        ( C ) IDENTIFICATION METHOD:
        ( D ) OTHER INFORMATION: 3'Splice Acceptor site
            is located between nucleotides 9 and 10

( x i ) SEQUENCE DESCRIPTION: SEQ ID NO:40:

TCTCTACAGA GCTGCAAT                                                                    18

( 2 ) INFORMATION FOR SEQ ID NO:41:

( i ) SEQUENCE CHARACTERISTICS:
        ( A ) LENGTH: 737 Base Pairs
        ( B ) TYPE: Nucleic Acid
        ( C ) STRANDEDNESS: Double
        ( D ) TOPOLOGY: Unknown ( i i ) MOLECULE TYPE: Genomic DNA ( i x ) FEATURE:
        ( A ) NAME/KEY: PEDF Promoter
        ( B ) LOCATION:
        ( C ) IDENTIFICATION METHOD:
        ( D ) OTHER INFORMATION: EXON begins at 614 and
            ends at 728 of PEDF GENE ( x i ) SEQUENCE DESCRIPTION: SEQ ID NO:41:

TTCTTTTTTT GAGACGGGGT CTCGCTCTGC TCGCCCAGGA                                             40

TGGAGTGCAG TGGTGTGATC TCAGCTCACT GCAACCTCCG                                             80

CCTCCCAGGT TTAAGTGATT CTCCTGCCTC AGACTCCCAA                                            120

GTAGCTGGGA CTACAGGTGC GCGCCAACAC ACCTGGGTAA                                            160

TTTTGTTTGT ATTTTTAGTA GAGATGGGGT TTCACCGTGT                                            200

TGACTAGGCT GGTCTCGAAC CTCCTGACCT CAGGTGATCC                                            240

CCCGGCCTCG GTCTCCCAAA GTGCTGGGGA TAACAAGCGT                                            280

GAGCCACTGC GCCCAGCTTT GTTTGCATTT TTAGGTGAGA                                            320

TGGGGTTTCA CCACGTTGGC CAGGCTGGTC TTGAACTCCT                                            360

GACCTCAGGT GATGCACCTG CCTCAGTCTC CCAAAGTGCT                                            400

GGATTACAGG CGTTAGCCCC TGCGCCCGGC CCCTGAAGGA                                            440

AAATCTAAAG GAAGAGGAAG GTGTGCAAAT GTGTGCGCCT                                            480

TAGGCGTAAT GGATGGTGGT GCAGCAGTGG GTTAAAGTTA                                            520

|                 |                 |                 |                 | |
|---|---|---|---|---|
| ACACGAGACA | GTGATGCAAT | CACAGGAATC | CAAATTGAGT | 560 |
| GCAGGTCGCT | TTAAGAAAGG | AGTAGCTGTA | ATCTGAAGCC | 600 |
| ATCTGAAGCC | TGCTGGACGC | TGGATTAGAA | GGCAGCAAAA | 640 |
| AAAGCTCTGT | GCTGGCTGGA | GCCCCCTCAG | TGCAGGCTTA | 680 |
| GAGGGACTAG | GCTGGGTGTG | GAGCTGCAGC | GTATCCACAG | 720 |
| GCCCCAGGGT | AAAGTAG | | | 737 |

( 2 ) INFORMATION FOR SEQ ID NO:42:

( i ) SEQUENCE CHARACTERISTICS:
        ( A ) LENGTH: 88 Base Pairs
        ( B ) TYPE: Nucleic Acid
        ( C ) STRANDEDNESS: Double
        ( D ) TOPOLOGY: Unknown ( i i ) MOLECULE TYPE: Genomic DNA ( i x ) FEATURE:
        ( A ) NAME/KEY: PEDF Promoter
        ( B ) LOCATION:
        ( C ) IDENTIFICATION METHOD:
        ( D ) OTHER INFORMATION: EXON PEDF GENE
            begins at 9

( x i ) SEQUENCE DESCRIPTION: SEQ ID NO:42:

|                 |                 |                 |                 | |
|---|---|---|---|---|
| TTCTTGCAGA | TGCAGGCCCT | GGTGCTACTC | CTCTGCATTG | 40 |
| GAGCCCTCCT | CGGGCACAGC | AGCTGCCAGA | ACCCTGCCAG | 80 |
| CCCCCCGG | | | | 88 |

We claim:

1. A method of prolonging neuron cell survival comprising: treating a cell population comprising neurons with an effective amount of pigment epithelium-derived factor (PEDF), as shown in SEQ ID NO: 2 or a biologically active truncated fragment of SEQ ID NO: 2, thereby prolonging neuronal cell survival in said population.

2. A method of inhibiting glial cell proliferation comprising: treating a cell population comprising glial cells with an effective amount of pigment epithelium-derived factor (PEDF), as shown in SEQ ID NO: 2 or a biologically active truncated fragment of SEQ ID NO: 2, thereby inhibiting glial cell proliferation in said population.

3. The method according to claim 1 wherein the neuronal cells are in a tissue cell culture.

4. The method according to claim 1 further comprising:

setting up a cell culture; and treating said cell culture with an effective amount of PEDF.

5. The method according to claim 2, wherein the glial cells are part of a tumor growth.

6. The method according to claim 2, wherein glial cell growth inhibited is a gliosis.

* * * * *

UNITED STATES PATENT AND TRADEMARK OFFICE
CERTIFICATE OF CORRECTION

PATENT NO.    :    5,840,686

DATED         :    November 24, 1998

INVENTORS     :    GERALD J. CHADER, SOFIA PATRICIA BECERRA, JOAN P. SCHWARTZ, TAKAYUKI TANIWAKI, YUKIHIRO SUGITA

It is certified that error appears in the above-identified patent and that said Letters Patent is hereby corrected as shown below:

In SEQ ID NO:1, nucleotides 407-408, delete "CG" and insert -- GC --;

In SEQ ID NO:2, amino acids 97-98, delete "Asp Glu" and insert -- Glu Gln --;

In SEQ ID NO:3, amino acids 58-59, delete "Asp Glu" and insert -- Glu Gln --.

Signed and Sealed this

Eighteenth Day of May, 1999

Attest:

Q. TODD DICKINSON

Attesting Officer    Acting Commissioner of Patents and Trademarks